United States Patent
Houser et al.

(10) Patent No.: US 10,945,783 B2
(45) Date of Patent: *Mar. 16, 2021

(54) SURGICAL INSTRUMENT WITH MODULAR SHAFT AND END EFFECTOR

(71) Applicant: Ethicon LLC, Guaynabo, PR (US)

(72) Inventors: Kevin L. Houser, Springboro, OH (US); Cory G. Kimball, Hamilton, OH (US); Gavin M. Monson, Oxford, OH (US); Richard W. Timm, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/530,009

(22) Filed: Aug. 2, 2019

(65) Prior Publication Data

US 2020/0078084 A1    Mar. 12, 2020

Related U.S. Application Data

(60) Continuation of application No. 15/342,218, filed on Nov. 3, 2016, now Pat. No. 10,376,304, which is a (Continued)

(51) Int. Cl.
*A61B 17/32* (2006.01)
*A61B 18/12* (2006.01)
(Continued)

(52) U.S. Cl.
CPC .... *A61B 18/1442* (2013.01); *A61B 17/00234* (2013.01); *A61B 17/2812* (2013.01);
(Continued)

(58) Field of Classification Search
CPC ...... A61B 17/00234; A61B 17/320068; A61B 17/320092; A61B 18/00; A61B 18/04;
(Continued)

(56) References Cited

U.S. PATENT DOCUMENTS

| | | |
|---|---|---|
| 1,754,806 A | 4/1930 | Stevenson |
| 2,340,822 A | 2/1944 | Scott |
| | (Continued) | |

FOREIGN PATENT DOCUMENTS

| | | |
|---|---|---|
| DE | 102008051866 | 10/2010 |
| DE | 102009013034 | 10/2010 |
| | (Continued) | |

OTHER PUBLICATIONS

Indian Office Action, Examination Report, dated Sep. 25, 2019 for Application No. 3969/DELNP/2013, 8 pgs.

(Continued)

*Primary Examiner* — Mark Bockelman
(74) *Attorney, Agent, or Firm* — Frost Brown Todd LLC

(57) ABSTRACT

A surgical instrument operable to sever tissue includes a body assembly and a selectively coupleable end effector assembly. The end effector assembly may include a transmission assembly, an end effector, and a rotational knob operable to rotate the transmission assembly and the end effector. The body assembly includes a trigger and a casing having a distal aperture configured to receive a portion of the end effector assembly. First and second coupling mechanism portions cooperatively couple the end effector assembly to the body assembly for use. The coupling may mechanically and/or electrically couple the end effector assembly to the body assembly via various coupling mechanisms. For instance, a threaded slip nut may couple to threads within the body assembly. In one configuration, the end effector assembly may have locking tabs that rotate into rotational recesses in the body assembly. The locking tabs may include electrical contacts and/or optically perceivable indicators.

20 Claims, 16 Drawing Sheets

Related U.S. Application Data division of application No. 13/269,870, filed on Oct. 10, 2011, now Pat. No. 9,510,895.

(60) Provisional application No. 61/410,603, filed on Nov. 5, 2010, provisional application No. 61/487,846, filed on May 19, 2011.

(51) Int. Cl.

| | |
|---|---|
| *A61B 18/14* | (2006.01) |
| *H02J 7/02* | (2016.01) |
| *H02J 7/00* | (2006.01) |
| *H01M 10/48* | (2006.01) |
| *H01M 10/46* | (2006.01) |
| *H01M 2/26* | (2006.01) |
| *H01M 2/10* | (2006.01) |
| *A61N 7/00* | (2006.01) |
| *A61B 18/04* | (2006.01) |
| *A61B 18/00* | (2006.01) |
| *A61B 17/28* | (2006.01) |
| *A61B 17/00* | (2006.01) |
| *A61B 90/40* | (2016.01) |
| *A61B 90/00* | (2016.01) |
| *A61B 46/10* | (2016.01) |
| *A61B 34/00* | (2016.01) |
| *G16H 40/63* | (2018.01) |
| *G16H 20/40* | (2018.01) |
| *A61B 90/98* | (2016.01) |
| *A61B 90/90* | (2016.01) |
| *A61B 17/29* | (2006.01) |
| *A61B 17/285* | (2006.01) |
| *A61B 17/064* | (2006.01) |

(52) U.S. Cl.
CPC ............ *A61B 17/320068* (2013.01); *A61B 17/320092* (2013.01); *A61B 18/00* (2013.01); *A61B 18/04* (2013.01); *A61B 18/12* (2013.01); *A61B 18/1206* (2013.01); *A61B 18/14* (2013.01); *A61B 18/1445* (2013.01); *A61B 34/25* (2016.02); *A61B 46/10* (2016.02); *A61B 90/08* (2016.02); *A61B 90/40* (2016.02); *A61B 90/90* (2016.02); *A61B 90/98* (2016.02); *A61N 7/00* (2013.01); *G16H 20/40* (2018.01); *G16H 40/63* (2018.01); *H01M 2/10* (2013.01); *H01M 2/1016* (2013.01); *H01M 2/26* (2013.01); *H01M 10/46* (2013.01); *H01M 10/48* (2013.01); *H02J 7/0044* (2013.01); *H02J 7/0045* (2013.01); *H02J 7/0047* (2013.01); *H02J 7/025* (2013.01); *A61B 17/064* (2013.01); *A61B 17/285* (2013.01); *A61B 18/1233* (2013.01); *A61B 2017/00017* (2013.01); *A61B 2017/0046* (2013.01); *A61B 2017/00084* (2013.01); *A61B 2017/0084* (2013.01); *A61B 2017/00398* (2013.01); *A61B 2017/00473* (2013.01); *A61B 2017/00477* (2013.01); *A61B 2017/00482* (2013.01); *A61B 2017/00734* (2013.01); *A61B 2017/291* (2013.01); *A61B 2017/293* (2013.01); *A61B 2017/294* (2013.01); *A61B 2017/2929* (2013.01); *A61B 2017/2931* (2013.01); *A61B 2017/2933* (2013.01); *A61B 2017/320069* (2017.08); *A61B 2017/320071* (2017.08); *A61B 2017/320094* (2017.08); *A61B 2017/320095* (2017.08); *A61B 2018/0019* (2013.01); *A61B 2018/00172* (2013.01); *A61B 2018/00178* (2013.01); *A61B 2018/00589* (2013.01); *A61B 2018/00595* (2013.01); *A61B 2018/00601* (2013.01); *A61B 2018/00607* (2013.01); *A61B 2018/00791* (2013.01); *A61B 2018/00988* (2013.01); *A61B 2018/1226* (2013.01); *A61B 2018/1412* (2013.01); *A61B 2018/1455* (2013.01); *A61B 2090/0803* (2016.02); *A61B 2090/0813* (2016.02); *A61B 2090/0814* (2016.02); *H01M 2/1022* (2013.01); *H01M 2220/30* (2013.01); *H02J 7/0048* (2020.01); *Y10T 29/49005* (2015.01); *Y10T 29/49895* (2015.01); *Y10T 29/53913* (2015.01)

(58) Field of Classification Search
CPC ..... A61B 18/12; A61B 18/14; A61B 18/1442; A61B 18/1445; A61B 17/285; A61B 18/1233; A61B 19/38; A61B 2017/00084; A61B 2017/00398; A61B 2017/0046; A61B 2017/00473; A61B 2017/00477; A61B 2017/00482; A61B 2017/00734; A61B 2017/291; A61B 2017/2929; A61B 2017/293; A61B 2017/2931; A61B 2017/2933; A61B 2017/94; A61B 2018/00178; A61B 2018/00791; A61B 2018/00988; A61B 2018/1226; A61B 2018/1412; A61B 2018/1455; A61B 2019/4815; A61B 2019/4868; A61B 2019/4873; A61B 18/1206; A61B 19/56; A61B 17/064; H02J 7/0045; Y10T 29/53913; Y10T 29/49895; Y10T 29/49005; H01M 2/10; H01M 2/26
See application file for complete search history.

(56) References Cited

U.S. PATENT DOCUMENTS

| | | |
|---|---|---|
| 3,297,192 A | 1/1967 | Swett |
| 3,419,198 A | 12/1968 | Pettersen |
| 3,619,671 A | 11/1971 | Shoh |
| 3,806,225 A | 4/1974 | Codrino |
| 4,034,762 A | 7/1977 | Cosens et al. |
| 4,057,220 A | 11/1977 | Kudlacek |
| 4,535,773 A | 8/1985 | Yoon |
| 4,641,076 A | 2/1987 | Linden et al. |
| 4,662,068 A | 5/1987 | Polonsky |
| 4,666,037 A | 5/1987 | Weissman |
| 4,685,459 A | 8/1987 | Koch et al. |
| 4,717,018 A | 1/1988 | Sacherer et al. |
| 4,717,050 A | 1/1988 | Wright |
| 4,721,097 A | 1/1988 | D'Amelio |
| 4,768,969 A | 9/1988 | Bauer et al. |
| 4,800,878 A | 1/1989 | Cartmell |
| 4,844,259 A | 7/1989 | Glowczewskie, Jr. et al. |
| 4,878,493 A | 11/1989 | Pasternak et al. |
| 5,071,417 A | 12/1991 | Sinofsky |
| 5,107,155 A | 4/1992 | Yamaguchi |
| 5,144,771 A | 9/1992 | Miwa |
| 5,169,733 A | 12/1992 | Savovic et al. |
| 5,176,677 A | 1/1993 | Wuchinich |
| 5,246,109 A | 9/1993 | Markle et al. |
| 5,273,177 A | 12/1993 | Campbell |
| 5,277,694 A | 1/1994 | Leysieffer et al. |
| 5,308,358 A | 5/1994 | Bond et al. |
| 5,317,485 A | 5/1994 | Merjanian |
| 5,322,055 A | 6/1994 | Davison |
| 5,339,799 A | 8/1994 | Kami et al. |
| 5,358,508 A | 10/1994 | Cobb et al. |
| 5,361,902 A | 11/1994 | Abidin et al. |
| 5,429,229 A | 7/1995 | Chester et al. |
| 5,449,370 A | 9/1995 | Vaitekunas |
| 5,454,378 A | 10/1995 | Palmer et al. |
| 5,501,607 A | 3/1996 | Yoshioka et al. |
| 5,507,297 A | 4/1996 | Slater et al. |

(56) References Cited

U.S. PATENT DOCUMENTS

| | | |
|---|---|---|
| 5,561,881 A | 10/1996 | Klinger et al. |
| 5,578,052 A | 11/1996 | Koros et al. |
| 5,580,258 A | 12/1996 | Wakata |
| 5,582,617 A | 12/1996 | Klieman et al. |
| 5,590,778 A | 1/1997 | Dutchik |
| 5,592,065 A | 1/1997 | Oglesbee et al. |
| 5,597,371 A | 1/1997 | Toukura |
| 5,599,350 A | 2/1997 | Schulze et al. |
| 5,630,420 A | 5/1997 | Vaitekunas |
| 5,630,456 A | 5/1997 | Hugo et al. |
| 5,690,222 A | 11/1997 | Peters |
| 5,707,369 A | 1/1998 | Vaitekunas et al. |
| 5,741,305 A | 4/1998 | Vincent et al. |
| 5,776,155 A | 7/1998 | Beaupre et al. |
| 5,800,336 A | 9/1998 | Ball et al. |
| 5,817,128 A | 10/1998 | Storz |
| 5,868,244 A | 2/1999 | Ivanov et al. |
| 5,871,493 A | 2/1999 | Sjostrom et al. |
| 5,873,873 A | 2/1999 | Smith et al. |
| 5,882,310 A | 3/1999 | Marian, Jr. |
| 5,893,835 A | 4/1999 | Witt et al. |
| 5,893,874 A | 4/1999 | Bourque et al. |
| 5,935,144 A | 8/1999 | Estabrook |
| 5,938,633 A | 8/1999 | Beaupre |
| 5,944,737 A | 8/1999 | Tsonton et al. |
| 5,951,575 A | 9/1999 | Bolduc et al. |
| 5,980,510 A | 11/1999 | Tsonton et al. |
| 5,997,531 A | 12/1999 | Loeb et al. |
| 6,018,227 A | 1/2000 | Kumar et al. |
| 6,051,010 A | 4/2000 | Dimatteo et al. |
| 6,056,735 A | 5/2000 | Okada et al. |
| 6,063,098 A | 5/2000 | Houser et al. |
| 6,066,151 A | 5/2000 | Miyawaki et al. |
| 6,083,191 A | 7/2000 | Rose |
| 6,083,223 A | 7/2000 | Baker |
| 6,099,537 A | 8/2000 | Sugai et al. |
| 6,113,593 A | 9/2000 | Tu et al. |
| 6,123,702 A | 9/2000 | Swanson et al. |
| 6,165,191 A | 12/2000 | Shibata et al. |
| 6,190,386 B1 | 2/2001 | Rydell |
| 6,204,592 B1 | 3/2001 | Hur |
| 6,214,023 B1 | 4/2001 | Whipple et al. |
| 6,246,896 B1 | 6/2001 | Dumoulin et al. |
| 6,248,238 B1 | 6/2001 | Burtin et al. |
| 6,287,304 B1 | 9/2001 | Eggers et al. |
| 6,325,811 B1 | 12/2001 | Messerly |
| 6,339,368 B1 | 1/2002 | Leith |
| 6,398,755 B1 | 6/2002 | Belef et al. |
| 6,409,742 B1 | 6/2002 | Fulton, III et al. |
| 6,500,176 B1 | 12/2002 | Truckai et al. |
| 6,500,188 B2 | 12/2002 | Harper et al. |
| 6,512,667 B2 | 1/2003 | Shiue et al. |
| 6,514,267 B2 | 2/2003 | Jewett |
| 6,520,185 B1 | 2/2003 | Bommannan et al. |
| 6,561,983 B2 | 5/2003 | Cronin et al. |
| 6,562,032 B1 | 5/2003 | Ellman et al. |
| 6,609,414 B2 | 8/2003 | Mayer et al. |
| 6,622,731 B2 | 9/2003 | Daniel et al. |
| 6,623,500 B1 | 9/2003 | Cook et al. |
| 6,626,901 B1 | 9/2003 | Treat et al. |
| 6,647,281 B2 | 11/2003 | Morency |
| 6,650,091 B1 | 11/2003 | Shiue et al. |
| 6,650,975 B2 | 11/2003 | Ruffner |
| 6,656,177 B2 | 12/2003 | Truckai et al. |
| 6,658,301 B2 | 12/2003 | Loeb et al. |
| 6,666,875 B1 | 12/2003 | Sakurai et al. |
| 6,706,038 B2 | 3/2004 | Francischelli et al. |
| 6,717,193 B2 | 4/2004 | Olewine et al. |
| 6,730,042 B2 | 5/2004 | Fulton et al. |
| 6,753,673 B2 | 6/2004 | Shiue et al. |
| 6,758,855 B2 | 7/2004 | Fulton, III et al. |
| 6,761,698 B2 | 7/2004 | Shibata et al. |
| 6,761,701 B2 | 7/2004 | Cucin |
| 6,783,524 B2 | 8/2004 | Anderson et al. |
| 6,815,206 B2 | 11/2004 | Lin et al. |
| 6,821,671 B2 | 11/2004 | Hinton et al. |
| 6,836,097 B2 | 12/2004 | Turner et al. |
| 6,838,862 B2 | 1/2005 | Luu |
| 6,847,192 B2 | 1/2005 | Turner et al. |
| 6,860,880 B2 | 3/2005 | Treat et al. |
| 6,869,435 B2 | 3/2005 | Blake |
| 6,923,807 B2 | 8/2005 | Ryan et al. |
| 6,982,696 B1 | 1/2006 | Shahoian |
| 6,998,822 B2 | 2/2006 | Turner et al. |
| 7,031,155 B2 | 4/2006 | Sauciuc et al. |
| 7,061,749 B2 | 6/2006 | Liu et al. |
| 7,077,853 B2 | 7/2006 | Kramer et al. |
| 7,083,589 B2 | 8/2006 | Banko et al. |
| 7,085,123 B2 | 8/2006 | Shiue et al. |
| 7,101,371 B2 | 9/2006 | Dycus et al. |
| 7,112,201 B2 | 9/2006 | Truckai et al. |
| 7,125,409 B2 | 10/2006 | Truckai et al. |
| 7,150,712 B2 | 12/2006 | Buehlmann et al. |
| 7,169,146 B2 | 1/2007 | Truckai et al. |
| 7,186,253 B2 | 3/2007 | Truckai et al. |
| 7,186,473 B2 | 3/2007 | Shiue et al. |
| 7,189,233 B2 | 3/2007 | Truckai et al. |
| 7,220,951 B2 | 5/2007 | Truckai et al. |
| 7,221,216 B2 | 5/2007 | Nguyen |
| 7,232,440 B2 | 6/2007 | Dumbauld et al. |
| 7,244,024 B2 | 7/2007 | Biscardi |
| 7,292,227 B2 | 11/2007 | Fukumoto et al. |
| 7,296,804 B2 | 11/2007 | Lechot et al. |
| 7,303,556 B2 | 12/2007 | Metzger et al. |
| 7,309,849 B2 | 12/2007 | Truckai et al. |
| 7,311,709 B2 | 12/2007 | Truckai et al. |
| 7,349,741 B2 | 3/2008 | Maltan et al. |
| 7,354,440 B2 | 4/2008 | Truckai et al. |
| 7,364,061 B2 | 4/2008 | Swayze et al. |
| 7,364,554 B2 | 4/2008 | Bolze et al. |
| 7,381,209 B2 | 6/2008 | Truckai et al. |
| 7,416,101 B2 | 8/2008 | Shelton, IV et al. |
| 7,422,139 B2 | 9/2008 | Shelton, IV et al. |
| 7,464,846 B2 | 12/2008 | Shelton, IV et al. |
| 7,473,145 B2 | 1/2009 | Her et al. |
| 7,479,152 B2 | 1/2009 | Fulton, III et al. |
| 7,494,492 B2 | 2/2009 | Da Silva et al. |
| D594,983 S | 6/2009 | Price et al. |
| 7,560,903 B2 | 7/2009 | Thrap |
| 7,563,142 B1 | 7/2009 | Wenger et al. |
| 7,573,151 B2 | 8/2009 | Acena et al. |
| 7,583,564 B2 | 9/2009 | Ketahara et al. |
| 7,638,958 B2 | 12/2009 | Philipp et al. |
| 7,643,378 B2 | 1/2010 | Genosar |
| 7,658,247 B2 | 2/2010 | Carter |
| 7,692,411 B2 | 4/2010 | Trainor et al. |
| 7,717,312 B2 | 5/2010 | Beetel |
| 7,721,936 B2 | 5/2010 | Shalton, IV et al. |
| 7,738,971 B2 | 6/2010 | Swayze et al. |
| 7,761,198 B2 | 7/2010 | Bhardwaj |
| 7,766,910 B2 | 8/2010 | Hixson et al. |
| 7,766,929 B2 | 8/2010 | Masuda |
| 7,770,722 B2 | 8/2010 | Donahoe et al. |
| 7,770,775 B2 | 8/2010 | Shelton et al. |
| 7,776,037 B2 | 8/2010 | Odom |
| 7,780,660 B2 | 8/2010 | Bourne et al. |
| 7,802,121 B1 | 9/2010 | Zansky et al. |
| 7,815,658 B2 | 10/2010 | Murakami |
| 7,845,537 B2 | 12/2010 | Shelton, IV et al. |
| 7,846,155 B2 | 12/2010 | Houser et al. |
| 7,846,159 B2 | 12/2010 | Morrison et al. |
| 7,862,579 B2 | 1/2011 | Ortiz et al. |
| 7,889,489 B2 | 2/2011 | Richardson et al. |
| 7,918,848 B2 | 4/2011 | Lau et al. |
| 7,922,063 B2 | 4/2011 | Zemlok et al. |
| 7,923,151 B2 | 4/2011 | Lam et al. |
| 7,948,208 B2 | 5/2011 | Partovi et al. |
| 7,952,322 B2 | 5/2011 | Partovi et al. |
| 7,952,873 B2 | 5/2011 | Glahn et al. |
| 7,959,050 B2 | 6/2011 | Smith et al. |
| 7,977,921 B2 | 7/2011 | Bahai et al. |
| 7,982,439 B2 | 7/2011 | Trainor et al. |
| 8,038,025 B2 | 10/2011 | Stark et al. |
| 8,040,107 B2 | 10/2011 | Ishii |

(56) References Cited

U.S. PATENT DOCUMENTS

| | | |
|---|---|---|
| 8,052,605 B2 | 11/2011 | Muller et al. |
| 8,058,771 B2 | 11/2011 | Giordano et al. |
| 8,075,530 B2 | 12/2011 | Taylor et al. |
| 8,097,011 B2 | 1/2012 | Hideo et al. |
| 8,142,461 B2 | 3/2012 | Houser et al. |
| 8,147,488 B2 | 4/2012 | Masuda |
| 8,177,776 B2 | 5/2012 | Humayun et al. |
| 8,195,271 B2 | 6/2012 | Rahn |
| 8,210,411 B2 | 7/2012 | Yates et al. |
| 8,216,212 B2 | 7/2012 | Grant et al. |
| 8,221,418 B2 | 7/2012 | Prakash et al. |
| 8,240,498 B2 | 8/2012 | Ramsey et al. |
| 8,246,608 B2 | 8/2012 | Omori et al. |
| 8,246,642 B2 | 8/2012 | Houser et al. |
| 8,251,994 B2 | 8/2012 | McKenna et al. |
| 8,267,094 B2 | 9/2012 | Danek et al. |
| 8,277,446 B2 | 10/2012 | Heard |
| 8,292,882 B2 | 10/2012 | Danek et al. |
| 8,292,888 B2 | 10/2012 | Whitman |
| 8,298,253 B2 | 10/2012 | Charles |
| 8,301,262 B2 | 10/2012 | Mi et al. |
| 8,328,802 B2 | 12/2012 | Deville et al. |
| 8,333,764 B2 | 12/2012 | Francischelli et al. |
| 8,336,725 B2 | 12/2012 | Ramsey et al. |
| 8,337,097 B2 | 12/2012 | Cao |
| 8,344,690 B2 | 1/2013 | Smith et al. |
| 8,372,099 B2 | 2/2013 | Deville et al. |
| 8,377,059 B2 | 2/2013 | Deville et al. |
| 8,400,108 B2 | 3/2013 | Powell et al. |
| 8,403,948 B2 | 3/2013 | Deville et al. |
| 8,403,949 B2 | 3/2013 | Palmer et al. |
| 8,403,950 B2 | 3/2013 | Palmer et al. |
| 8,419,757 B2 | 4/2013 | Smith et al. |
| 8,419,758 B2 | 4/2013 | Smith et al. |
| 8,425,545 B2 | 4/2013 | Smith et al. |
| 8,444,653 B2 | 5/2013 | Nycz et al. |
| 8,444,662 B2 | 5/2013 | Palmer et al. |
| 8,449,529 B2 | 5/2013 | Bek et al. |
| 8,461,744 B2 | 6/2013 | Wiener et al. |
| 8,487,487 B2 | 7/2013 | Dietz et al. |
| 8,550,106 B2 | 10/2013 | Hebach et al. |
| 8,550,981 B2 | 10/2013 | Woodruff et al. |
| 8,551,088 B2 | 10/2013 | Falkenstein et al. |
| 8,564,242 B2 | 10/2013 | Hansford et al. |
| 8,573,461 B2 | 11/2013 | Shelton et al. |
| 8,602,287 B2 | 12/2013 | Laurent et al. |
| 8,608,045 B2 | 12/2013 | Smith et al. |
| 8,617,077 B2 | 12/2013 | van Groningen et al. |
| 8,622,274 B2 | 1/2014 | Yates et al. |
| 8,623,027 B2 | 1/2014 | Price et al. |
| 8,632,535 B2 | 1/2014 | Shelton, IV et al. |
| 8,641,629 B2 | 2/2014 | Kurokawa |
| 8,657,174 B2 | 2/2014 | Yates et al. |
| 8,663,112 B2 | 3/2014 | Slayton et al. |
| 8,733,614 B2 | 5/2014 | Ross et al. |
| 8,758,342 B2 | 6/2014 | Bales et al. |
| 8,784,415 B2 | 7/2014 | Malackowski et al. |
| 8,808,319 B2 | 8/2014 | Houser et al. |
| 8,834,465 B2 | 9/2014 | Ramstein et al. |
| 8,864,761 B2 | 10/2014 | Johnson et al. |
| 8,906,017 B2 | 12/2014 | Rioux et al. |
| 8,939,974 B2 | 1/2015 | Boudreaux et al. |
| 8,961,441 B2 | 2/2015 | Cioanta et al. |
| 8,968,648 B2 | 3/2015 | Kaneko |
| 8,986,302 B2 | 3/2015 | Boudreaux et al. |
| 8,998,939 B2 | 4/2015 | Price et al. |
| 9,000,720 B2 | 4/2015 | Stulen et al. |
| 9,011,336 B2 | 4/2015 | Slayton et al. |
| 9,011,427 B2 | 4/2015 | Price et al. |
| 9,011,471 B2 | 4/2015 | Timm et al. |
| 9,017,849 B2 | 4/2015 | Stulen et al. |
| 9,017,851 B2 | 4/2015 | Felder et al. |
| 9,023,071 B2 | 5/2015 | Miller et al. |
| 9,039,720 B2 | 5/2015 | Madan |
| 9,044,261 B2 | 6/2015 | Houser |
| 9,050,125 B2 | 6/2015 | Boudreaux |
| 9,060,750 B2 | 6/2015 | Lam |
| 9,072,523 B2 | 7/2015 | Houser et al. |
| 9,072,543 B2 | 7/2015 | Miller et al. |
| 9,078,671 B2 | 7/2015 | Beale et al. |
| 9,089,338 B2 | 7/2015 | Smith et al. |
| 9,095,346 B2 | 8/2015 | Houser et al. |
| 9,113,903 B2 | 8/2015 | Unger et al. |
| 9,161,803 B2 | 10/2015 | Yates et al. |
| 9,179,912 B2 | 11/2015 | Yates et al. |
| 9,186,046 B2 | 11/2015 | Ramamurthy et al. |
| 9,186,047 B2 | 11/2015 | Ramamurthy et al. |
| 9,192,428 B2 | 11/2015 | Houser et al. |
| 9,247,986 B2 | 2/2016 | Haberstich et al. |
| 9,308,009 B2 | 4/2016 | Madan et al. |
| 9,318,271 B2 | 4/2016 | Fletcher et al. |
| 9,364,279 B2 | 6/2016 | Houser et al. |
| 9,364,288 B2 | 6/2016 | Smith et al. |
| 9,375,255 B2 | 6/2016 | Houser et al. |
| 9,381,058 B2 | 7/2016 | Houser et al. |
| 9,421,062 B2 | 8/2016 | Houser et al. |
| 9,441,954 B2 | 9/2016 | Ramamurthy et al. |
| 9,500,472 B2 | 11/2016 | Ramamurthy et al. |
| 9,500,473 B2 | 11/2016 | Ramamurthy et al. |
| 9,510,895 B2 | 12/2016 | Houser et al. |
| 9,526,921 B2 | 12/2016 | Kimball et al. |
| 9,597,143 B2 | 3/2017 | Madan et al. |
| 9,622,832 B2 | 4/2017 | Birkenbach et al. |
| 9,629,652 B2 | 4/2017 | Mumaw et al. |
| 9,649,150 B2 | 5/2017 | Houser et al. |
| 9,782,214 B2 | 10/2017 | Houser et al. |
| 9,782,215 B2 | 10/2017 | Haberstich et al. |
| 10,085,792 B2 | 10/2018 | Johnson et al. |
| 10,143,513 B2 | 12/2018 | Houser et al. |
| 10,376,304 B2 | 8/2019 | Houser et al. |
| 2001/0032666 A1 | 10/2001 | Jenson et al. |
| 2002/0165577 A1 | 11/2002 | Witt et al. |
| 2003/0093103 A1 | 5/2003 | Malackowski et al. |
| 2003/0109802 A1 | 6/2003 | Laeseke et al. |
| 2003/0114851 A1 | 6/2003 | Truckai et al. |
| 2003/0144680 A1 | 7/2003 | Kellogg et al. |
| 2004/0097911 A1 | 5/2004 | Murakami et al. |
| 2004/0116952 A1 | 6/2004 | Sakurai et al. |
| 2004/0133189 A1 | 7/2004 | Sakurai |
| 2004/0173487 A1 | 9/2004 | Johnson et al. |
| 2005/0021065 A1 | 1/2005 | Yamada et al. |
| 2005/0033195 A1 | 2/2005 | Fulton, III et al. |
| 2005/0171522 A1 | 8/2005 | Christopherson |
| 2005/0203546 A1 | 9/2005 | Van Wyk et al. |
| 2006/0030797 A1 | 2/2006 | Zhou et al. |
| 2006/0079829 A1 | 4/2006 | Fulton, III et al. |
| 2006/0079874 A1 | 4/2006 | Faller et al. |
| 2006/0079877 A1 | 4/2006 | Houser et al. |
| 2006/0079879 A1 | 4/2006 | Faller et al. |
| 2006/0253176 A1 | 11/2006 | Caruso et al. |
| 2007/0027447 A1 | 2/2007 | Theroux et al. |
| 2007/0103437 A1 | 5/2007 | Rosenberg |
| 2007/0191713 A1 | 8/2007 | Eichmann et al. |
| 2007/0207354 A1 | 9/2007 | Curello et al. |
| 2007/0261978 A1 | 11/2007 | Sanderson |
| 2007/0265613 A1 | 11/2007 | Edelstein et al. |
| 2007/0265620 A1 | 11/2007 | Kraas et al. |
| 2007/0282333 A1 | 12/2007 | Fortson et al. |
| 2008/0003491 A1 | 1/2008 | Yahnker et al. |
| 2008/0004656 A1 | 1/2008 | Livneh |
| 2008/0057470 A1 | 3/2008 | Levy et al. |
| 2008/0147058 A1 | 6/2008 | Horrell et al. |
| 2008/0150754 A1 | 6/2008 | Quendt |
| 2008/0173651 A1 | 7/2008 | Ping |
| 2008/0188810 A1 | 8/2008 | Larsen et al. |
| 2008/0200940 A1 | 8/2008 | Eichmann et al. |
| 2008/0228104 A1 | 9/2008 | Uber, III et al. |
| 2008/0255413 A1 | 10/2008 | Zemlok et al. |
| 2008/0281301 A1 | 11/2008 | Deboer et al. |
| 2008/0315829 A1 | 12/2008 | Jones et al. |
| 2009/0043797 A1 | 2/2009 | Dorie et al. |
| 2009/0076506 A1 | 3/2009 | Baker |
| 2009/0096430 A1 | 4/2009 | Van Der Linde et al. |
| 2009/0143799 A1 | 6/2009 | Smith et al. |

(56) References Cited

U.S. PATENT DOCUMENTS

| | | | |
|---|---|---|---|
| 2009/0143800 A1 | 6/2009 | Deville et al. |
| 2009/0253030 A1 | 10/2009 | Kooij |
| 2009/0281430 A1 | 11/2009 | Wilder |
| 2010/0021022 A1 | 1/2010 | Pittel et al. |
| 2010/0030218 A1 | 2/2010 | Prevost |
| 2010/0060231 A1 | 3/2010 | Trainor et al. |
| 2010/0106144 A1 | 4/2010 | Matsumura et al. |
| 2010/0106146 A1 | 4/2010 | Boitor et al. |
| 2010/0125172 A1 | 5/2010 | Jayaraj |
| 2010/0152610 A1 | 6/2010 | Parihar et al. |
| 2010/0201311 A1 | 8/2010 | Alexander et al. |
| 2010/0249665 A1 | 9/2010 | Roche |
| 2010/0268221 A1 | 10/2010 | Beller et al. |
| 2010/0274160 A1 | 10/2010 | Yachi et al. |
| 2011/0009694 A1 | 1/2011 | Schultz et al. |
| 2011/0074336 A1 | 3/2011 | Miller |
| 2011/0077514 A1 | 3/2011 | Ulric et al. |
| 2011/0080134 A1 | 4/2011 | Miller |
| 2011/0221398 A1 | 9/2011 | Ferber |
| 2012/0111591 A1 | 5/2012 | Shelton, IV et al. |
| 2012/0116260 A1 | 5/2012 | Johnson et al. |
| 2012/0116261 A1 | 5/2012 | Mumaw et al. |
| 2012/0116262 A1 | 5/2012 | Houser et al. |
| 2012/0116265 A1 | 5/2012 | Houser et al. |
| 2012/0116266 A1 | 5/2012 | Houser et al. |
| 2012/0116381 A1 | 5/2012 | Houser et al. |
| 2012/0179036 A1 | 7/2012 | Patrick et al. |
| 2012/0292367 A1 | 11/2012 | Morgan et al. |
| 2012/0305427 A1 | 12/2012 | Felder et al. |
| 2013/0085330 A1 | 4/2013 | Ramamurthy et al. |
| 2013/0090528 A1 | 4/2013 | Ramamurthy et al. |
| 2013/0118733 A1 | 5/2013 | Kumar |
| 2014/0088379 A1 | 3/2014 | Bhamra et al. |
| 2015/0305763 A1 | 10/2015 | Houser et al. |
| 2016/0121143 A1 | 5/2016 | Mumaw et al. |
| 2016/0206900 A1 | 7/2016 | Haberstich et al. |
| 2016/0329614 A1 | 11/2016 | Madan et al. |
| 2016/0338760 A1 | 11/2016 | Houser et al. |

FOREIGN PATENT DOCUMENTS

| | | |
|---|---|---|
| EP | 0897696 A1 | 2/1999 |
| EP | 0947167 A1 | 10/1999 |
| EP | 1330991 A1 | 7/2003 |
| EP | 1525853 A2 | 4/2005 |
| EP | 1535585 A2 | 6/2005 |
| EP | 1684396 A2 | 7/2006 |
| EP | 1721576 A1 | 11/2006 |
| EP | 1743592 A1 | 1/2007 |
| EP | 1818021 A1 | 8/2007 |
| EP | 1839599 | 10/2007 |
| EP | 1868275 A2 | 12/2007 |
| EP | 1886637 A1 | 2/2008 |
| EP | 1263341 B1 | 6/2008 |
| EP | 1943976 A2 | 7/2008 |
| EP | 1970014 | 9/2008 |
| EP | 1997439 A2 | 12/2008 |
| EP | 2027819 A1 | 2/2009 |
| EP | 2090256 A2 | 8/2009 |
| EP | 2105104 A2 | 9/2009 |
| EP | 2165560 A2 | 3/2010 |
| EP | 2218409 A1 | 8/2010 |
| EP | 2243439 A1 | 10/2010 |
| EP | 2345454 A1 | 7/2011 |
| GB | 2425874 | 11/2006 |
| GB | 2440566 A | 2/2008 |
| JP | H 10-118090 A | 5/1998 |
| JP | 2002-186627 A | 7/2002 |
| JP | 4602681 | 10/2005 |
| JP | 4836148 | 4/2010 |
| WO | WO 1997/024072 | 7/1997 |
| WO | WO 2000/065682 | 2/2000 |
| WO | WO 2003/013374 | 2/2003 |
| WO | WO 2003/020139 | 3/2003 |
| WO | WO 2004/113991 | 12/2004 |
| WO | WO 2005/079915 | 9/2005 |
| WO | WO 2006/023266 | 3/2006 |
| WO | WO 2007/004515 | 1/2007 |
| WO | WO 2007/024983 | 3/2007 |
| WO | WO 2007/090025 | 8/2007 |
| WO | WO 2007/137115 | 11/2007 |
| WO | WO 2007/137304 | 11/2007 |
| WO | WO 2008/071898 | 6/2008 |
| WO | WO 2008/102154 | 8/2008 |
| WO | WO 2008/107902 | 9/2008 |
| WO | WO 2008/131357 | 10/2008 |
| WO | WO 2009/018409 | 2/2009 |
| WO | WO 2009/046394 | 4/2009 |
| WO | WO 2009/070780 | 6/2009 |
| WO | WO 2009/073608 | 6/2009 |
| WO | WO 2010/030850 | 3/2010 |
| WO | WO 2010/096174 | 8/2010 |
| WO | WO 2011/059785 | 5/2011 |
| WO | WO 2011/089270 | 7/2011 |

OTHER PUBLICATIONS

Indian Office Action, Examination Report, dated Aug. 7, 2019 for Application No. 3971/DELNP/2013, 8 pgs.
Indian Office Action, Examination Report, dated Aug. 16, 2019 for Application No. 3972/DELNP/2013, 5 pgs.
Indian Office Action, Examination Report, dated Dec. 5, 2019 for Application No. 3972/DELNP/2013, 8 pgs.
Dietz, T. et al., Partially Implantable Vibrating Ossicular Prosthesis, Transducers'97, vol. 1, International Conference on Solid State Sensors and Actuators, (Jun. 16-19, 1997) pp. 433-436 (Abstract).
"System 6 Aseptic Battery System," Snyker (2006) pp. 1-2.
Australian First Examination Report dated Jun. 11, 2015 for App. No. 2011323281.
Chinese First Office Action dated Apr. 16, 2015 for App. No. CN 201180063919X.
Chinese First Office Action dated Jun. 1, 2015 for App No. CN 2011800640981.
EP Communication dated Feb. 19, 2014 for Application No. EP 11781972.2.
International Search Report and Written Opinion dated Jan. 26, 2012 for Application No. PCT/US2011/059212.
International Preliminary Report on Patentability dated May 7, 2013 for Application No. PCT/US2011/059212.
Communication from International Searching Authority dated Jan. 24, 2012 for Application No. PCT/US2011/059215.
International Search Report dated Apr. 4, 2012 for Application No. PCT/US2011/059215.
International Preliminary Report on Patentability dated May 8, 2013 for Application No. PCT/US2011/059215.
International Search Report dated Feb. 13, 2012for Application No. PCT/US2011/059217.
International Preliminary Report on Patentability dated May 7, 2013 for Application No. PCT/US2011/059217.
International Search Report dated Jun. 12, 2012 for Application No. PCT/US2011/059218.
International Preliminary Report on Patentability dated May 7, 2013 for Application No. PCT/US2011/059218.
International Search Report dated Jan. 26, 2012 for Application No. PCT/US11/059220.
International Preliminary Report on Patentability dated May 7, 2013 for Application No. PCT/US2011/059220.
Communication from International Searching Authority dated Feb. 2, 2012for Application No. PCT/US2011/059222.
International Search Report dated Apr. 18, 2012 for Application No. PCT/US2011/059222.
International Preliminary Report on Patentability dated May 7, 2013 for Application No. PCT/US2011/059222.
International Search Report dated Feb. 1, 2012 for Application No. PCT/US11/059223.
International Preliminary Report on Patentability dated May 7, 2013 for Application No. PCT/US2011/059223.
International Search Report dated Jan. 12, 2012 for Application No. PCT/US11/059226.

(56) References Cited

OTHER PUBLICATIONS

International Preliminary Report on Patentability dated May 7, 2013 for Application No. PCT/US2011/059226.
International Search Report dated Mar. 15, 2012 for Application No. PCT/US2011/059338.
International Preliminary Report on Patentability dated May 7, 2013 for Application No. PCT/US2011/059338.
International Search Report dated Feb. 7, 2012 for Application No. PCT/US2011/059351.
International Preliminary Report on Patentability dated May 7, 2013 for Application No. PCT/US2011/059351.
International Search Report dated Feb. 2, 2012for Application No. PCT/US2011/059354.
International Preliminary Report on Patentability dated May 7, 2013 for Application No. PCT/US2011/059354.
International Search Report dated May 29, 2012 for Application No. PCT/US11/059358.
International Preliminary Report on Patentability dated May 7, 2013 for Application No. PCT/US2011/059358.
Communication from International Searching Authority dated Feb. 6, 2012for Application No. PCT/US2011/059362.
International Search Report dated Mar. 22, 2012for Application No. PCT/US2011/059362.
International Preliminary Report on Patentability dated May 7, 2013 for Application No. PCT/US2011/059362.
International Search Report dated Jun. 4, 2012 for Application No. PCT/US2011/059365.
International Preliminary Report on Patentability dated May 8, 2013 for Application No. PCT/US2011/059365.
International Search Report dated Feb. 23, 2012 for Application No. PCT/US2011/059371.
International Preliminary Report on Patentability dated May 7, 2013 for Application No. PCT/US2011/059371.
Communication from International Searching Authority dated Feb. 2, 2012 for Application No. PCT/US2011/059378.
International Search Report dated May 24, 2012 for Application No. PCT/US2011/059378.
International Search Report and Written Opinion dated Feb. 2, 2012 for Application No. PCT/US2011/059378.
International Preliminary Report on Patentability dated May 7, 2013 for Application No. PCT/US2011/059378.
International Search Report dated Apr. 11, 2012 for Application No. PCT/US2011/059381.
International Search Report and Written Opinion dated Jul. 6, 2012 for Application No. PCT/US2011/059381.
International Preliminary Report on Patentability dated May 8, 2013 for Application No. PCT/US2011/059381.
Japanese Office Action, Notification of Reasons for Refusal, dated Sep. 8, 2015 for App. No. 2013-537830.
Japanese Office Action, Notification of Reasons for Refusal, dated Aug. 25, 2015 for App. No. 2013-537831.
Office Action Non-Final dated Aug. 6, 2013 for U.S. Appl. No. 13/151,471.
Notice of Allowance dated Dec. 6, 2013 for U.S. Appl. No. 13/151,471.
Office Action Non-Final dated Mar. 28, 2014 for U.S. Appl. No. 13/151,471.
U.S. Office Action, Notice of Allowance, dated Aug. 19, 2014 for U.S. Appl. No. 13/151,471.
U.S. Office Action, Notice of Allowance, dated Nov. 21, 2014 for U.S. Appl. No. 13/151,471.
Restriction Requirement dated Dec. 11, 2012 for U.S. Appl. No. 13/151,481.
Office Action Non-Final dated Feb. 15, 2013 for U.S. Appl. No. 13/151,481.
Office Action Final dated Jun. 7, 2013 for U.S. Appl. No. 13/151,481.
U.S. Office Action, Non-Final, dated Aug. 14, 2014 for U.S. Appl. No. 13/151,481.
U.s. Office Action, Final, dated Apr. 1, 2015 for U.S. Appl. No. 13/151,481.
Restriction Requirement dated Jul. 5, 2013 for U.S. Appl. No. 13/151,488.
U.S. Office Action, Non-Final, dated Nov. 7, 2014 for U.S. Appl. No. 13/151,488.
Office Action Non-Final dated Jun. 14, 2013 for U.S. Appl. No. 13/151,498.
Office Action Final dated Nov. 21, 2013 for U.S. Appl. No. 13/151,498.
Office Action Non Final dated Mar. 18, 2014 for U.S. Appl. No. 13/151,498.
U.S. Office Action, Notice of Allowance, dated Aug. 6, 2014 for U.S. Appl. No. 13/151,498.
U.S. Office Action, Notice of Allowance, dated Nov. 21, 2014 for U.S. Appl. No. 13/151,498.
Office Action Non Final dated Jun. 18, 2014 for U.S. Appl. No. 13/151,503.
Office Action Non Final dated Nov. 6, 2014 for U.S. Appl. No. 13/151,503.
Restriction Requirement dated Mar. 13, 2013 for U.S. Appl. No. 13/151,509.
Restriction Requirement dated Jun. 24, 2013 for U.S. Appl. No. 13/151,509.
Office Action Non-Final dated Sep. 26, 2013 for U.S. Appl. No. 13/151,509.
Office Action Final dated Jan. 29, 2014 for U.S. Appl. No. 13/151,509.
Office Action Non-Final dated Jul. 9, 2014 for U.S. Appl. No. 13/151,509.
U.S. Office Action, Notice of Allowance, dated Oct. 28, 2014 for U.S. Appl. No. 13/151,509.
U.S. Offic Action, Notice of Allowance, dated Feb. 25, 2015 for U.S. Appl. No. 13/151,509.
Restriction Requirement dated Jun. 11, 2014 for U.S. Appl. No. 13/151,512.
U.S. Office Action, Notice of Allowance, dated Oct. 29, 2014 for U.S. Appl. No. 13/151,512.
U.S. Office Action, Notice of Allowance, dated Feb. 17, 2015 for U.S. Appl. No. 13/151,512.
U.S. Office Action, Restriction Requirement, dated Jul. 11, 2014 for U.S. Appl. No. 13/269,870.
U.S. Office Action, Non-Final, dated Jan. 5, 2015 for U.S. Appl. No. 13/269,870.
U.S. Office Action, Final, dated Aug. 14, 2015 for U.S. Appl. No. 13/269,870.
U.S. Office Action, Notice of Allowance, dated Apr. 14, 2016 for U.S. Appl. No. 13/269,870.
U.S. Office Action, Notice of Allowance, dated Jul. 22, 2016 for U.S. Appl. No. 13/269,870.
Restriction Requirement dated Feb. 28, 2013 for U.S. Appl. No. 13/270,667.
Office Action Non-Final dated Apr. 26, 2013 for U.S. Appl. No. 13/270,667.
Office Action Final dated Oct. 25, 2013 for U.S. Appl. No. 13/270,667.
U.S. Office Action, Non-Final, dated Jul. 29, 2014 for U.S. Appl. No. 13/270,667.
U.S. Office Action, Notice of Allowance, dated Dec. 17, 2014 for U.S. Appl. No. 13/270,667.
U.S. Office Action, Restriction Requirement, dated Jul. 9, 2014 for U.S. Appl. No. 13/270,684.
U.S. Office Action, Non-Final, dated Oct. 9, 2014 for U.S. Appl. No. 13/270,684.
U.S. Office Action, Final, dated Mar. 17, 2015 for U.S. Appl. No. 13/270,684.
U.S. Office Action, Notice of Allowance, dated Jul. 28, 2015 for U.S. Appl. No. 13/270,684.
U.S. Office Action, Notice of Allowance, dated Nov. 30, 2015 for U.S. Appl. No. 13/270,684.
U.S. Office Action, Restriction Requirement, dated Sep. 11, 2014 for U.S. Appl. No. 13/270,701.
U.S. Office Action, Non-Final, dated Dec. 16, 2014 for U.S. Appl. No. 13/270,701.
Office Action Non-Final dated Nov. 21, 2013 for U.S. Appl. No. 13/271,352.

(56) References Cited

OTHER PUBLICATIONS

U.S. Office Action, Restriction Requirement, dated Sep. 25, 2014 for U.S. Appl. No. 13/271,352.
U.S. Office Action, Non-Final, dated Mar. 26, 2015 for U.S. Appl. No. 13/271,352.
U.S. Office Action, Final, dated Jul. 15, 2015 for U.S. Appl. No. 13/271,352.
U.S. Office Action, Notice of Allowance, dated Feb. 19, 2016 for U.S. Appl. No. 13/271,352.
U.S. Office Action, Non-Final, dated Jul. 14, 2015 for U.S. Appl. No. 13/271,364.
U.S. Office Action, Notice of Allowance, dated Apr. 7, 2016 for U.S. Appl. No. 13/271,364.
U.S. Office Action, Notice of Allowance, dated Dec. 18, 2015 for U.S. Appl. No. 13/271,364.
U.S. Office Action, Restriction Requirement, dated Oct. 2, 2013 for U.S. Appl. No. 13/274,480.
Office Action Non-Final dated Feb. 14, 2014 for U.S. Appl. No. 13/274,480.
U.S. Office Action, Final, dated Jul. 17, 2014 for U.S. Appl. No. 13/274,480.
U.S. Office Action, Restriction Requirement, dated Dec. 9, 2013 for U.S. Appl. No. 13/274,496.
U.S. Office Action, Non-Final, dated Feb. 6, 2014 for U.S. Appl. No. 13/274,496.
U.S. Office Action, Final, dated May 15, 2014 for U.S. Appl. No. 13/274,496.
U.S. Office Action, Final, dated Aug. 22, 2014 for U.S. Appl. No. 13/274,496.
U.S. Office Action, Non-Final, dated Apr. 2, 2015 for U.S. Appl. No. 13/274,496.
Restriction Requirement dated Mar. 28, 2014 for U.S. Appl. No. 13/274,507.
Office Action Non-Final dated Jun. 19, 2014 for U.S. Appl. No. 13/274,507.
U.S. Office Action, Non-Final, dated Jul. 22, 2015 for U.S. Appl. No. 13/274,507.
U.S. Office Action, Final, dated Dec. 8, 2015 for U.S. Appl. No. 13/274,507.
Office Action Non-Final dated Dec. 21, 2012 for U.S. Appl. No. 13/274,516.
Office Action Final dated Aug. 16, 2013 for U.S. Appl. No. 13/274,516.
Office Action Non-Final dated Dec. 6, 2013 for U.S. Appl. No. 13/274,516.
U.S. Office Action, Final, dated Jun. 12, 2014 for U.S. Appl. No. 13/274,516.
U.S. Office Action, Non-Final, dated Oct. 8, 2014 for U.S. Appl. No. 13/274,516.
U.S. Office Action, Final, dated May 8, 2015 for U.S. Appl. No. 13/274,516.
U.S. Office Action, Notice of Allowance, dated Sep. 24, 2015 for U.S. Appl. No. 13/274,516.
Restriction Requirement dated Feb. 25, 2013 for U.S. Appl. No. 13/274,540.
Office Action Non-Final dated Apr. 30, 2013 for U.S. Appl. No. 13/274,540.
Office Action Final dated Oct. 25, 2013 for U.S. Appl. No. 13/274,540.
U.S. Office Action, Non-Final, dated Aug. 26, 2014 for U.S. Appl. No. 13/274,540.
U.S. Office Action, Notice of Allowance, dated Jan. 21, 2015 for U.S. Appl. No. 13/274,540.
Office Action Non-Final dated Apr. 1, 2013 for U.S. Appl. No. 13/274,805.
Office Action Final dated Sep. 12, 2013 for U.S. Appl. No. 13/274,805.
U.S. Office Action, Non-Final, dated Aug. 14, 2014 for U.S. Appl. No. 13/274,805.
U.S. Office Action, Notice of Allowance, dated Nov. 28, 2014 for U.S. Appl. No. 13/274,805.
U.S. Office Action, Notice of Allowance, dated Jan. 21, 2015 for U.S. Appl. No. 13/274,805.
Restriction Requirement dated Apr. 29, 2013 for U.S. Appl. No. 13/274,830.
Office Action Non-Final dated Jun. 14, 2013 for U.S. Appl. No. 13/274,830.
Office Action Final dated Nov. 26, 2013 for U.S. Appl. No. 13/274,830.
U.S. Office Action, Non-Final, dated Oct. 22, 2014 for U.S. Appl. No. 13/274,830.
U.S. Office Action, Notice of Allowance, dated Mar. 23, 2015 for U.S. Appl. No. 13/274,830.
Restriction Requirement dated Apr. 4, 2013 for U.S. Appl. No. 13/275,495.
Office Action Non-Final dated May 31, 2013 for U.S. Appl. No. 13/275,495.
Office Action Final dated Dec. 5, 2013 for U.S. Appl. No. 13/275,495.
U.S. Office Action, Non-Final, dated Feb. 25, 2015 for U.S. Appl. No. 13/275,495.
Office Action Non-Final dated Jan. 6, 2014 for U.S. Appl. No. 13/275,514.
U.S. Office Action, Non-Final, dated Sep. 9, 2014 for U.S. Appl. No. 13/275,514.
Office Action Non-Final dated May 17, 2013 for U.S. Appl. No. 13/275,547.
Office Action Final dated Feb. 28, 2014 for U.S. Appl. No. 13/275,547.
U.S. Office Action, Non-Final, dated Aug. 20, 2014 for U.S. Appl. No. 13/275,547.
U.S. Office Action, Final, dated Mar. 10, 2015 for U.S. Appl. No. 13/275,547.
Office Action Non-Final dated Feb. 1, 2013 for U.S. Appl. No. 13/275,563.
Office Action Final dated Aug. 29, 2013 for U.S. Appl. No. 13/275,563.
U.S. Office Action, Non-Final, dated Oct. 23, 2014 for U.S. Appl. No. 13/275,563.
Restriction Requirement dated Feb. 6, 2013 for U.S. Appl. No. 13/276,660.
Office Action Non-Final dated Jun. 3, 2013 for U.S. Appl. No. 13/246,660.
U.S. Office Action, Restriction Requirement, dated Jul. 9, 2014 for U.S. Appl. No. 13/276,660.
Office Action Non-Final dated Dec. 21, 2012 for U.S. Appl. No. 13/276,673.
Office Action Non-Final dated Aug. 19, 2013 for U.S. Appl. No. 13/276,673.
Office Action Final dated Mar. 21, 2014 for U.S. Appl. No. 13/276,673.
U.S. Office Action, Non-Final, dated Aug. 14, 2014 for U.S. Appl. No. 13/276,673.
U.S. Office Action, Final, dated Mar. 13, 2015 for U.S. Appl. No. 13/276,673.
Restriction Requirement dated Feb. 6, 2013 for U.S. Appl. No. 13/276,687.
Office Action Non-Final dated Jun. 12, 2013 for U.S. Appl. No. 13/276,687.
Notice of Allowance dated Nov. 12, 2013 for U.S. Appl. No. 13/276,687.
Notice of Allowance dated Jun. 2, 2014 for U.S. Appl. No. 13/276,687.
U.S. Office Action, Notice of Allowance, dated Sep. 12, 2014 for U.S. Appl. No. 13/276,687.
U.S. Office Action, Notice of Allowance, dated Dec. 23, 2014 for U.S. Appl. No. 13/276,687.
Restriction Requirement dated Feb. 21, 2013 for U.S. Appl. No. 13/276,707.
Office Action Non-Final dated May 6, 2013 for U.S. Appl. No. 13/276,707.
Office Action Final dated Sep. 27, 2013 for U.S. Appl. No. 13/276,707.
U.S. Office Action, Non-Final, dated Jan. 29, 2015 for U.S. Appl. No. 13/276,707.
Restriction Requirement dated Feb. 6, 2013 for U.S. Appl. No. 13/276,725.

(56) References Cited

OTHER PUBLICATIONS

U.S. Office Action, Non-Final, dated Aug. 20, 2014 for U.S. Appl. No. 13/276,725.
U.S. Office Action, Notice of Allowance, dated Mar. 13, 2015 for U.S. Appl. No. 13/276,725.
Restriction Requirement dated Dec. 21, 2012 for U.S. Appl. No. 13/276,745.
Office Action Non-Final dated Apr. 30, 2013 for U.S. Appl. No. 13/276,745.
Office Action Final dated Nov. 8, 2013 for U.S. Appl. No. 13/276,745.
Office Action Non-Final dated Feb. 28, 2014 for U.S. Appl. No. 13/276,745.
U.S. Office Action, Notice of Allowance, dated Oct. 7, 2014 for U.S. Appl. No. 13/276,745.
U.S. Office Action, Notice of Allowance, dated Dec. 19, 2014 for U.S. Appl. No. 13/276,745.
U.S. Office Action, Restriction Requirement, dated Sep. 24, 2014 for U.S. Appl. No. 13/277,328.
U.S. Office Action, Non-Final, dated Dec. 8, 2014 for U.S. Appl. No. 13/277,328.
U.S. Office Action, Final, dated Mar. 24, 2015 for U.S. Appl. No. 13/277,328.
U.S. Office Action, Notice of Allowance, dated Jun. 1, 2015 for U.S. Appl. No. 13/277,328.
U.S. Office Action, Non-Final, dated Aug. 26, 2016 for U.S. Appl. No. 15/008,530.
U.S. Office Action, Notice of Allowance, dated Feb. 7, 2017 for U.S. Appl. No. 15/008,530.
U.S. Office Action, Notice of Allowance, dated Jun. 16, 2017 for U.S. Appl. No. 15/008,530.
U.S. Appl. No. 13/274,496.
U.S. Appl. No. 13/275,563.
U.S. Appl. No. 14/788,915.
European Examination Report dated May 18, 2018 for Application No. EP 11784882.0, 4 pgs.
Indian Office Action, Examination Report, dated Nov. 15, 2019 for Application No. 3967/DELNP/2013, 6 pgs.

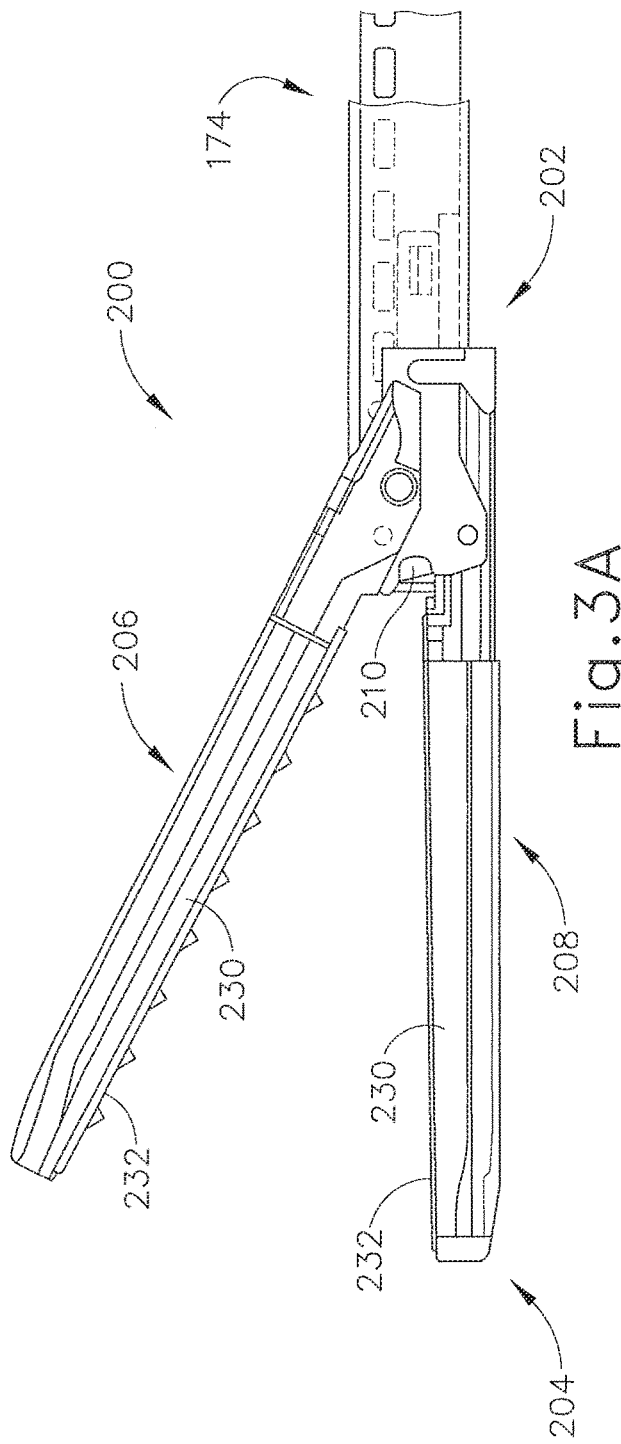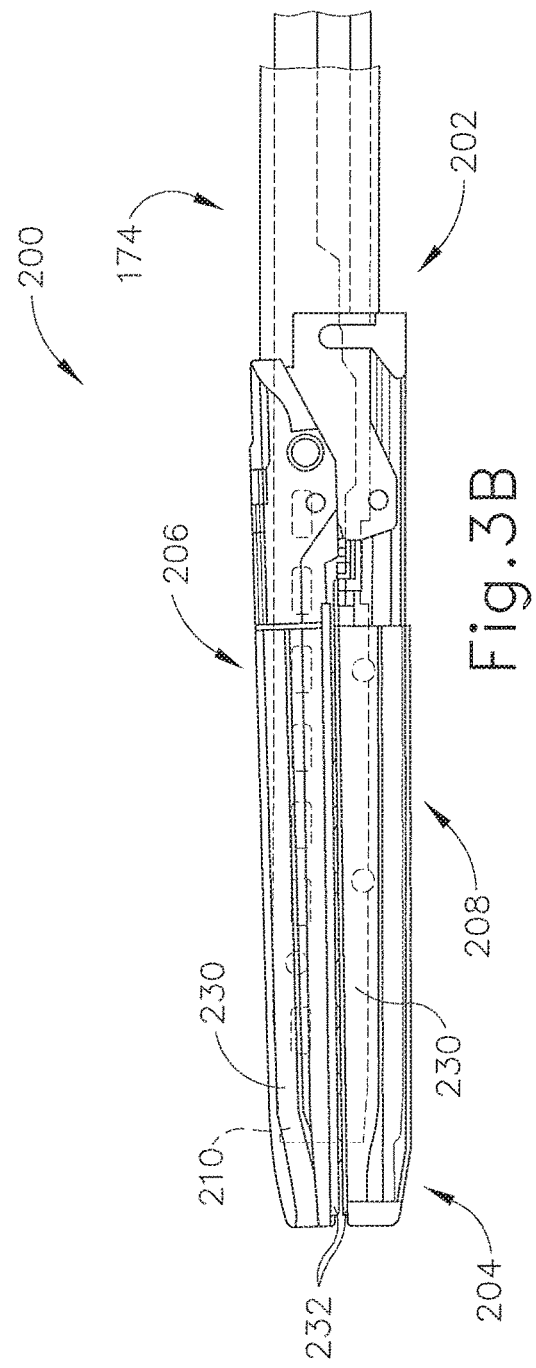

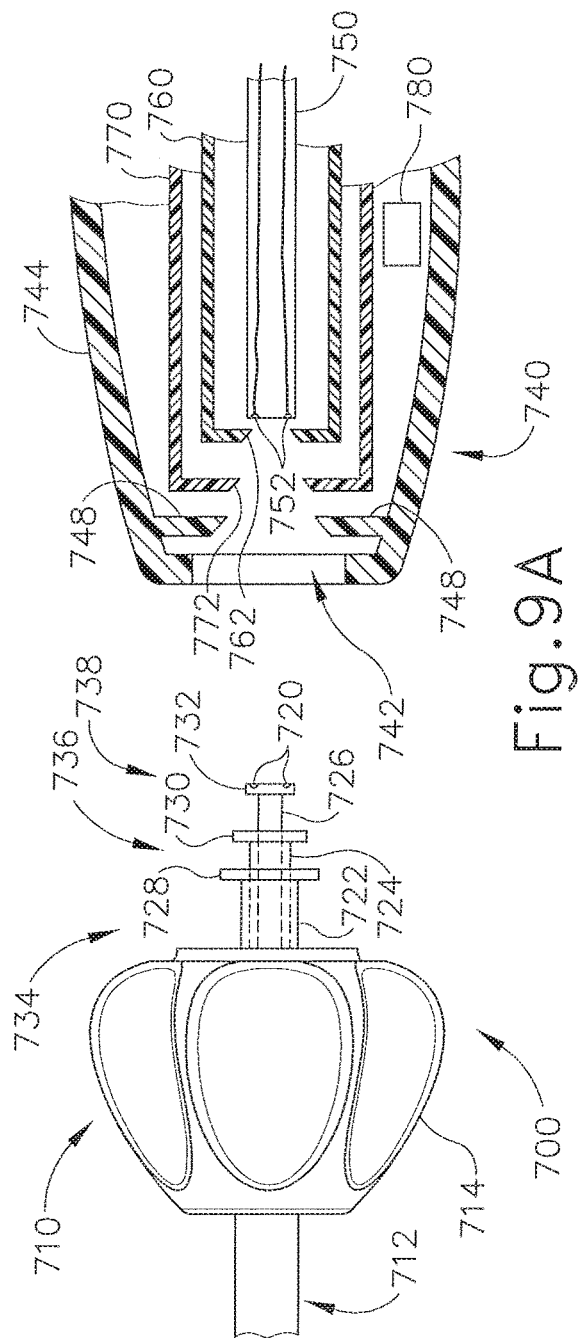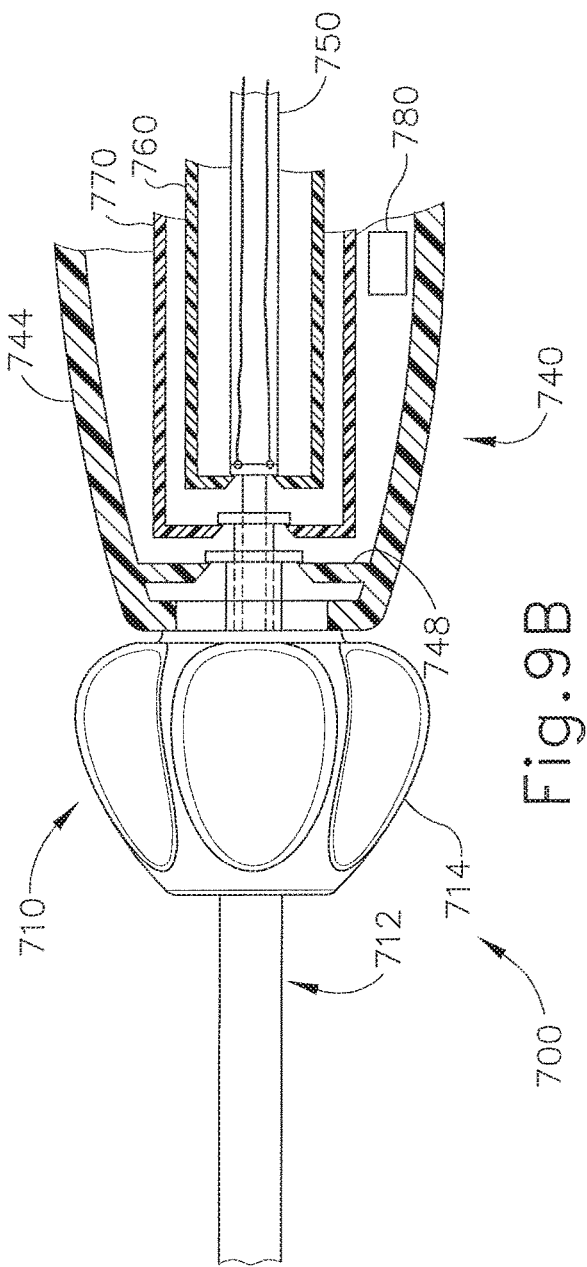

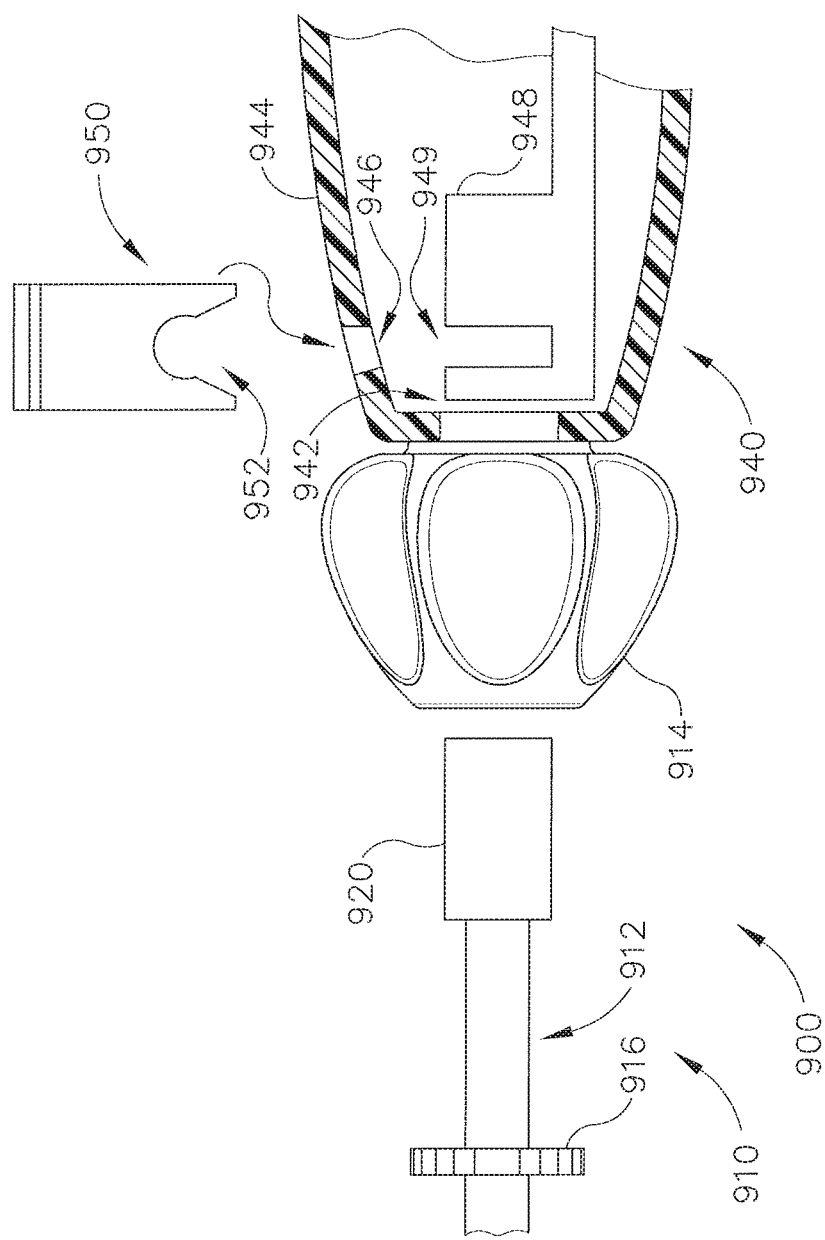

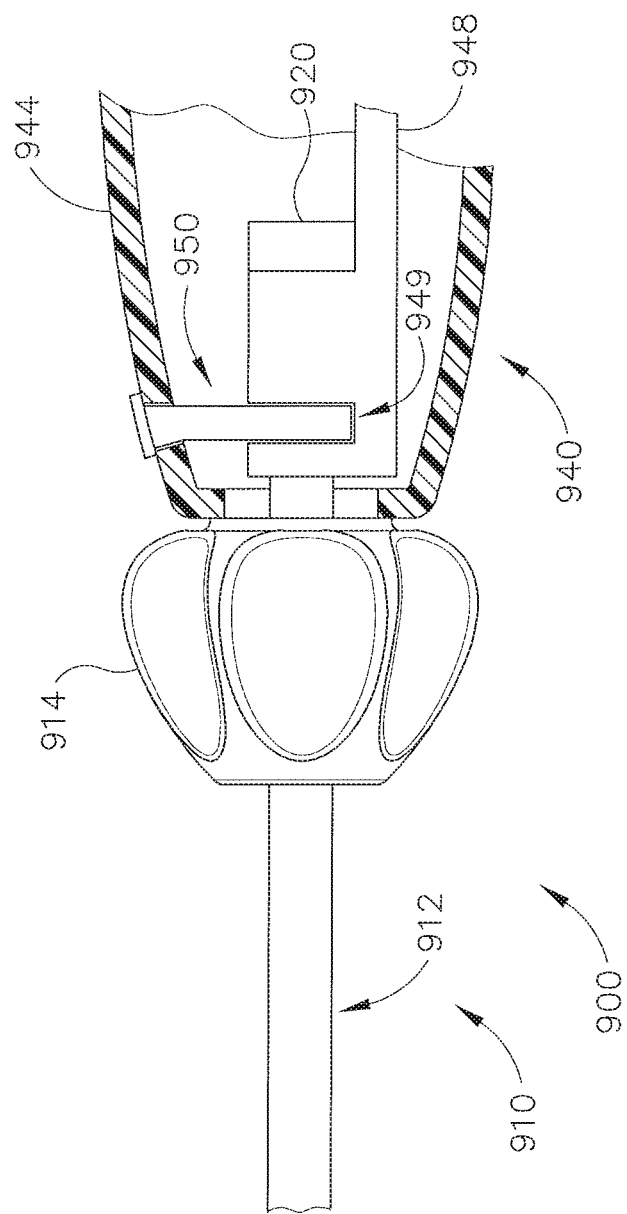

SURGICAL INSTRUMENT WITH MODULAR SHAFT AND END EFFECTOR

PRIORITY

This application is a continuation of U.S. application Ser. No. 15/342,218, entitled "Surgical Instrument with Modular Shaft and End Effector," filed Nov. 3, 2016 and issued as U.S. Pat. No. 10,376,304 on Aug. 13, 2019, which is a divisional of U.S. application Ser. No. 13/269,870, filed Oct. 10, 2011, and issued as U.S. Pat. No. 9,510,895 on Dec. 6, 2016.

U.S. application Ser. No. 13/269,870 claims priority to U.S. Provisional Application Ser. No. 61/410,603, filed Nov. 5, 2010, entitled "Energy-Based Surgical Instruments," the disclosure of which is incorporated by reference herein.

U.S. application Ser. No. 13/269,870 also claims priority to U.S. Provisional Application Ser. No. 61/487,846, filed May 19, 2011, entitled "Energy-Based Surgical Instruments," the disclosure of which is incorporated by reference herein.

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through a cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RE, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient.

Examples of endoscopic surgical instruments include those disclosed in U.S. Pat. No. 7,416,101 entitled "Motor-Driven Surgical Cutting and Fastening Instrument with Loading Force Feedback," issued Aug. 26, 2008, the disclosure of which is incorporated by reference herein; U.S. Pat. No. 7,738,971 entitled "Post-Sterilization Programming of Surgical Instruments," issued Jun. 15, 2010, the disclosure of which is incorporated by reference herein; U.S. Pub. No. 2006/0079874 entitled "Tissue Pad for Use with an Ultrasonic Surgical Instrument," published Apr. 13, 2006, now abandoned, the disclosure of which is incorporated by reference herein; U.S. Pub. No. 2007/0191713 entitled "Ultrasonic Device for Cutting and Coagulating," published Aug. 16, 2007, now abandoned, the disclosure of which is incorporated by reference herein; U.S. Pub. No. 2007/0282333 entitled "Ultrasonic Waveguide and Blade," published Dec. 6, 2007, now abandoned, the disclosure of which is incorporated by reference herein; U.S. Pub. No. 2008/0200940 entitled "Ultrasonic Device for Cutting and Coagulating," published Aug. 21, 2008, now abandoned, the disclosure of which is incorporated by reference herein; U.S. Pat. Pub. No. 2009/0143797, entitled "Cordless Hand-held Ultrasonic Cautery Cutting Device," published Jun. 4, 2009, issued as U.S. Pat. No. 8,419,757 on Apr. 6, 2013, the disclosure of which is incorporated by reference herein; U.S. Pub. No. 2009/0209990 entitled "Motorized Surgical Cutting and Fastening Instrument Having Handle Based Power Source," published Aug. 20, 2009, issued as U.S. Pat. No. 8,657,174 on Feb. 25, 2014, the disclosure of which is incorporated by reference herein; U.S. Pub. No. 2010/0069940 entitled "Ultrasonic Device for Fingertip Control," published Mar. 18, 2010, issued as U.S. Pat. No. 9,023,071 on May 5, 2015, the disclosure of which is incorporated by reference herein; and U.S. Pub. No. 2011/0015660, entitled "Rotating Transducer Mount for Ultrasonic Surgical Instruments," published Jan. 20, 2011, issued as U.S. Pat. No. 8,461,744 on Jun. 11, 2013 the disclosure of which is incorporated by reference herein. Similarly, various ways in which medical devices may be adapted to include a portable power source are disclosed in U.S. Provisional Application Ser. No. 61/410,603, filed Nov. 5, 2010, entitled "Energy-Based Surgical Instruments," the disclosure of which is incorporated by reference herein.

Additional examples endoscopic surgical instruments include are disclosed in U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,112,201 entitled "Electrosurgical Instrument and Method of Use," issued Sep. 26, 2006, the disclosure of which is incorporated by reference herein; U.S. Pat. No. 7,125,409, entitled "Electrosurgical Working End for Controlled Energy Delivery," issued Oct. 24, 2006, the disclosure of which is incorporated by reference herein; U.S. Pat. No. 7,169,146 entitled "Electrosurgical Probe and Method of Use," issued Jan. 30, 2007, the disclosure of which is incorporated by reference herein; U.S. Pat. No. 7,186,253, entitled "Electrosurgical Jaw Structure for Controlled Energy Delivery," issued Mar. 6, 2007, the disclosure of which is incorporated by reference herein; U.S. Pat. No. 7,189,233, entitled "Electrosurgical Instrument," issued Mar. 13, 2007, the disclosure of which is incorporated by reference herein; U.S. Pat. No. 7,220,951, entitled "Surgical Sealing Surfaces and Methods of Use," issued May 22, 2007, the disclosure of which is incorporated by reference herein; U.S. Pat. No. 7,309,849, entitled "Polymer Compositions Exhibiting a PTC Property and Methods of Fabrication," issued Dec. 18, 2007, the disclosure of which is incorporated by reference herein; U.S. Pat. No. 7,311,709, entitled "Electrosurgical Instrument and Method of Use," issued Dec. 25, 2007, the disclosure of which is incorporated by reference herein; U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein; U.S. Pub. No. 2011/0087218, entitled "Surgical Instrument Comprising First and Second Drive Systems Actuatable by a Common Trigger Mechanism," published Apr. 14, 2011, now U.S. Pat. No. 8,939,974, issued Jan. 27, 2015, the disclosure of which is incorporated by reference herein; and U.S. patent application Ser. No. 13/151,481, entitled "Motor Driven Electrosurgical Device with Mechanical and Electrical Feedback," filed Jun. 2, 2011, now U.S. Pat. No. 9,161,803, issued Oct. 20, 2015, the disclosure of which is incorporated by reference herein.

In addition, the surgical instruments may be used, or adapted for use, in robotic-assisted surgery settings such as that disclosed in U.S. Pat. No. 6,783,524, entitled "Robotic Surgical Tool with Ultrasound Cauterizing and Cutting Instrument," issued Aug. 31, 2004.

While several systems and methods have been made and used for surgical instruments, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 3A depicts a side elevation view of an end effector of the surgical instrument of FIG. 2 shown in an open position;

FIG. 3B depicts a side elevation view of the end effector of FIG. 3A shown in a closed position;

FIG. 9A depicts a side elevation view of a fifth exemplary coupling mechanism with a portion of a handle assembly removed to show the interior thereof and showing a decoupled end effector assembly;

FIG. 9B depicts a side elevation view of the coupling mechanism of FIG. 9A showing the end effector assembly coupled to the handle assembly;

FIG. 11A depicts a side elevation view of a seventh exemplary coupling mechanism with a portion of a handle assembly removed to show the interior thereof and showing a decoupled end effector assembly;

FIG. 11B depicts a side elevation view of the coupling mechanism of FIG. 11A showing the end effector assembly coupled to the handle assembly;

Figure 1:
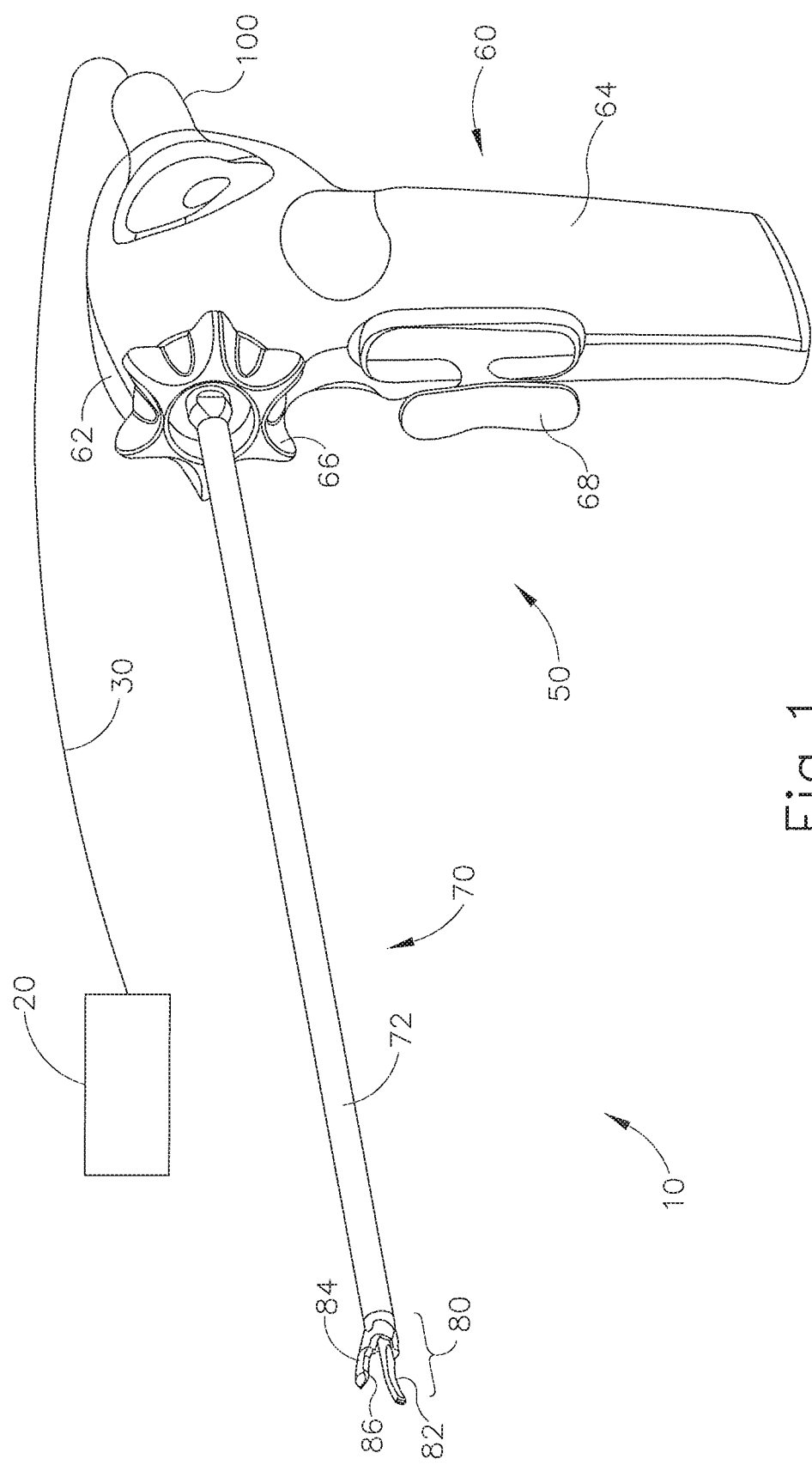
FIG. 1 depicts a perspective view of an exemplary surgical system comprising a surgical instrument and a generator.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It should be understood that the teachings below may be readily applied to any of the references that are cited herein. Various suitable ways in which the below teachings may be combined with the references cited herein will be apparent to those of ordinary skill in the art.

I. Overview of Exemplary Ultrasonic Surgical System

FIG. 1 shows an exemplary ultrasonic surgical system (10) comprising an ultrasonic surgical instrument (50), a generator (20), and a cable (30) operable to couple generator (20) to surgical instrument (50). A suitable generator (20) is the GEN 300 sold by Ethicon Endo-Surgery, Inc. of Cincinnati, Ohio. By way of example only, generator (20) may be constructed in accordance with the teachings of U.S. Pub. No. 2011/0087212, entitled "Surgical Generator for Ultrasonic and Electrosurgical Devices," published Apr. 14, 2011, issued as U.S. Pat. No. 8,986,302 on Mar. 24, 2015, the disclosure of which is incorporated by reference herein. It should be noted that surgical instrument (50) will be described in reference to an ultrasonic surgical instrument; however, the technology described below may be used with a variety of surgical instruments, including, but not limited to, endocutters, graspers, cutters, staplers, clip appliers, access devices, drug/gene therapy delivery devices, and energy delivery devices using ultrasound, RF, laser, etc., and/or any combination thereof as will be apparent to one of ordinary skill in the art in view of the teachings herein. Moreover, while the present example will be described in reference to a cable-connected surgical instrument (50), it should be understood that surgical instrument (50) may be adapted for cordless operation, such as that disclosed in U.S. Pat. Pub. No. 2009/0143797, entitled "Cordless Hand-held Ultrasonic Cautery Cutting Device," published Jun. 4, 2009, issued as U.S. Pat. No. 8,419,757 on Apr. 16, 2013, the disclosure of which is incorporated by reference herein. Furthermore, surgical device (50) may also be used, or adapted for use, in robotic-assisted surgery settings such as that disclosed in U.S. Pat. No. 6,783,524, entitled "Robotic Surgical Tool with Ultrasound Cauterizing and Cutting Instrument," issued Aug. 31, 2004.

Surgical instrument (50) of the present example includes a multi-piece handle assembly (60), an elongated transmission assembly (70), and a transducer (100). Transmission assembly (70) is coupled to multi-piece handle assembly (60) at a proximal end of transmission assembly (70) and extends distally from multi-piece handle assembly (60). In the present example transmission assembly (70) is configured to be an elongated, thin tubular assembly for endoscopic use, but it should be understood that transmission assembly (70) may alternatively be a short assembly, such as those disclosed in U.S. Pat. Pub. No. 2007/0282333, entitled "Ultrasonic Waveguide and Blade," published Dec. 6, 2007, now abandoned, and U.S. Pat. Pub. No. 2008/0200940, entitled "Ultrasonic Device for Cutting and Coagulating," published Aug. 21, 2008, now abandoned, the disclosures of which are incorporated by reference herein. Transmission assembly (70) of the present example comprises an outer sheath (72), an inner tubular actuating member (not shown), a waveguide (not shown), and an end effector (80) located on the distal end of transmission assembly (70). In the present example, end effector (80) comprises a blade (82) coupled to the waveguide, a clamp arm (84) operable to pivot at the proximal end of transmission assembly (70), and, optionally, one or more clamp pads (86) coupleable to clamp arm (84). It should also be understood that clamp arm (84) and associated features may be constructed and operable in accordance with at least some of the teachings of U.S. Pat. No. 5,980,510, entitled "Ultrasonic Clamp Coagulator Apparatus Having Improved Clamp Arm Pivot Mount," issued Nov. 9, 1999, the disclosure of which is incorporated by reference herein. The waveguide, which is adapted to transmit ultrasonic energy from a transducer (100) to blade (82), may be flexible, semi-flexible, or rigid. One merely exemplary ultrasonic transducer (100) is Model No. HP054, sold by Ethicon Endo-Surgery, Inc. of Cincinnati, Ohio. The waveguide may also be configured to amplify the mechanical vibrations transmitted through the waveguide to blade (82) as is well known in the art. The waveguide may further have features to control the gain of the longitudinal vibration along the waveguide and features to tune the waveguide to the resonant frequency of the system.

In the present example, the distal end of the blade (82) is disposed near an anti-node in order to tune the acoustic assembly to a preferred resonant frequency $f_o$ when the acoustic assembly is not loaded by tissue. When transducer (100) is energized, the distal end of blade (82) is configured to move longitudinally in the range of, for example, approximately 10 to 500 microns peak-to-peak, and preferably in the range of about 20 to about 200 microns at a predetermined vibratory frequency $f_o$ of, for example, 55.5 kHz. When transducer (100) of the present example is activated, these mechanical oscillations are transmitted through the waveguide to end effector (80). In the present example, blade (82), being coupled to the waveguide, oscillates at the ultrasonic frequency. Thus, when tissue is secured between blade (82) and clamp arm (84), the ultrasonic oscillation of blade (82) may simultaneously sever the tissue and denature the proteins in adjacent tissue cells, thereby providing a coagulative effect with relatively little thermal spread. An electrical current may also be provided through blade (82) and clamp arm (84) to also cauterize the tissue. While some configurations for transmission assembly (70) and transducer (100) have been described, still other suitable configurations for transmission assembly (70) and transducer (100) will be apparent to one or ordinary skill in the art in view of the teachings herein.

Multi-piece handle assembly (60) of the present example comprises a mating housing portion (62) and a lower portion (64). Mating housing portion (62) is configured to receive transducer (100) at a proximal end of mating housing portion (62) and to receive the proximal end of transmission assembly (70) at a distal end of mating housing portion (62). An aperture, described in more detail below, is provided on the distal end of mating housing portion (62) for insertion of various transmission assemblies (70). A rotation knob (66) is shown in the present example to rotate transmission assembly (70) and/or transducer (100), but it should be understood that rotation knob (66) is merely optional. Lower portion (64) of multi-piece handle assembly (60) includes a trigger (68) and is configured to be grasped by a user using a single hand. One merely exemplary alternative configuration for lower portion (64) is depicted in FIG. 1 of U.S. Pat. Pub. No. 2011/0015660, entitled "Rotating Transducer Mount for Ultrasonic Surgical Instruments," published Jan. 20, 2011, issued as U.S. Pat. No. 8,461,744 on Jun. 11, 2013 the disclosure of which is incorporated by reference herein. Toggle buttons (not shown) may be located on a distal surface of lower portion (64) and may be operable to activate transducer (100) at different operational levels using generator (20). For instance, a first toggle button may activate transducer (100) at a maximum energy level while a second toggle button may activate transducer (100) at a minimum, non-zero energy level. Of course, the toggle buttons may be configured for energy levels other than a maximum and/or minimum energy level as will be apparent to one of ordinary skill in the art in view of the teachings herein. Moreover, the toggle buttons may be located anywhere else on multi-piece handle assembly (60), on transducer (100), and/or remote from surgical instrument (50), and any number of toggle buttons may be provided. While multi-piece handle assembly (60) has been described in reference to two distinct portions (62, 64), it should be understood that multi-piece handle assembly (60) may be a unitary assembly with both portions (62, 64) combined. Multi-piece handle assembly (60) may alternatively be divided into multiple discrete components, such as a separate trigger portion (operable either by a user's hand or foot) and a separate mating housing portion (62). The trigger portion may be operable to activate transducer (100) and may be remote from mating housing portion (62). Multi-piece handle assembly (60) may be constructed from a durable plastic (such as polycarbonate or a liquid crystal polymer), ceramics and/or metals or any other suitable material as will be apparent to one of ordinary skill in the art in view of the teachings herein. Still other configurations for multi-piece handle assembly (60) will be apparent to those of ordinary skill in the art in view of the teachings herein. For instance, instrument (50) may be operated as part of a robotic system. Other configurations for multi-piece handle assembly (60) will also be apparent to those of ordinary skill in the art in view of the teachings herein. By way of example only, surgical instrument (50) may be constructed in accordance with at least some of the teachings of U.S. Pat. No. 5,980,510; U.S. Pat. Pub. No. 2006/0079874 now abandoned; U.S. Pat. Pub. No. 2007/0191713, now abandoned; U.S. Pat. Pub. No. 2007/0282333, now abandoned; U.S. Pat. Pub. No. 2008/0200940, now abandoned; U.S. Pat. Pub. No. 2011/0015660, issued as U.S. Pat. No. 8,461,744 on Jun. 11, 2013; U.S. Pat. No. 6,500,176; U.S. Pat. Pub. No. 2011/0087218, issued as U.S. Pat. No. 8,939,974, on Jan. 27, 2015; and/or U.S. Pat. Pub. No. 2009/0143797, issued as U.S. Pat. No. 8,419,757 on Apr. 16, 2013.

Additional optional configurations and features for surgical instrument (50) are described in U.S. patent application Ser. No. 13/269,899, entitled "Ultrasonic Surgical Instrument with Modular End Effector," filed on even date herewith, issued as U.S. Pat. No. 9,050,125 on Jun. 9, 2015, the disclosure of which is incorporated by reference herein.

II. Overview of Exemplary Radiofrequency (RE) Surgical Instrument

Figure 2:
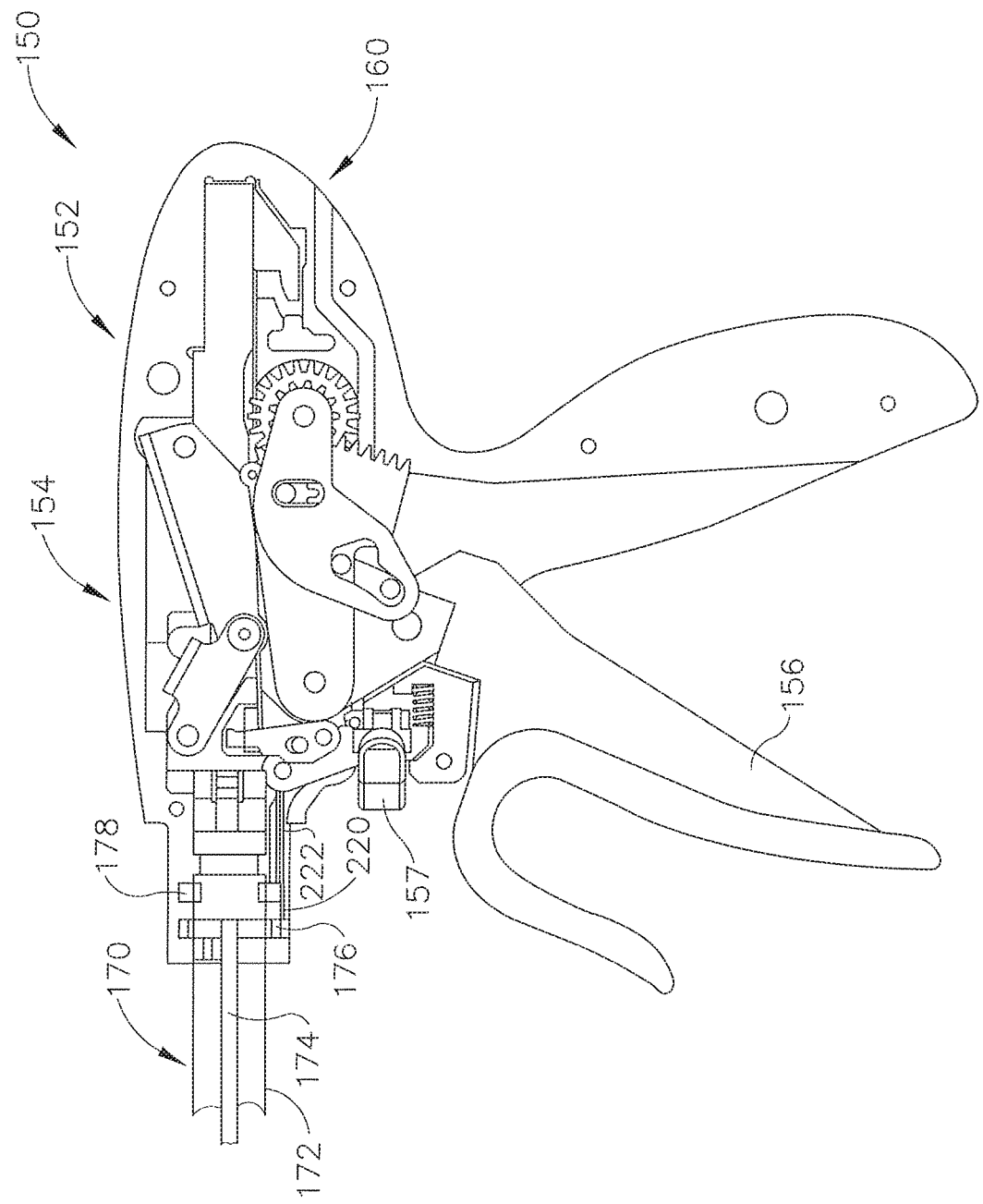
FIG. 2 depicts a side cross-sectional view of a handle of another exemplary surgical instrument.

While some surgical instruments are adapted to use ultrasonic energy to operate on tissue, other surgical instruments, such as surgical instrument (150), shown in FIGS. 2-3B, can be configured to supply energy, such as electrical energy and/or heat energy, to the tissue of a patient. Surgical instrument (150) includes a handle assembly (152), a transmission assembly (170), and an end effector (200) (shown in FIGS. 3A-3B) coupled to a distal end of transmission assembly (170). As described in greater detail below, handle assembly (152) may include one or more switches and/or triggers to supply electrical energy to end effector (200) and/or advance a knife or cutting member (210) (also shown in FIGS. 3A-3B) within end effector (200) to transect the tissue positioned within end effector (200).

A. Exemplary Handle Assembly

Referring to FIG. 2, handle assembly (152) comprises one or more electrical inputs (160) that are operably coupled with a power supply (not shown), such as generator (20) and/or any other power supply, including, for example, a power supply contained within handle assembly (152). A transmission assembly (170) extends distally from handle assembly (152) and includes end effector (200) coupled to a distal end of transmission assembly (170). The power supply provides an electrical current to surgical instrument (150), and the power supply may be operable to control the magnitude, duration, wave form, and/or frequency, of the current to provide a desired amount of energy to surgical instrument (150). Handle assembly (152) of the present example comprises a handle body (154) that is configured to support a switch or trigger (156) to electrically couple electrical input (160) with a first conductor (220) extending through transmission assembly (170) such that the current supplied to input (160) can be transmitted to end effector (200). As shown in FIG. 2, handle body (154) comprises two longitudinally halved portions that are assembled together to form handle body (154). As depicted in FIG. 2, one portion has been omitted to show some of the various internal components of handle assembly (152). In various embodiments, the halves of handle body (154) can be snap-fit, press-fit, welded, adhered together, and/or fastened to one another as will be apparent to one of ordinary skill in the art in view of the teachings herein. Further still, handle assembly (152) may be a unitary piece instead of two discrete halves. In yet another alternative, the portions may not be halves, but merely discrete coupleable components, such as a handle body (154) with a removable top and/or side portion. Still other configurations for handle body (154) will be apparent to one of ordinary skill in the art in view of the teachings herein.

First conductor (220) comprises a wire, such as insulated wire, that extends between trigger (156) and a first electrode (230), shown in FIG. 3A-3B in end effector (200), and also between trigger (156) and input (160). In the present example, first conductor (220) is coupled to a first electrode (230) in an upper jaw (206) and a first electrode (230) in a lower jaw (208), though it should be understood that first electrode (230) may be in only upper jaw (206) or in only lower jaw (208). A first slip ring (176) electrically couples a portion of first conductor (220) extending through transmission assembly (170) to a portion of first conductor (220) contained within handle assembly (152). Handle assembly (152) further comprises a second conductor (222) that is also electrically coupled to the power supply via input (160) and extends through transmission assembly (170) to end effector (200) to a second electrode (232). In the present example, second conductor (222) is coupled to second electrode (232) in upper jaw (206) and second electrode (232) in lower jaw (208), though it should be understood that second electrode (232) may be in only upper jaw (206) or in only lower jaw (208). Transmission assembly (170) comprises an outer sheath (172) that is coaxial to, and disposed about, a shaft (174) such that shaft (174) is contained within outer sheath (172). Second conductor (222) comprises a wire with an insulative plastic jacket or sheath to insulate second conductor (222) relative to first conductor (220), shaft (174), and/or first electrode (230). A second slip ring (178) is configured to electrically couple a portion of second conductor (222) extending through transmission assembly (170) to a portion of second conductor (222) contained within handle assembly (152). Slip rings (176, 178) of the present example comprise a circular, or an at least semi-circular, contact that is mounted to handle body (154) and which remains in contact with a corresponding circular, or an at least semi-circular, contact mounted to a portion of transmission assembly (170). Slip rings (176, 178) thus permit rotation of transmission assembly (170) relative to handle assembly (152) while still providing an electrical path for first and second conductors (220, 222) through transmission assembly (170).

Of course handle assembly (152) and surgical instrument (150) may include other configurations. For instance, handle assembly (152) and/or surgical instrument (150) may include a tissue cutting element and one or more elements that transmit bipolar RF energy to tissue (e.g., to coagulate or seal the tissue). An example of such a device is the ENSEAL® Tissue Sealing Device by Ethicon Endo-Surgery, Inc., of Cincinnati, Ohio. Further examples of such devices and related concepts are disclosed in U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,112,201, entitled "Electrosurgical Instrument and Method of Use," issued Sep. 26, 2006, the disclosure of which is incorporated by reference herein; U.S. Pat. No. 7,125,409, entitled "Electrosurgical Working End for Controlled Energy Delivery," issued Oct. 24, 2006, the disclosure of which is incorporated by reference herein; U.S. Pat. No. 7,169,146 entitled "Electrosurgical Probe and Method of Use," issued Jan. 30, 2007, the disclosure of which is incorporated by reference herein; U.S. Pat. No. 7,186,253, entitled "Electrosurgical Jaw Structure for Controlled Energy Delivery," issued Mar. 6, 2007, the disclosure of which is incorporated by reference herein; U.S. Pat. No. 7,189,233, entitled "Electrosurgical Instrument," issued Mar. 13, 2007, the disclosure of which is incorporated by reference herein; U.S. Pat. No. 7,220,951, entitled "Surgical Sealing Surfaces and Methods of Use," issued May 22, 2007, the disclosure of which is incorporated by reference herein; U.S. Pat. No. 7,309,849, entitled "Polymer Compositions Exhibiting a PTC Property and Methods of Fabrication," issued Dec. 18, 2007, the disclosure of which is incorporated by reference herein; U.S. Pat. No. 7,311,709, entitled "Electrosurgical Instrument and Method of Use," issued Dec. 25, 2007, the disclosure of which is incorporated by reference herein; U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein; U.S. Pub. No. 2011/0087218, entitled "Surgical Instrument Comprising First and Second Drive Systems Actuatable by a Common Trigger Mechanism," published Apr. 14, 2011, now U.S. Pat. No. 8,939,974, issued Jan. 27, 2015, the disclosure of which is incorporated by reference herein; and U.S. patent application Ser. No. 13/151,481, entitled "Motor Driven Electrosurgical Device with Mechanical and Electrical Feedback," filed Jun. 2, 2011, issued as U.S. Pat. No. 9,161,803 on Oct. 20, 2015, the disclosure of which is incorporated by reference herein.

B. Exemplary RF End Effector

Figure 4:
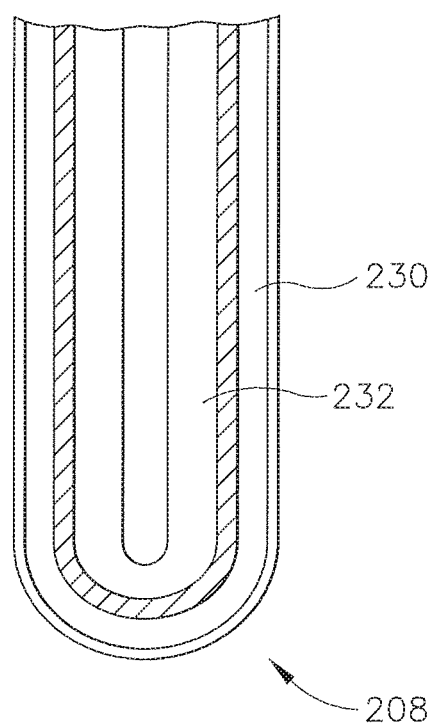
FIG. 4 depicts a top plan view of a lower jaw of the end effector of FIG. 3A.

End effector (200) of the present example comprises an upper jaw (206) and a lower jaw (208). Upper jaw (206) is pivotable relative to lower jaw (208) and is operable to clamp tissue between upper jaw (206) and lower jaw (208) via actuation of shaft (174). Actuation of shaft (174) may be accomplished via actuation of trigger (156), by a second trigger, by a button, by a motor, by a solenoid, and/or by any other suitable method. Both upper jaw (206) and lower jaw (208) of the present example include first electrode (230) which extends between a proximal end (202) and a distal end (204) of end effector (200), shown in FIGS. 3A-3B. As shown in FIG. 4, first electrode (230) of the present example comprises a first lateral portion extending along a first side of both upper jaw (206) and lower jaw (208), a second lateral portion extending along a second side of both upper jaw (206) and lower jaw (208), and a transverse end portion connecting the first lateral portion and the second lateral portion for both upper jaw (206) and lower jaw (208). Upper jaw (206) and lower jaw (208) of the present example further comprise second electrode (232) of a similar shape as first electrode (230), but insulated from first electrode (230) and inset from first electrode (230). In some versions, first electrode (230) may instead be inset of second electrode (232) for upper jaw (206) while second electrode (232) is inset of first electrode (230) for lower jaw (208) or vice versa. In other versions, upper jaw (206) includes only first electrode (230) and lower jaw (208) includes only second electrode (232), or vice versa. In still another configuration, second electrode (232) may be actuatable with cutting member (210). Both upper jaw (206) and lower jaw (208) include a longitudinal channel (not shown) configured to permit cutting member (210) to translate longitudinally therein. Still other configurations for end effector (200) are disclosed in U.S. Pat. Nos. 6,500,176; 7,112,201; 7,125,409; 7,169,146; 7,186,253; 7,189,233; 7,220,951; 7,309,849; 7,311,709; 7,354,440; 7,381,209; U.S. Pat. Pub. No. 2011/0087218, issued as U.S. Pat. No. 8,939,974 on Jan. 27, 2015; and/or U.S. patent application Ser. No. 13/151,481, entitled "Motor Driven Electrosurgical Device with Mechanical and Electrical Feedback," filed Jun. 2, 2011, issued as U.S. Pat. No. 9,161,803 on Oct. 20, 2015, the disclosures of which are incorporated by reference herein.

In the present example, trigger (156) (shown in FIG. 2) is operable to both clamp tissue between upper jaw (206) and lower jaw (208) and to selectively supply energy from the power supply to first electrode (230) via first conductor (220), though this is merely optional. In some versions, trigger (156) may be operable to clamp the tissue while a button selectively supplies energy from the power supply to first electrode (230) via first conductor (220). Second electrode (232) may remain constantly coupled to the power supply via second conductor (222) when power supply is coupled to electrical input (160) or, in one alternative, a second trigger and/or button may selectively supply power to second electrode (232). Accordingly, when trigger (156) is actuated, current flows from first electrode (230) to second electrode (232) to cauterize the tissue therebetween. This heat may denature the collagen within the tissue and, in co-operation with clamping pressure provided by jaws (206, 208) of end effector (200), the denatured collagen may form a seal within the tissue. In the present example, end effector (200) is configured to use bipolar RF energy to seal the tissue, though it should be understood that in other versions monopolar RF energy and/or thermal heating elements may be used. As an alternative to trigger (156) causing current to flow, a separate button (157) may be used to provide power to electrodes (230, 232). For instance, trigger (156) may be used simply to mechanically clamp jaws (206, 208) together; while button (157) sends a signal to a power source such as generator (20) to provide current to electrodes (230, 232). In addition or in the alternative, button (157) may provide a mechanical or electromechanical lockout to trigger (156), such that trigger (156) cannot be fully actuated unless button (157) is being depressed simultaneously. In addition or as an alternative to such functionality, trigger (156) may also provide a lockout to button (157).

In the present example, the first side of electrodes (230, 232) is configured to create a first seal within the tissue and the second side of electrodes (230, 232) is configured to create a second seal within the tissue. Of course other configurations may include multiple electrodes, and/or multiple electrode portions, that can create any suitable number of seals within the tissue. As the tissue is sealed on either end of the longitudinal channels of upper jaw (206) and lower jaw (208), cutting member (210) is actuated distally to sever the two sealed portions of tissue. In some versions, cutting member (210) may be actuated subsequent to the sealing of the tissue. In addition or in the alternative to the above. RF energy may be supplied to cutting member (210) to further assist in severing the tissue. Indeed, in some versions cutting member (210) may be dull and the severing of the tissue is performed by supplying RF energy to the dull cutting member (210) and advancing cutting member (210) distally. Furthermore, cutting member (210) may be actuated by a second trigger (not shown) or, in one alternative, by further actuation of trigger (156). In the present example, cutting member (210) comprises an upper flange and a lower flange on opposing ends of a blade, thereby forming an I-shaped member. As cutting member (210) is actuated distally, the flanges assist in compressing upper jaw (206) against lower jaw (208).

Of course end effector (200) and surgical instrument (150) may include other configurations as will be apparent to one of ordinary skill in the art in view of the teachings herein.

III. Exemplary Coupling Mechanisms for Modular Shafts and End Effectors

In some instances it may be useful to change between various shaft lengths and/or types of end effectors (80, 200) while using the same handle assembly (60, 152). For instance, in some procedures, a large amount of tissue may need to be cut, requiring different length end effectors (80, 200) and/or shafts for transmission assemblies (70, 170). Such interchangeable shafts and/or end effectors (80, 200) may permit a common handle assembly (60, 152) to be used for various surgical procedures (e.g., short shafts for open surgery, long shafts for minimally invasive laparoscopic surgery, etc.). Moreover, changing out the shafts and/or the end effectors (80, 200) while reusing the same handle assembly (60, 152) may be more time and/or cost effective than using a new surgical instrument (50, 150) with the different length shaft. By way of example only, such shafts and/or end effectors (80, 200) may include color codes to distinguish the various lengths and/or types. In another instance, the handle assembly (60, 152) may be configured to employ different types of end effectors, for instance, the handle assembly (60, 152) may include components to operate an ultrasonic end effector (80) and/or an RE end effector (200). Thus, changing the shafts and end effectors (80, 200) with a common handle assembly (60, 152) may conserve time and/or costs. Accordingly, various coupling mechanisms for coupling the modular shafts to the handle assemblies (60, 152) are described below. It should be understood that in versions where an ultrasonic end effector (80) is used, at least part of transducer (100) may be integral with the shaft and end effector (80), and may thus be selectively coupled with handle assembly (60). Alternatively, transducer (100) may be integral with handle assembly (60) such that the shaft and end effector (80) are selectively coupled with transducer (100) when the shaft and end effector (80) are selectively coupled with handle assembly (60).

A. Exemplary Resilient Tabs on Shaft

Figure 5A:
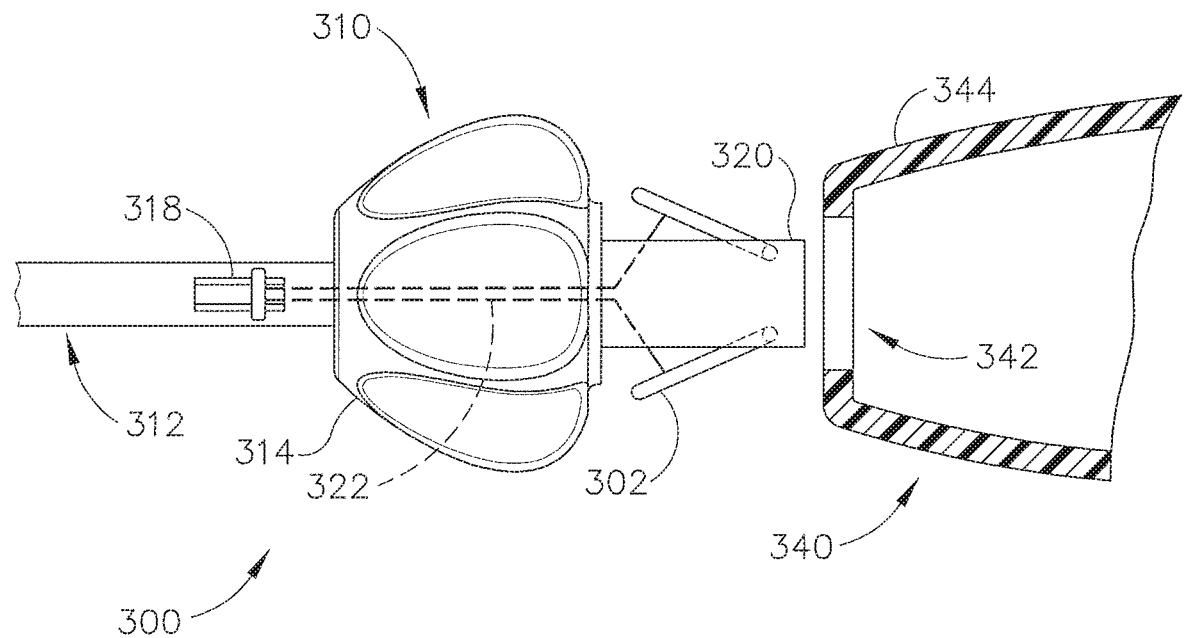
FIG. 5A depicts a side elevation view of a first exemplary coupling mechanism with a portion of a handle assembly removed to show the interior thereof and showing a decoupled end effector assembly.
Figure 5B:
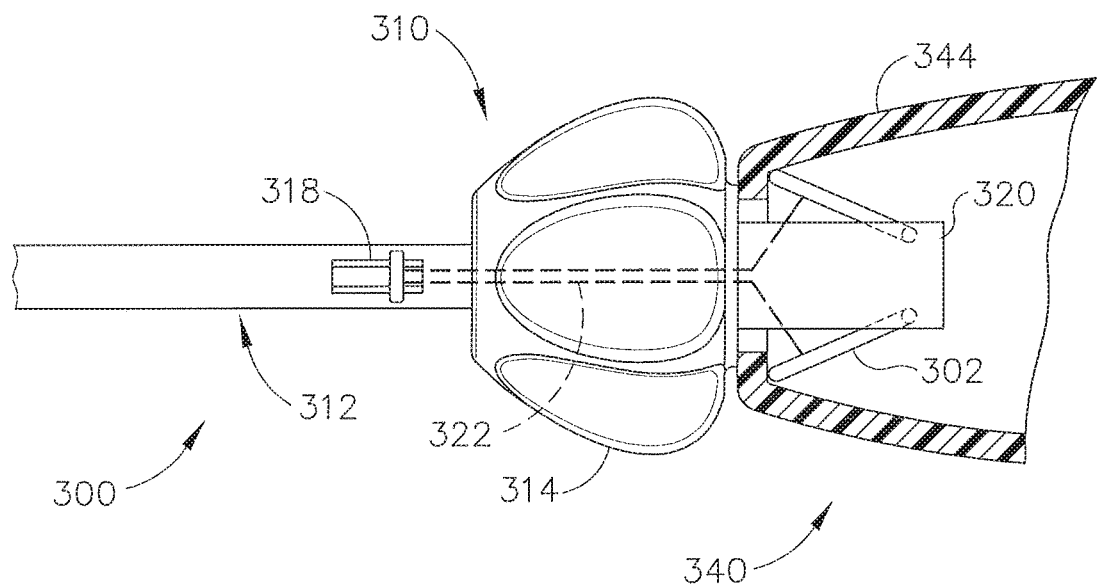
FIG. 5B depicts a side elevation view of the coupling mechanism of FIG. 5A showing the end effector assembly coupled to the handle assembly.

A first exemplary coupling mechanism (300) comprises tabs (302) extending from an insertable portion of a shaft (320) of an exemplary end effector assembly (310), shown in FIGS. 5A-5B. In the present example, end effector assembly (310) comprises a transmission assembly (312), a rotation knob (314), and a shaft (320) extending proximally relative to rotation knob (314). It should be understood that rotation knob (314) is merely optional and may be omitted. In other versions, rotation knob (314) may be coupled to handle assembly (340) and end effector assembly (310) may be inserted through rotation knob (314). Rotation knob (314) is operable to rotate transmission assembly (312) relative to a handle assembly (340) and/or shaft (320). An end effector (not shown) is coupled to a distal end of transmission assembly (312). The end effector may include an ultrasonic end effector (80), an RF end effector (200), and/or any other end effector or combination of end effectors as will be apparent to one of ordinary skill in the art in view of the teachings herein. In the instance of an ultrasonic end effector, such as end effector (80), an axial bore (not shown) through shaft (320) may permit mechanical coupling of transmission assembly (312) through shaft (320) to components within handle assembly (340), which may be configured in a similar manner to multi-piece handle assembly (60) described above. In the case of an RF end effector, such as end effector (200), the axial bore may permit a portion of transmission assembly (312) to extend at least partially through shaft (320). Transmission assembly (312) may include an inner slip ring connector that is electrically coupleable to a complementary slip ring connector on the interior of shaft (320) such that an electrical coupling from handle assembly (340) may be made to the end effector. In yet another alternative, a fluid coupling may also be made via the bore through shaft (320) and/or elsewhere on end effector assembly (310).

In the present example, a pair of resilient tabs (302) extend outwardly from shaft (320). Resilient tabs (302) may comprise a resilient non-conductive material, such as a plastic, or resilient tabs (302) may comprise a conductive material, such as a metallic material. If resilient tabs (302) are conductive, resilient tabs (302) may also be operable to electrically couple components of the end effector to components within handle assembly (340). For instance, resilient tabs (302) may electrically couple portions of first and second conductor (220, 222) mentioned previously. Of course, such electrical coupling is merely optional. As shown in FIGS. 5A-5B, resilient tabs (302) couple to shaft (320) near a proximal end of shaft (320) and extend outwardly from a longitudinal axis of shaft (320) as resilient tabs (302) extend distally. In the present example, handle assembly (340) is shown having a distal aperture (342) formed within a casing (344) and configured to receive shaft (320) of end effector assembly (310). Handle assembly (340) may be further configured in accordance with at least some of the teachings for multi-piece handle assembly (60), for handle assembly (152), of U.S. Pat. Pub. No. 2011/0015660, entitled "Rotating Transducer Mount for Ultrasonic Surgical Instruments," published Jan. 20, 2011, issued as U.S. Pat. No. 8,461,744 on Jun. 11, 2013 or of U.S. Pat. No. 6,500, 176, entitled "Electrosurgical Systems and Techniques for Sealing Tissue," issued Dec. 31, 2002, the disclosures of which are incorporated by reference herein. In the present example, an unlock slider (318) is located on a proximal portion of transmission assembly (312) and is coupled to an inner actuatable member (322) (shown in phantom) that is coupled to tabs (302). Unlock slider (318) is operable to pull resilient tabs (302) inwardly towards shaft (320), thereby permitting a user to remove shaft (320) distally past casing (344). Alternatively, unlock slider (318) may be located on rotation knob (314). Further still, handle assembly (340) may comprise one or more release buttons (not shown) that depress resilient tabs (302) when end effector assembly (310) is to be decoupled from handle assembly (340).

As shown in the sequence of FIGS. 5A-5B, when shaft (320) of end effector assembly (310) is inserted into distal aperture (342), resilient tabs (302) depress against shaft (320) while end effector assembly (310) is inserted. Once the distal ends of resilient tabs (302) clear casing (344) through distal aperture (342), resilient tabs (302) spring back to their original orientation, thereby longitudinally coupling end effector assembly (310) to handle assembly (340). In some instances, the user may actuate slider (318) to manually retract resilient tabs (302) during insertion into distal aperture (342). In the instance of an ultrasonic instrument, shaft (320) of end effector assembly (310) may be threaded onto a horn of a transducer, such as transducer (100) described above. Such threading may occur contemporaneously with the compression of resilient tabs (302) or after resilient tabs (302) have cleared casing (344). Alternatively, in the instance of an RF instrument, shaft (320) may be coupled to one or more electrical connectors (not shown) to couple the end effector to a power source. Merely exemplary electrical couplings are shown and described in reference to FIGS. 15-17. As shown in FIG. 5B, end effector assembly (310) is effectively longitudinally secured to handle assembly (340) while permitting rotational movement of shaft (320), rotation knob (314), and/or transmission assembly (312) relative to casing (314). A user may then use the assembled surgical instrument for a procedure. When the user desires to decouple end effector assembly (310) from handle assembly (340), the user slides unlock slider (318) distally until resilient tabs (302) are sufficiently depressed against shaft (320) to permit the user to slide shaft (320) past casing (344) through distal aperture (342). A user may then couple a new end effector assembly (310) to handle assembly (340).

Of course other configurations for first coupling mechanism (300) will be apparent to one of ordinary skill in the art in view of the teachings herein. For instance, resilient members (302) may include expansion springs to urge tabs (302) outwardly from shaft (320). Further still, one or more resiliently biased cams may replace resilient tabs (302). In other versions, resilient tabs (302) may instead be elastomeric wedges that may deform to allow end effector assembly (310) to be inserted. In addition, while two resilient tabs (302) are depicted, a single resilient tab (302) or more than two resilient tabs (302) may be used with first coupling mechanism (300). Moreover, end effector assembly (310) need not necessarily be removeable from handle assembly (340). In such instances, the user may simply disposed of both end effector assembly (310) and handle assembly (340) after a surgical procedure. As will become apparent from the later disclosures herein, various other electrical and/or mechanical coupling mechanisms and/or features may be combined with first coupling mechanism (300) as well.

B. Exemplary Flexible Handle Assembly Portion

Figure 6A:
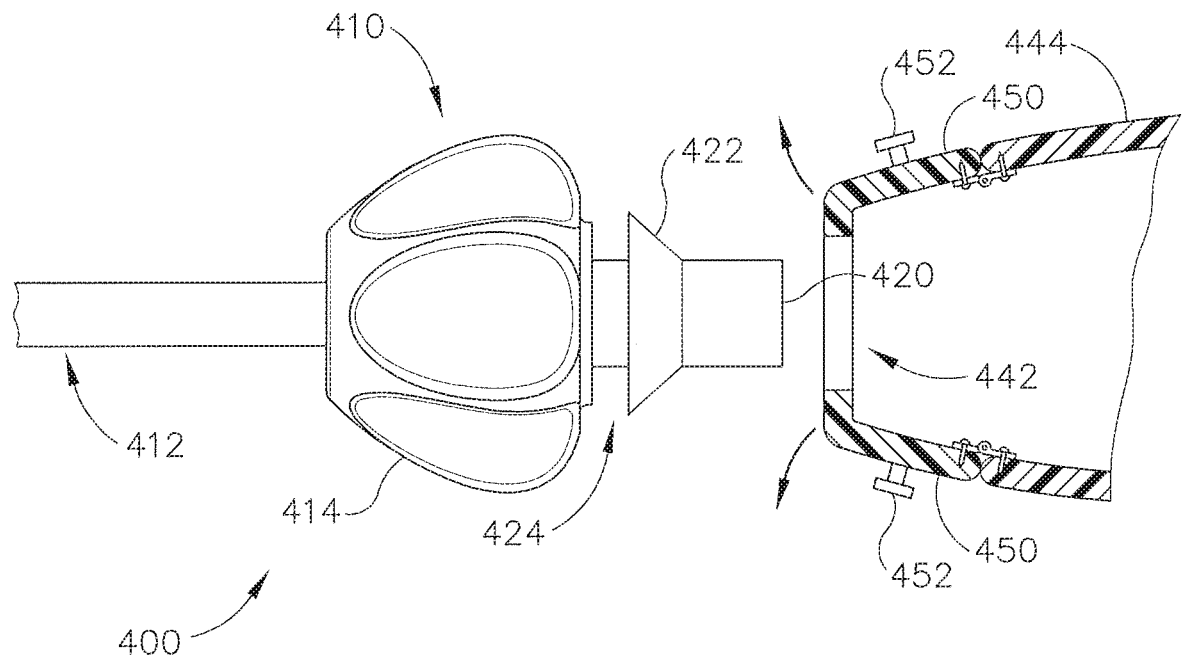
FIG. 6A depicts a side elevation view of a second exemplary coupling mechanism with a portion of a handle assembly removed to show the interior thereof and showing a decoupled end effector assembly.
Figure 6B:
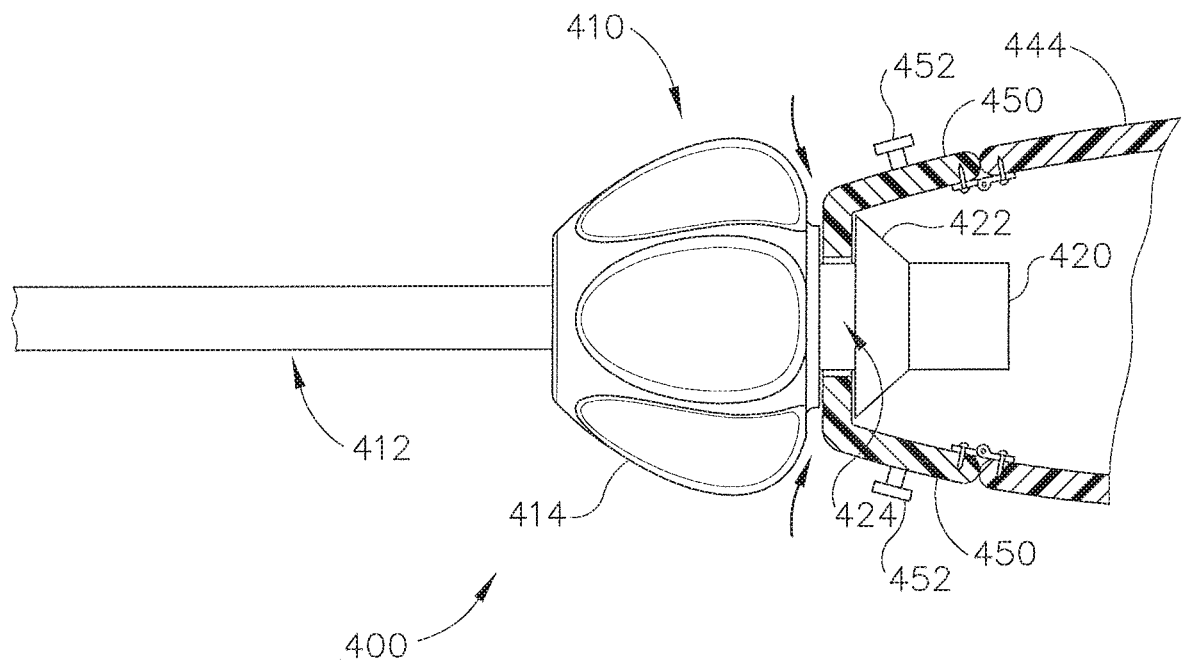
FIG. 6B depicts a side elevation view of the coupling mechanism of FIG. 6A showing the end effector assembly coupled to the handle assembly.

A second exemplary coupling mechanism (400) comprises resiliently biased portions (450) of casing (444) configured to capture a shaft (420) of an alternative exemplary end effector assembly (410), shown in FIGS. 6A-6B. In the present example, end effector assembly (410) comprises a transmission assembly (412), a rotation knob (414), and a shaft (420) extending proximally relative to rotation knob (414). It should be understood that rotation knob (414) is merely optional and may be omitted. Rotation knob (414) is operable to rotate transmission assembly (412) relative to a handle assembly (440) and/or shaft (420). An end effector (not shown) is coupled to a distal end of transmission assembly (412). The end effector may include an ultrasonic end effector (80), an RF end effector (200), and/or any other end effector or combination of end effectors as will be apparent to one of ordinary skill in the art in view of the teachings herein. In the instance of an ultrasonic end effector, such as end effector (80), an axial bore (not shown) through shaft (420) may permit mechanical coupling of transmission assembly (412) through shaft (420) to components within handle assembly (440), which may be configured in a similar manner to multi-piece handle assembly (60) described above. In the case of an RF end effector, such as end effector (200), the axial bore may permit a portion of transmission assembly (412) to extend at least partially through shaft (420). Transmission assembly (412) may include an inner slip ring connector that is electrically coupleable to a complementary slip ring connector on the interior of shaft (420) such that an electrical coupling from handle assembly (440) may be made to the end effector. In yet another alternative, a fluid coupling may also be made via the bore through shaft (420) and/or elsewhere on end effector assembly (410).

In the present example, shaft (420) comprises a circumferential ramp (422) and a circumferential recess (424) located distally of circumferential ramp (422) but proximal to rotation knob (414). In the present example, handle assembly (440) is shown having a distal aperture (442) formed within a casing (444) and configured to receive shaft (420) of end effector assembly (410). Handle assembly (440) may further be configured in accordance with at least some of the teachings for multi-piece handle assembly (60), for handle assembly (152), of U.S. Pat. Pub. No. 2011/0015660, entitled "Rotating Transducer Mount for Ultrasonic Surgical Instruments," published Jan. 20, 2011, issued as U.S. Pat. No. 8,461,744 on Jun. 11, 2013, or of U.S. Pat. No. 6,500,176, entitled "Electrosurgical Systems and Techniques for Sealing Tissue," issued Dec. 31, 2002, the disclosures of which are incorporated by reference herein. In the present example, handle assembly (440) comprises one or more resiliently biased portions (450) located at the distal end of handle assembly (440). As shown in FIGS. 6A-6B, one or more handles (452) are coupled to resiliently biased portions (450) to allow a user to manually open the distal end of handle assembly (440) either during insertion of shaft (420) or to release shaft (420).

As shown in the sequence of FIGS. 6A-6B, when shaft (420) of end effector assembly (410) is inserted into distal aperture (442), resiliently biased portions (450) of handle assembly (440) cam outwardly under the influence of circumferential ramp (422) of shaft (420). Once the ends of resiliently biased portions (450) encounter recess (424), resiliently biased portions (450) spring back to their original orientation, thereby coupling end effector assembly (410) to handle assembly (440) between rotation knob (414) and a distal wall of circumferential ramp (422). As shown in FIG. 6B, end effector assembly (410) is effectively longitudinally secured to handle assembly (440) while permitting rotational movement of shaft (420), rotation knob (414), and/or transmission assembly (412) relative to casing (444). In the instance of an ultrasonic instrument, shaft (420) of end effector assembly (410) may be threaded onto a horn of a transducer, such as transducer (100) described above. Such threading may occur contemporaneously with the deflection of resiliently biased portions (450) or after resiliently biased portions (450) have sprung back into recess (424). Alternatively, in the instance of an RF instrument, shaft (420) may be coupled to one or more electrical connectors (not shown) to couple the end effector to a power source. Merely exemplary electrical couplings are shown and described in reference to FIGS. 15-17. A user may then use the assembled surgical instrument for a procedure. When the user desires to decouple end effector assembly (410) from handle assembly (440), the user pulls outwardly on the one or more handles (452) of resiliently biased portions (450) until the ends of resiliently biased portions (450) clear the distal wall of circumferential ramp (422), thereby permitting the user to slide circumferential ramp (422) and shaft (420) past resiliently biased portions (450) and through the now-expanded distal aperture (442). A user may then couple a new end effector assembly (410) to handle assembly (440). In some versions, a tab (not shown) may be provided to pivot resiliently biased portions (450) open. Accordingly, a user may only need to press on the tabs to expand distal aperture (442).

Of course other configurations for second coupling mechanism (400) will be apparent to one of ordinary skill in the art in view of the teachings herein. In one alternative configuration, resiliently biased portions (450) may omit springs and, instead, may be resilient, deflectable portions of casing (444). Alternatively, circumferential ramp (422) may comprise discrete ramps disposed about shaft (420) instead of a single continuous circumferential ramp. Further still, resilient tabs (302) shown in FIGS. 5A-5B may be used instead of circumferential ramp (422). As will become apparent from the previous and later disclosures herein, various other electrical and/or mechanical coupling mechanisms and/or features may be combined with second coupling mechanism (400) as well.

C. Exemplary Slide Lock

Figure 7A:
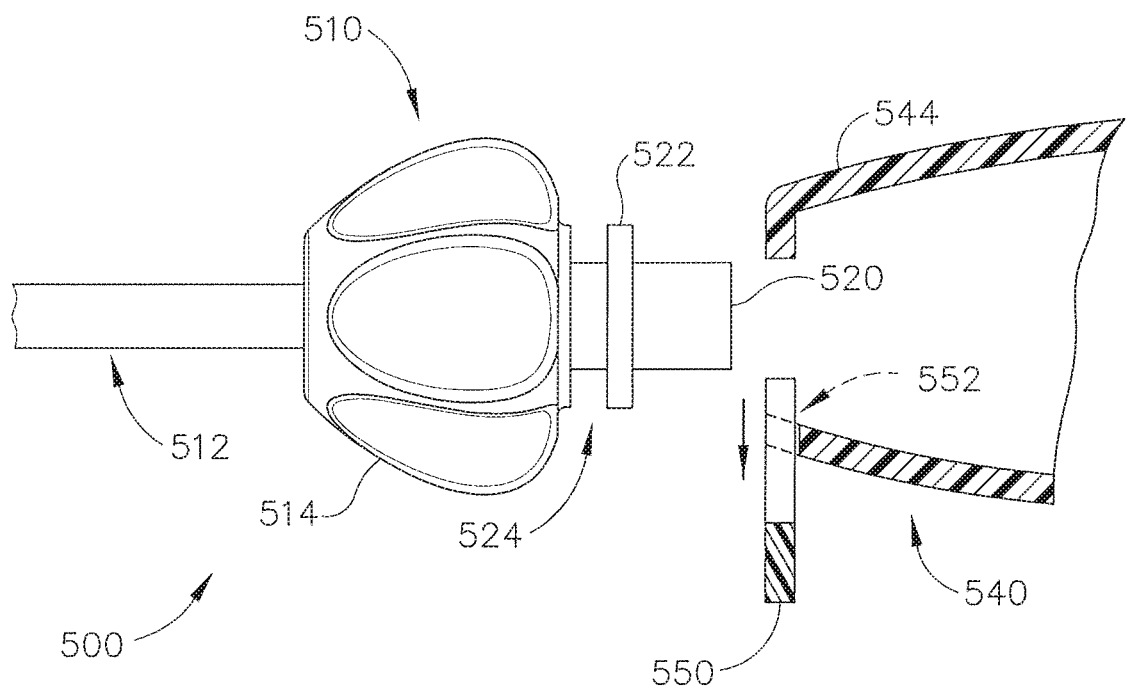
FIG. 7A depicts a side elevation view of a third exemplary coupling mechanism with a portion of a handle assembly removed to show the interior thereof and showing a decoupled end effector assembly.
Figure 7B:
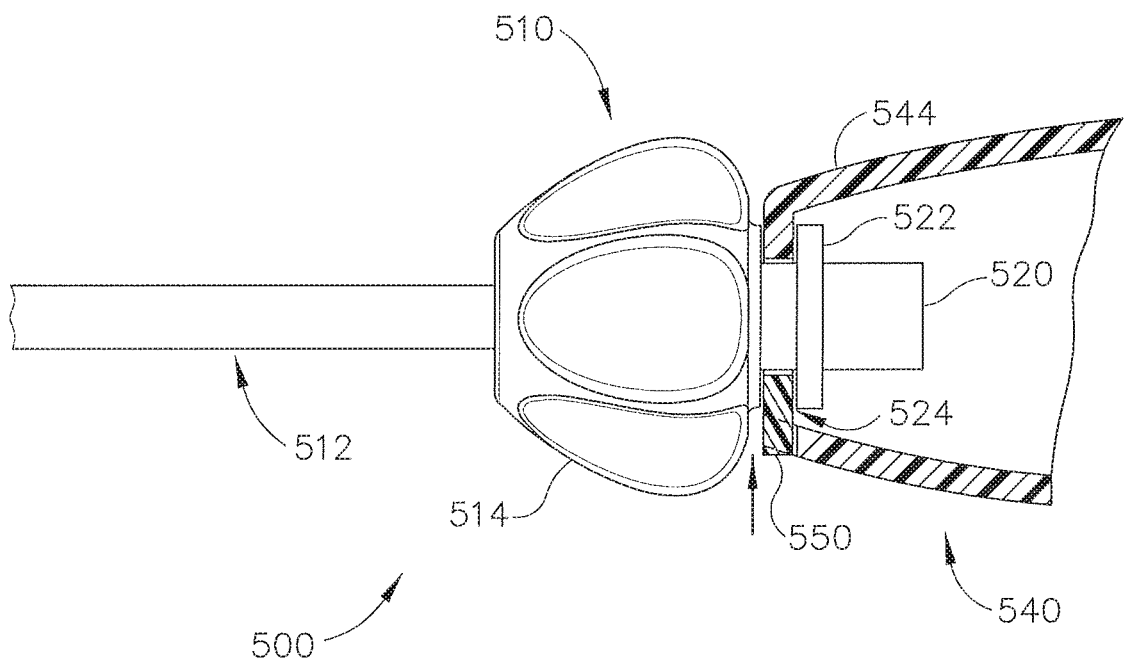
FIG. 7B depicts a side elevation view of the coupling mechanism of FIG. 7A showing the end effector assembly coupled to the handle assembly.

A third exemplary coupling mechanism (500) comprises a slide-locking portion (550) of casing (544) configured to capture a shaft (520) of yet another exemplary end effector assembly (510), shown in FIGS. 7A-7B. In the present example, end effector assembly (510) comprises a transmission assembly (512), a rotation knob (514), and a shaft (520) extending proximally relative to rotation knob (514). It should be understood that rotation knob (514) is merely optional and may be omitted. Rotation knob (514) is operable to rotate transmission assembly (512) relative to a handle assembly (540) and/or shaft (520). An end effector (not shown) is coupled to a distal end of transmission assembly (512). The end effector may include an ultrasonic end effector (80), an RF end effector (200), and/or any other end effector or combination of end effectors as will be apparent to one of ordinary skill in the art in view of the teachings herein. In the instance of an ultrasonic end effector, such as end effector (80), an axial bore (not shown) through shaft (520) may permit mechanical coupling of transmission assembly (512) through shaft (520) to components within handle assembly (540), which may be configured in a similar manner to multi-piece handle assembly (60) described above. In the case of an RF end effector, such as end effector (200), the axial bore may permit a portion of transmission assembly (512) to extend at least partially through shaft (520). Transmission assembly (512) may include an inner slip ring connector that is electrically coupleable to a complementary slip ring connector on the interior of shaft (520) such that an electrical coupling from handle assembly (540) may be made to the end effector. In yet another alternative, a fluid coupling may also be made via the bore through shaft (520) and/or elsewhere on end effector assembly (510).

In the present example, shaft (520) comprises an annular flange (522) with a recess (524) located distally of annular flange (522) but proximal of rotation knob (514). Slide-locking portion (550) includes a notch (552) (shown in phantom) configured to secure shaft (520) of end effector assembly (510) when slide-locking portion (550) is slidably translated into a locked position. Notch (552) may be configured similarly to notch (952) shown in FIG. 11A. Handle assembly (540) may further be configured in accordance with at least some of the teachings for multi-piece handle assembly (60), for handle assembly (152), of U.S. Pat. Pub. No. 2011/0015660, entitled "Rotating Transducer Mount for Ultrasonic Surgical Instruments," published Jan. 20, 2011, issued as U.S. Pat. No. 8,461,744 on Jun. 11, 2013, or of U.S. Pat. No. 6,500,176, entitled "Electrosurgical Systems and Techniques for Sealing Tissue," issued Dec. 31, 2002, the disclosures of which are incorporated by reference herein. In the present example, slide-locking portion (550) is located at the distal end of handle assembly (540) and is configured to slidably translate between an open position, shown in FIG. 7A, in which an opening is formed in casing (544) into which shaft (520) and annular flange (522) may be inserted, and a locked position, shown in FIG. 7B. Slide-locking portion (550) of the present example is a manually translatable portion, thought it should be understood that slide-locking portion (550) may include a return spring biased to return slide-locking portion to the locked position. In the present example, slide-locking portion (550) comprises tabs (not shown) that are contained within vertical channels (not shown) formed in casing (544), thereby restricting the movement of slide-locking portion (550) to vertical translation within the channels. Slide-locking portion (550) may further comprise a snap fitting operable to couple slide-locking portion (550) to the upper portion of casing (544) when slide-locking portion is in the locked position.

As shown in the sequence of FIGS. 7A-7B, slide-locking portion (550) is initially slidably translated downwardly to form an opening into which shaft (520) and annular flange (522) may be inserted into handle assembly (540). In the instance of an ultrasonic instrument, shaft (520) of end effector assembly (510) may be threaded onto a horn of a transducer, such as transducer (100) described above. Such threading may occur prior to, contemporaneously with, or after sliding slide-locking portion (550) into the locked position. Alternatively, in the instance of an RF instrument, shaft (520) may be coupled to one or more electrical connectors (not shown) to couple the end effector to a power source. Merely exemplary electrical couplings are shown and described in reference to FIGS. 15-17. If a manually operable slide-locking portion (550) is used, the user slidably translates slide-locking portion (550) upwardly such that notch (552) is aligned with recess (524) of shaft (520). As shown in FIG. 7B, end effector assembly (510) is effectively longitudinally secured to handle assembly (540) by the combination of slide-locking portion (550), annular flange (522), and rotation knob (514), while still permitting rotational movement of shaft (520), rotation knob (514), and/or transmission assembly (512) relative to casing (544). A user may then use the assembled surgical instrument for a procedure. When the user desires to decouple end effector assembly (510) from handle assembly (540), the user slidably translates slide-locking portion (550) downwardly until annular flange (522) and shaft (520) can clear slide-locking portion (550) and/or notch (552). A user may then couple a new end effector assembly (510) to handle assembly (540).

Of course other configurations for third coupling mechanism (500) will be apparent to one of ordinary skill in the art in view of the teachings herein. As will become apparent from the previous and later disclosures herein, various other electrical and/or mechanical coupling mechanisms and/or features may be combined with third coupling mechanism (500).

D. Exemplary Threaded Slip Nut

Figure 8A:
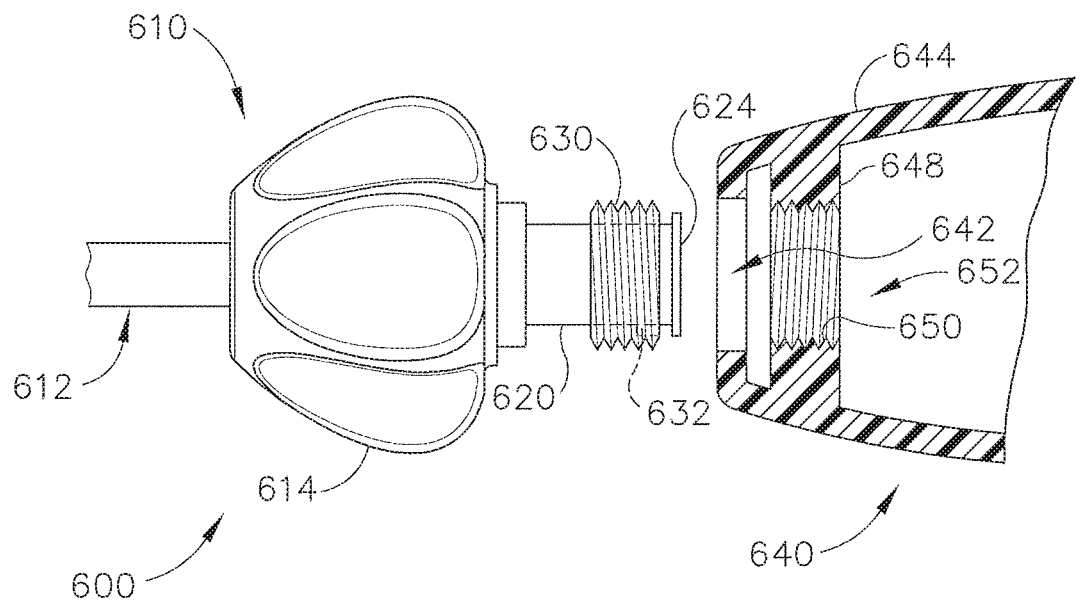
FIG. 8A depicts a side elevation view of a fourth exemplary coupling mechanism with a portion of a handle assembly removed to show the interior thereof and showing a decoupled end effector assembly.
Figure 8B:
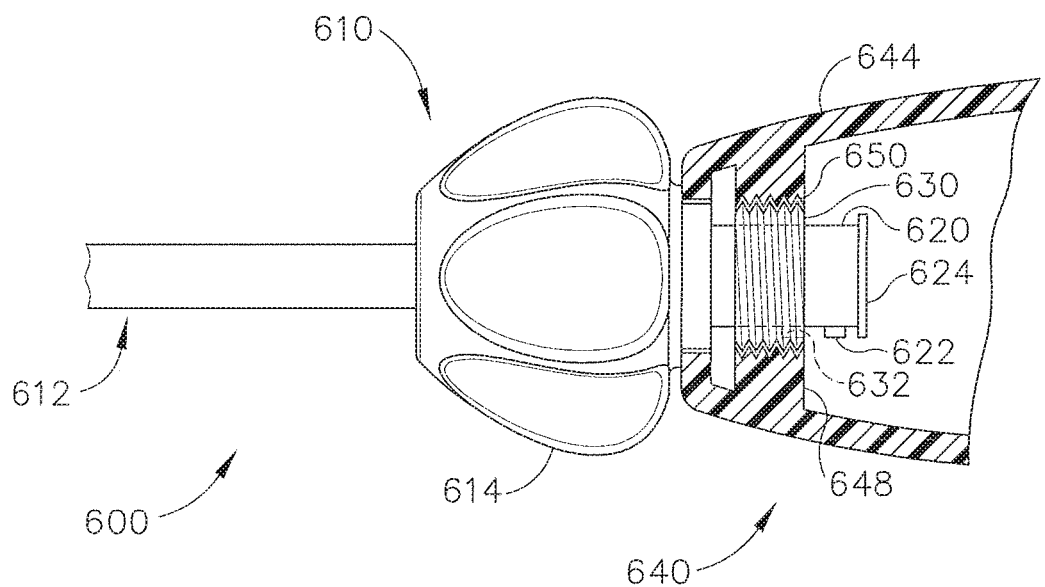
FIG. 8B depicts a side elevation view of the coupling mechanism of FIG. 8A showing the end effector assembly coupled to the handle assembly.

A fourth exemplary coupling mechanism (600) comprises a threaded slip nut (630) disposed about a shaft (620) of an exemplary end effector assembly (610), shown in FIGS. 8A-8B. In the present example, end effector assembly (610) comprises a transmission assembly (612), a rotation knob (614), and a shaft (620) extending proximally relative to rotation knob (614). It should be understood that rotation knob (614) is merely optional and may be omitted. Rotation knob (614) is operable to rotate transmission assembly (612) relative to a handle assembly (640) and/or shaft (620). An end effector (not shown) is coupled to a distal end of transmission assembly (612). The end effector may include an ultrasonic end effector (80), an RF end effector (200), and/or any other end effector or combination of end effectors as will be apparent to one of ordinary skill in the art in view of the teachings herein. In the instance of an ultrasonic end effector, such as end effector (80), an axial bore (not shown) through shaft (620) may permit mechanical coupling of transmission assembly (612) through shaft (620) to components within handle assembly (640), which may be configured in a similar manner to multi-piece handle assembly (60) described above. In the case of an RF end effector, such as end effector (200), the axial bore may permit a portion of transmission assembly (612) to extend at least partially through shaft (620). Transmission assembly (612) may include an inner slip ring connector that is electrically coupleable to a complementary slip ring connector on the interior of shaft (620) such that an electrical coupling from handle assembly (640) may be made to the end effector. In yet another alternative, a fluid coupling may also be made via the bore through shaft (620) and/or elsewhere on end effector assembly (610).

In the present example, a threaded slip nut (630) is slidably disposed about shaft (620). Threaded slip nut (630) includes a keyway (632) (shown in phantom) at a proximal end of threaded slip nut (630). It should be understood that keyway (632) may alternatively be located on a distal end of threaded slip nut (630). Keyway (632) of the present example only partially extends through threaded slip nut (630), though keyway (632) may alternatively extend completely through threaded slip nut (630). As shown in FIGS. 8A-8B, keyway (632) is configured to receive a keyed portion (622) of shaft (620). In the present example, keyed portion (622) of shaft (620) is located near a proximal end of shaft (620) and extends outwardly from shaft (620), though it should be understood that keyed portion (622) may alternatively be located distally near rotation knob (614) or at a midpoint of shaft (620). In one merely alternative example, keyed portion (622) may be slidable relative to shaft (620), such as by actuation of a slider, for instance, slider (318) shown in FIGS. 5A-59, to slide keyed portion (622) into keyway (632). Shaft (620) further comprises a proximal flange (624) located on the proximal end of shaft (620) and sized to prevent threaded slip nut (630) from sliding proximally off of shaft (620). As will be described below, keyed portion (622) is insertable into keyway (632) when a user desires to thread threaded slip nut (630) into internal threading (650) of handle assembly (640). Threaded slip nut (630) of the present example may then be slid distally on shaft (620) to disengage keyed portion (622) from keyway (632), thereby permitting shaft (620), rotation knob (614), and/or transmission assembly (612) to rotate freely relative to threaded slip nut (630) and/or handle assembly (640).

In some instance threaded slip nut (630) may be slidably disposed on an inner tube, such as an inner tubular actuating member described above. In such a configuration, threaded slip nut (630) may be configured to thread into a yoke, such as trigger yoke (185) described in U.S. Pat. Pub. No. 2011/0015660, entitled "Rotating Transducer Mount for Ultrasonic Surgical Instruments," published Jan. 20, 2011, issued as U.S. Pat. No. 8,461,744 on Jun. 11, 2013, the disclosure of which is incorporated by reference herein. A blade, such as blade (82) described above, may be coupled to a transducer, such as transducer (100) described above. The inner tubular actuating member may be actuated via the coupling of threaded slip nut (630) to the yoke. Accordingly, a clamp arm, such as clamp arm (84) described above, may be operable to clamp tissue against the blade.

In the present example, handle assembly (640) is shown having a distal aperture (642) formed within a casing (644) and configured to receive shaft (620) and threaded slip nut (630) of end effector assembly (610). Handle assembly (640) may further be configured in accordance with at least some of the teachings for multi-piece handle assembly (60), for handle assembly (152), of U.S. Pat. Pub. No. 2011/0015660, entitled "Rotating Transducer Mount for Ultrasonic Surgical Instruments," published Jan. 20, 2011, issued as U.S. Pat. No. 8,461,744 on Jun. 11, 2013, or of U.S. Pat. No. 6,500,176, entitled "Electrosurgical Systems and Techniques for Sealing Tissue," issued Dec. 31, 2002, the disclosures of which are incorporated by reference herein. In the present example, handle assembly (640) includes a member (648) having internal threading (650) disposed about a member aperture (652). Internal threading (650) and threaded slip nut (630) are configured to thread together to secure end effector assembly (610) to handle assembly (640).

As shown in the sequence of FIGS. 8A-8B, threaded slip nut (630) of the present example is slid proximally such that keyed portion (622) of shaft (620) engages keyway (632) of threaded slip nut (630). With the rotational freedom of threaded slip nut (630) restricted by the engagement of keyed portion (622) and keyway (632), a user then threads threaded slip nut (630) into internal threading (650) of handle assembly (640). For instance, an L-shaped spacer tool may be used to urge threaded slip nut (630) proximally on shaft (620) against flange (624) while the user threads threaded slip nut (630) into internal threading (650). Alternatively, a user may manually urge threaded slip nut (630) proximally. Further still, a slider, as noted above, may engage a portion of threaded slip nut (630) to urge threaded slip nut (630) proximally. Of course, still other methods of urging threaded slip nut (630) proximally to engage keyed portion (622) and keyway (632) will be apparent to those of ordinary skill in the art in view of the teachings herein. For instance, a spring (not shown) may be disposed about shaft (620) distally of slip nut (630) and proximally of rotation knob (614), thereby biasing slip nut (630) proximally such that keyway (632) is engaged with keyed portion (622). When the user desires to rotate end effector assembly (610), the user grasps rotation knob (614) and pushes end effector assembly (610) proximally until keyed portion (622) disengages from keyway (632).

Once threaded slip nut (630) has been sufficiently threaded into internal threading (650) (for instance, a torque limiting tool may be used), end effector assembly (610) is slid proximally to disengage keyed portion (622) from keyway (632). End effector assembly (610) may be manually slid distally or, in one alternative, a spring (not shown) located between flange (624) and threaded slip nut (630) may urge end effector assembly (610) distally. In the instance of an ultrasonic instrument, shaft (620) of end effector assembly (610) may be threaded onto a horn of a transducer, such as transducer (100) described above. Such threading may occur prior to, contemporaneously with, or after the threading of threaded slip nut (630) into internal threading (650). Alternatively, in the instance of an RF instrument, shaft (620) may be coupled to one or more electrical connectors (not shown) to couple the end effector to a power source. Merely exemplary electrical couplings are shown and described in reference to FIGS. 15-17. As shown in FIG. 8B, end effector assembly (610) is effectively longitudinally secured to handle assembly (640) while permitting rotational movement of shaft (620), rotation knob (614), and/or transmission assembly (612). A user may then use the assembled surgical instrument for a procedure. When the user desires to decouple end effector assembly (610)

from handle assembly (640), the user pulls end effector assembly (610) distally until keyed portion (622) of shaft (620) engages keyway (632) of threaded slip nut (630). Alternatively, the L-shaped spacer tool may be wedged between threaded slip nut (630) and rotation knob (614) to urge threaded slip nut (630) proximally. With keyed portion (622) and keyway (632) engaged, the user may then unscrew threaded slip nut (630) from internal threading (650), thereby decoupling end effector assembly (610) from handle assembly (640). A user may then couple a new end effector assembly (610) to handle assembly (640).

Of course other configurations for fourth coupling mechanism (600) will be apparent to one of ordinary skill in the art in view of the teachings herein. For instance, threaded slip nut (630) may be located between flange (624) and another annular flange (not shown), such as annular flange (522) shown in FIGS. 7A-7B, of shaft (620). In this example, keyed portion (622) may be actuated radially outward from an initial position within a recess (not shown) of shaft (620) to a position where keyed portion (622) engages keyway (632) of threaded slip nut (630). For instance, keyed portion (622) may be actuated by a cam member coupled to a slider, such as slider (318) of FIGS. 5A-5B, located on transmission assembly (612) and/or rotation knob (614). As will become apparent from the previous and later disclosures herein, various other electrical and/or mechanical coupling mechanisms and/or features may be combined with fourth coupling mechanism (600).

E. Exemplary T-Shaped Connectors

A fifth exemplary coupling mechanism (700) comprises one or more shafts (722, 724, 726) having one or more circumferential flanges (728, 730, 732) forming one or more T-shaped insertable connectors (734, 736, 738) for an exemplary end effector assembly (710), shown in FIGS. 9A-9B. In the present example, end effector assembly (710) comprises a transmission assembly (712), a rotation knob (714), and one or more shafts (722, 724, 726) extending proximally relative to rotation knob (714). It should be understood that rotation knob (714) is merely optional and may be omitted. Rotation knob (714) is operable to rotate transmission assembly (712) relative to a handle assembly (740) and/or the one or more shafts (722, 724, 726). An end effector (not shown) is coupled to a distal end of transmission assembly (712). The end effector may include an ultrasonic end effector (80), an RF end effector (200), and/or any other end effector or combination of end effectors as will be apparent to one of ordinary skill in the art in view of the teachings herein.

The present exemplary end effector assembly (710) is configured for an RF end effector, such as end effector (200). Handle assembly (740) comprises a casing (744) having a distal aperture (742) into which the proximal end of end effector assembly (710) may be inserted. In the present example, handle assembly (740) further comprises a pair of deflectable distal tabs (748) located proximally of distal aperture (742), a first actuation mechanism (760), a second actuation mechanism (770), and an electrical coupling member (750). Distal tabs (748) are operable to engage distal T-shaped connector (734) to restrict the longitudinal movement of end effector assembly (710) when inserted into handle assembly (740). Proximal flange (732) of end effector assembly (710) includes one or more electrical contacts (720) operable to electrically couple to complementary contacts (752) on electrical coupling member (750). Complementary contacts (752) are further coupled to a power source, such as generator (20) or an internal power source within handle assembly (740), to provide power to the end effector. Such contacts (720, 752) may be complementary slip ring contacts, annular ring contacts, male and female connectors, and/or any other suitable rotary or non-rotary electrical connection. In the present example, contacts (720, 752) comprise a brushed slip ring electrical connection.

As noted above, end effector assembly (710) comprises a proximal T-shaped connector (738), a middle T-shaped connector (736) and a distal T-shaped connector (734). Proximal T-shaped connector (738) and middle T-shaped connector (736) of the present example are operable to couple to a first actuation mechanism (760) and a second actuation mechanism (770), respectively. First and second actuation mechanisms (760, 770) are operable to actuate an upper jaw, such as upper jaw (206), and a cutting mechanism, such as cutting member (210), respectively. In the present example, the distal ends of first and second actuation mechanisms (760, 770) each include an angled portion (762, 772) configured to cam the distal ends of first and second actuation mechanisms (760, 770) outwardly when T-shaped connectors (736, 738) of end effector assembly (710) are inserted into handle assembly (740). Once T-shaped connectors (736, 738) clear the proximal end of angled portions (762, 772), proximal shaft (726) and middle shaft (724) may be actuated proximally via the coupling of T-shaped connectors (736, 738) with first and second actuation mechanisms (760, 770).

In addition, distal T-shaped connector (734) is operable to couple with deflectable distal tabs (748) to longitudinally secure end effector assembly (710) to handle assembly (740). As will be apparent to one of ordinary skill in the art, the coupling of T-shaped connectors (734, 736, 738) with deflectable distal tabs (748), first actuation mechanism (760), and/or second actuation mechanism (770) still permits end effector assembly (710) to rotate freely even while coupled to handle assembly (740). Handle assembly (740) may further be configured in accordance with at least some of the teachings for multi-piece handle assembly (60), for handle assembly (152), of U.S. Pat. Pub. No. 2011/0015660, entitled "Rotating Transducer Mount for Ultrasonic Surgical Instruments," published Jan. 20, 2011, issued as U.S. Pat. No. 8,461,744 on Jun. 11, 2013 or of U.S. Pat. No. 6,500,176, entitled "Electrosurgical Systems and Techniques for Sealing Tissue," issued Dec. 31, 2002, the disclosures of which are incorporated by reference herein.

As shown in the sequence of FIGS. 9A-9B, when T-shaped connectors (734, 736, 738) of end effector assembly (710) are inserted into distal aperture (742), deflectable distal tabs (748), first actuation mechanism (760), and/or second actuation mechanism (770) deflect outwardly until T-shaped connectors (734, 736, 738) are captured therein. As shown in FIG. 9B, end effector assembly (710) is effectively longitudinally secured to handle assembly (740) while permitting rotational movement of shafts (722, 724, 726), rotation knob (714), and/or transmission assembly (712) relative to handle assembly (740). Contacts (720, 752) also electrically couple to provide power to the end effector of the present example. A user may then use the assembled surgical instrument for a procedure. When the user desires to decouple end effector assembly (710) from handle assembly (740), the user may simply pull outwardly on end effector assembly (710) until T-shaped connectors (734, 736, 738) decouple from deflectable distal tabs (748), first actuation mechanism (760), and/or second actuation mechanism (770). A user may then couple a new end effector assembly (710) to handle assembly (740). Alternatively, in the present example, a release feature (780) of handle assembly (740)

may be depressed or slid by a user to actuate first and/or second actuation mechanisms (760, 770) outwardly and/or to deflect distal tabs (748). For instance, release feature (780) may comprise one or more wedge members (not shown) operable to cam first and/or second actuation mechanisms (760, 770) and/or to deflect distal tabs (748) open to permit passage of T-shaped connectors (734, 736, 738). Of course other release mechanisms may be implemented as well. For instance, keyways may be formed in flanges (728, 730, 732) to permit the passage of T-shaped connectors (734, 736, 738) or, in one alternative, flanges (728, 730, 732) may be operable to break-away when removing end effector assembly (710). If flanges (728, 730, 732) are operable to break-away, this may also be an indicator to a user that end effector assembly (710) has previously been used. Still other release mechanisms will be apparent to one of ordinary skill in the art in view of the teachings herein.

Of course other configurations for fifth coupling mechanism (700) will be apparent to one of ordinary skill in the art in view of the teachings herein. For instance, if an ultrasonic end effector is included, such as end effector (80), proximal shaft (726) and/or flange (732) may be threadably coupled to a transducer, such as transducer (100), within handle assembly (740). Distal shaft (722) and middle shaft (724) may also be mechanically coupled to other components within handle assembly (740) for use, such as to operate clamp arm (84) described above, though this is merely optional. In this case, handle assembly (740) may further be configured in a similar manner to multi-piece handle assembly (60) described above. As will become apparent from the previous and later disclosures herein, various other electrical and/or mechanical coupling mechanisms and/or features may be combined with fifth coupling mechanism (700) as well.

F. Exemplary Resiliently Biased Bearings

Figure 10A:
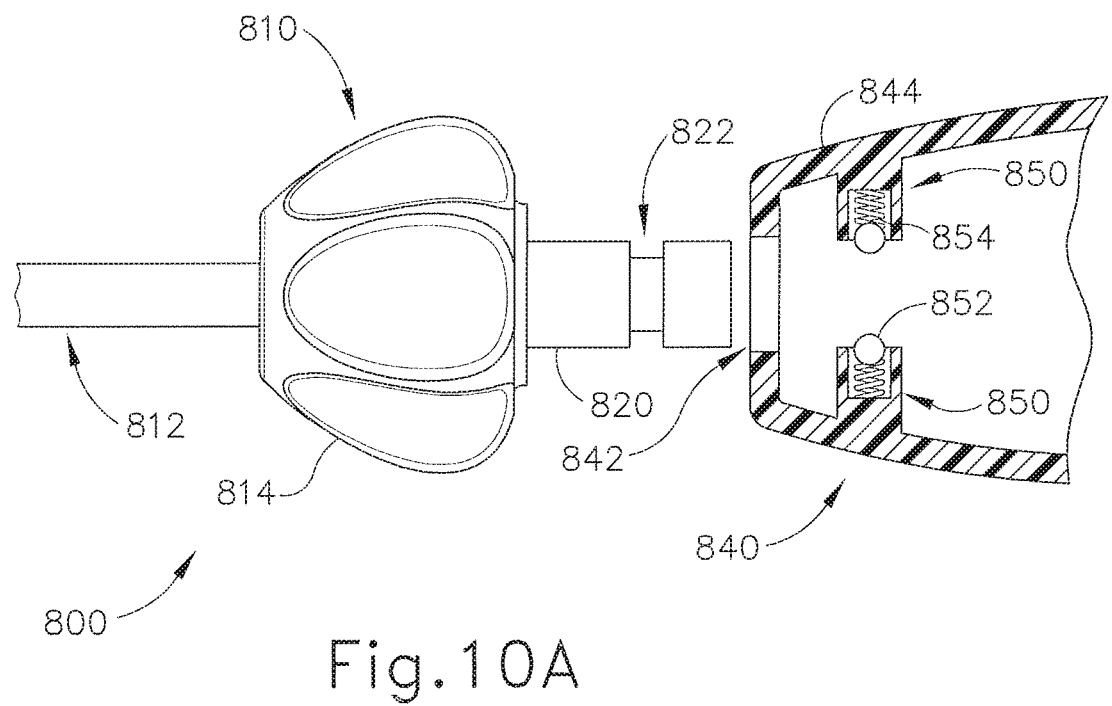
FIG. 10A depicts a side elevation view of a sixth exemplary coupling mechanism with a portion of a handle assembly removed to show the interior thereof and showing a decoupled end effector assembly.
Figure 10B:
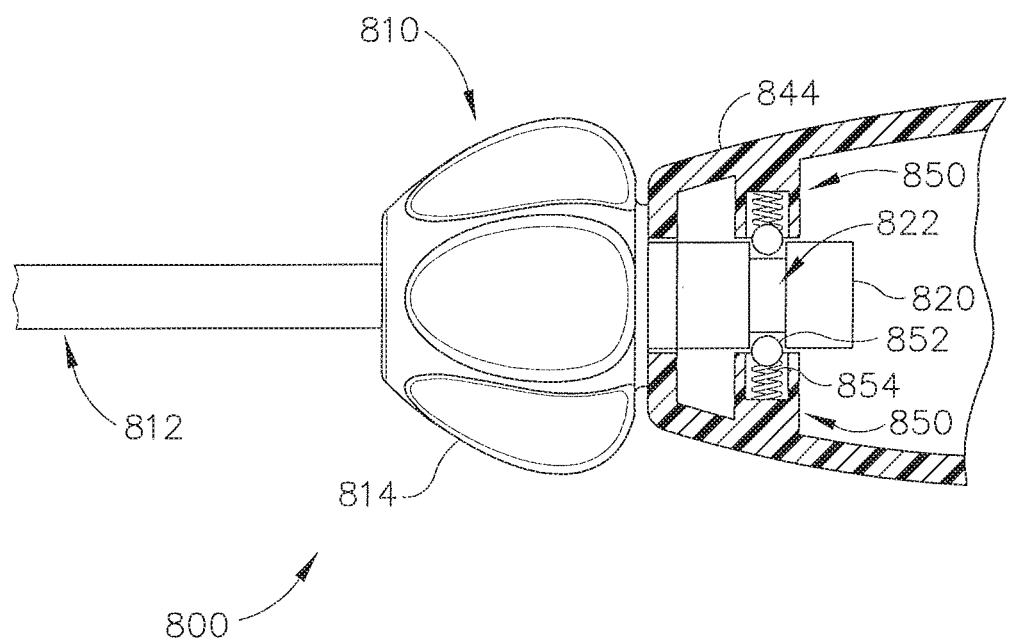
FIG. 10B depicts a side elevation view of the coupling mechanism of FIG. 10A showing the end effector assembly coupled to the handle assembly.

A sixth exemplary coupling mechanism (800) comprises a pair of resiliently biased ball bearing members (850) disposed within handle assembly (840) and configured to engage a circumferential recess (822) of shaft (820) of exemplary end effector assembly (810), shown in FIGS. 10A-10B. In the present example, end effector assembly (810) comprises a transmission assembly (812), a rotation knob (814), and a shaft (820) extending proximally relative to rotation knob (814). It should be understood that rotation knob (814) is merely optional and may be omitted. Rotation knob (814) is operable to rotate transmission assembly (812) relative to handle assembly (840) and/or shaft (820). An end effector (not shown) is coupled to a distal end of transmission assembly (812). The end effector may include an ultrasonic end effector (80), an RF end effector (200), and/or any other end effector or combination of end effectors as will be apparent to one of ordinary skill in the art in view of the teachings herein. In the instance of an ultrasonic end effector, such as end effector (80), an axial bore (not shown) through shaft (820) may permit mechanical coupling of transmission assembly (812) through shaft (820) to components within handle assembly (840), which may be configured in a similar manner to multi-piece handle assembly (60) described above. In the case of an RF end effector, such as end effector (200), the axial bore may permit a portion of transmission assembly (812) to extend at least partially through shaft (820). Transmission assembly (812) may include an inner slip ring connector that is electrically coupleable to a complementary slip ring connector on the interior of shaft (820) such that an electrical coupling from handle assembly (840) may be made to the end effector. For instance, ball bearings (852) may be electrically coupled to a power source and may couple to a contact within recess (822) as will be described below. In yet another alternative, a fluid coupling may also be made via the bore through shaft (820) and/or elsewhere on end effector assembly (810).

In the present example, shaft (820) comprises a circumferential recess (822) formed distally of the proximal end of shaft (820). Recess (822) may include an electrical contact, such as a copper ring, to electrically couple end effector assembly (810) with ball bearings (852), though this is merely optional. In the present example, handle assembly (840) comprises a casing (844), a distal aperture (842) formed in the casing (844), and a pair of resiliently biased ball bearing members (850) located proximal of distal aperture (842). Distal aperture (842) is configured to receive shaft (820) therein. Resiliently biased ball bearing members (850) each comprise a ball bearing (852) and a biasing spring (854) in a recess at an end of ball bearing members (850). Handle assembly (840) may further be configured in accordance with at least some of the teachings for multipiece handle assembly (60), for handle assembly (152), of U.S. Pat. Pub. No. 2011/0015660, entitled "Rotating Transducer Mount for Ultrasonic Surgical Instruments," published Jan. 20, 2011, issued as U.S. Pat. No. 8,461,744 on Jun. 11, 2013 or of U.S. Pat. No. 6,500,176, entitled "Electrosurgical Systems and Techniques for Sealing Tissue," issued Dec. 31, 2002, the disclosures of which are incorporated by reference herein.

As shown in the sequence of FIGS. 10A-10B, when shaft (820) is inserted through distal aperture (842), shaft (820) initially urges ball bearings (852) against biasing springs (854). Ball bearings (850) continue to be urged against biasing springs (854) until ball bearings (850) encounter recess (822). Biasing springs (854) then push ball bearings (852) into recess (822), thereby coupling ball bearing members (850) to shaft (820). As shown in FIG. 10B, end effector assembly (810) is effectively longitudinally secured to handle assembly (840) by the combination of ball bearing members (850) and recess (822) while still permitting rotational movement of shaft (820), rotation knob (814), and/or transmission assembly (812) relative to handle assembly (840). In the instance of an ultrasonic instrument, shaft (820) of end effector assembly (810) may also be threaded onto a horn of a transducer, such as transducer (100) described above. Such threading may occur prior to, contemporaneously with, or after ball bearings (852) encounter recess (822). Alternatively, in the instance of an RF instrument, shaft (820) may be coupled to one or more electrical connectors (not shown) to couple the end effector to a power source. Merely exemplary electrical couplings are shown and described in reference to FIGS. 15-17. Alternatively, ball bearings (852) and/or biasing springs (854) may be configured to electrically couple the end effector to a power source. A user may then use the assembled surgical instrument for a procedure. When the user desires to decouple end effector assembly (810) from handle assembly (840), the user pulls on end effector assembly (810) until ball bearings (852) compress against biasing springs (854) and permit shaft (820) to clear ball bearings (852). A user may then couple a new end effector assembly (810) to handle assembly (840).

Of course other configurations for sixth coupling mechanism (800) will be apparent to one of ordinary skill in the art in view of the teachings herein. For instance, while the present example shows only two ball bearing members (850), a ring of resiliently biased ball bearing members (850) may be circumferentially disposed within handle assembly (840). Alternatively, in the case of a ring of ball bearing members (850), biasing springs (854) may be omitted and a camming cylindrical sleeve (not shown) may be operable to actuate the ring of ball bearings (852) inwardly into recess (822) of shaft (850). Such a cylindrical sleeve may be resiliently biased or manually actuated via an exterior slider on casing (844). As will become apparent from the previous and later disclosures herein, various other electrical and/or mechanical coupling mechanisms and/or features may be combined with third coupling mechanism (800).

G. Exemplary Lock Key Assembly

A seventh exemplary coupling mechanism (900) comprises an insertable lock key (950) that is insertable into a slot (946) in casing (944) of a handle assembly (940). Lock key (950) is configured to longitudinally secure a proximal assembly (920) of yet another exemplary end effector assembly (910), shown in FIGS. 11A-11B, when proximal assembly (920) is inserted through a distal aperture (942) in casing (944). In the present example, end effector assembly (910) comprises a transmission assembly (912), a gear (916) coupled to transmission assembly (910), and proximal assembly (920) proximal of gear (916), in one merely exemplary configuration, proximal assembly (920) comprises a wave spring assembly for use with an ultrasonic end effector, such as end effector (80) described above. Alternatively, proximal assembly (920) may comprise actuatable components, such as T-connectors and shafts as described in reference to FIGS. 9A-9B, for operating mechanical components of end effector assembly (910). Further still, proximal assembly (920) may include electrical contacts to electrically couple end effector assembly (910) to a power source, such as generator (20) or a power source within handle assembly (940). In yet another alternative, a fluid coupling may also be made via proximal assembly (920) and/or elsewhere on end effector assembly (910). As noted above, an end effector (not shown) is coupled to a distal end of transmission assembly (912). The end effector may include an ultrasonic end effector (80), an RF end effector (200), and/or any other end effector or combination of end effectors as will be apparent to one of ordinary skill in the art in view of the teachings herein.

Handle assembly (940) comprises a casing (944), a distal aperture (942) formed in the casing (944), a rotation knob (914) rotatable relative to casing (944), a yoke assembly (948), and a slot (946) forming in casing (944) and located proximal of distal aperture (942). Yoke assembly (948) is mechanically coupled to a trigger, such as trigger (68), and is operable to actuate one or more components of end effector assembly (910). In the present example, yoke assembly (948) includes a lock slot (949) into which a portion of lock key (950) is insertable. Yoke assembly (948) may further be configured in accordance with at least some of the teachings of U.S. patent application Ser. No. 13/269,899, entitled "Ultrasonic Surgical Instrument with Modular End Effector," filed on even date herewith, issued as U.S. Pat. No. 9,050,125 on Jun. 9, 2015, and/or U.S. Pat. Pub. No. 2011/0015660, entitled "Rotating Transducer Mount for Ultrasonic Surgical Instruments," published Jan. 20, 2011, issued as U.S. Pat. No. 8,461,744 on Jun. 11, 2013, the disclosures of which are incorporated by reference herein. While the present example shows slot (946) as a slot on the top side of casing (944), is should be understood that slot (946) may be located at other locations on casing (944) as will be apparent to one of ordinary skill in the art in view of the teachings herein. Rotation knob (914) of the present example includes teeth that are complementary to those of gear (916) and that are formed in a cylindrical recess of rotation knob (914) such that gear (916) is insertable therein and engages rotation knob (914) when end effector assembly (910) is coupled to handle assembly (940). Of course further configurations and features for handle assembly (940) will be apparent to one of ordinary skill in the art in view of the teachings herein.

Lock key (950) of the present example includes a semicircular notch (952) configured to partially encircle transmission assembly (912) when end effector (910) is inserted into handle assembly (940) and lock key (950) is inserted into slot (946). Notch (952) is sized to be smaller than proximal assembly (920), such that proximal assembly (920) may not be translated distally when lock key (950) engages transmission assembly (912). In one alternative, notch (952) may be configured to partially encircle a portion of proximal assembly (920). Still further, notch (952) may be a rectangular notch configured to engage flat portions (not shown) on transmission assembly (912) and/or proximal assembly (920). For instance, the rotational movement of proximal assembly (920) may be constrained by a rectangular notch of lock key (950), and proximal assembly (920) may concurrently be coupled to yoke assembly (948) by the insertion of lock key (950) into slot (946) and lock slot (949). Of course still further configurations for lock key (950), end effector assembly (910), and/or handle assembly (940) will be apparent to one of ordinary skill in the art in view of the teachings herein. For instance, handle assembly (940) may further be configured in accordance with at least some of the teachings for multi-piece handle assembly (60), for handle assembly (152), of U.S. Pat. Pub. No. 2011/0015660, entitled "Rotating Transducer Mount for Ultrasonic Surgical Instruments," published Jan. 20, 2011, issued as U.S. Pat. No. 8,461,744 on Jun. 11, 2013 or of U.S. Pat. No. 6,500,176, entitled "Electrosurgical Systems and Techniques for Sealing Tissue," issued Dec. 31, 2002, the disclosures of which are incorporated by reference herein.

As shown FIG. 11A, lock key (950) is initially removed from handle assembly (940). Proximal assembly (920) and a proximal portion of transmission assembly (912) are then inserted through an opening in rotation knob (914) until gear (916) encounters rotation knob (914). Gear (916) is then rotated until insertion is possible into complementary teeth in the cylindrical recess of rotation knob (914). Once gear (916) is inserted into rotation knob (914), proximal assembly (920) may optionally be torqued down onto a horn of a transducer, such as transducer (100) described above, electrically coupled to an electrical connection in handle assembly (940), and/or otherwise coupled therein. Merely exemplary electrical couplings are shown and described in reference to FIGS. 15-17. Such threading, electrical coupling, and/or otherwise may occur prior to, contemporaneously with, or after inserting gear (916) into rotation knob (914). If flat portions are included on transmission assembly (912) and/or proximal assembly (920), rotation knob (914) and/or transmission assembly (912) may be rotated to align the flat portions with slot (946). In the present example, rotation knob (914) need not be rotated as notch (952) is a semi-circular notch configured to fit around transmission assembly (912). Lock key (950) is then inserted into slot (946) and lock slot (949) to secure end effector assembly (910) to handle assembly (940) and/or yoke assembly (948) therein. A user may then use the assembled surgical instrument for a procedure. When the user desires to decouple end effector assembly (910) from handle assembly (940), the user removes lock key (950) and pulls out end effector assembly (910). A user may then couple a new end effector assembly (910) to handle assembly (940).

Of course other configurations for seventh coupling mechanism (900) will be apparent to one of ordinary skill in the art in view of the teachings herein. For instance, lock key (950) may include snap fittings (not shown) and/or a seal to couple and/or seal lock key (950) to casing (944). Lock key (950) may also include resilient ends to snap around transmission assembly (912) and/or proximal assembly (920). As will become apparent from the previous and later disclosures herein, various other electrical and/or mechanical coupling mechanisms and/or features may be combined with seventh coupling mechanism (900).

H. Exemplary Locking Tab Assembly

Figure 12:
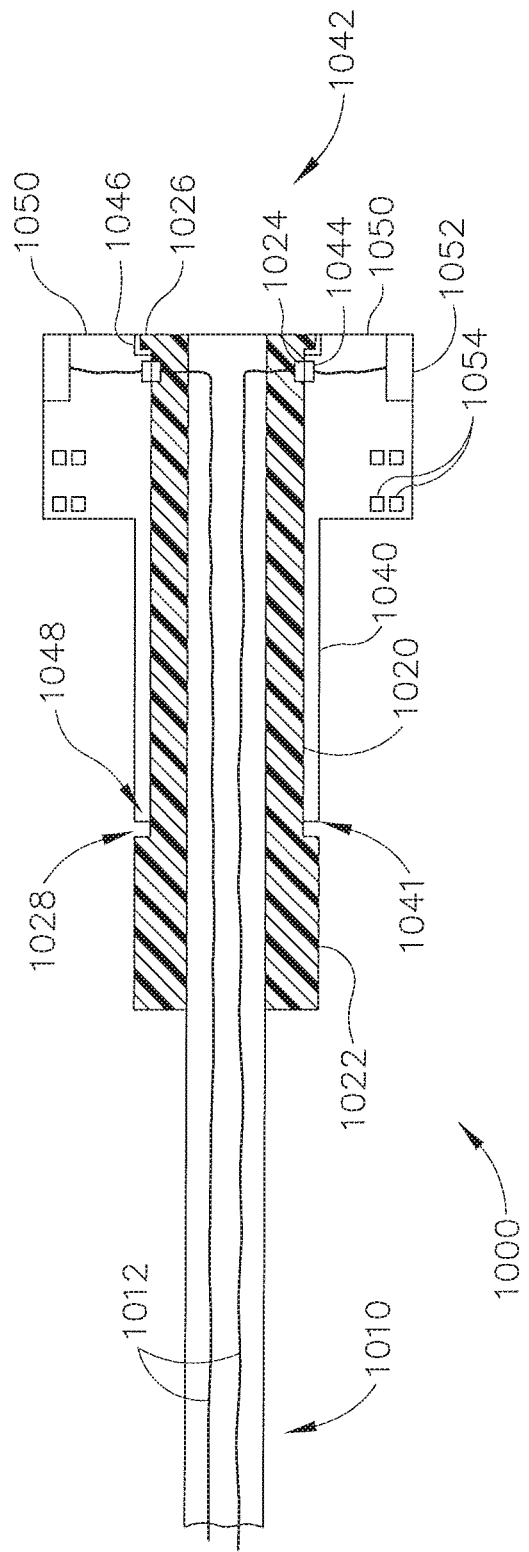
FIG. 12 depicts a side cross-sectional view of an exemplary end effector assembly for use in an eighth exemplary coupling mechanism.
Figure 14:
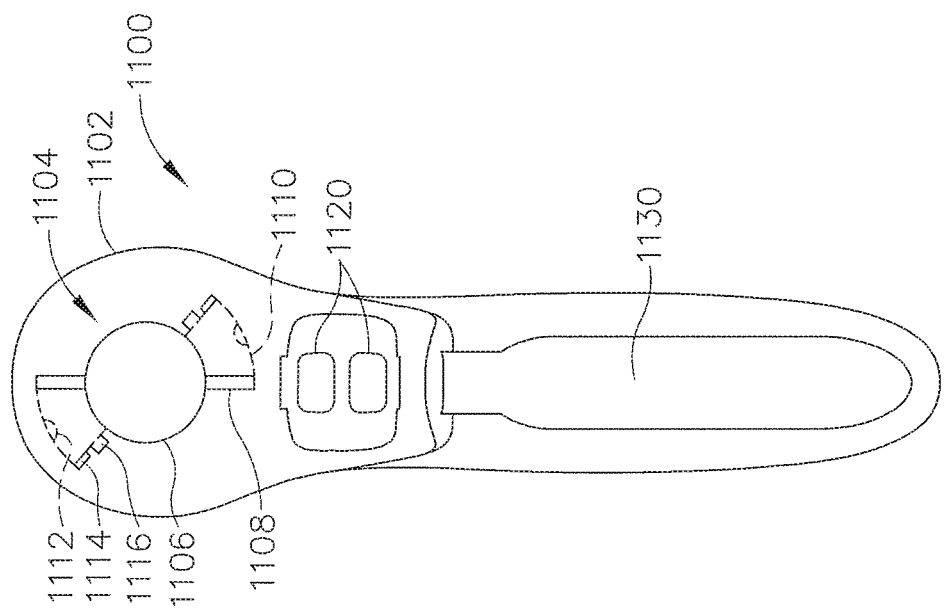
FIG. 14 depicts a front elevation view of a handle assembly configured to receive the end effector assembly of FIG. 12.
Figure 13:
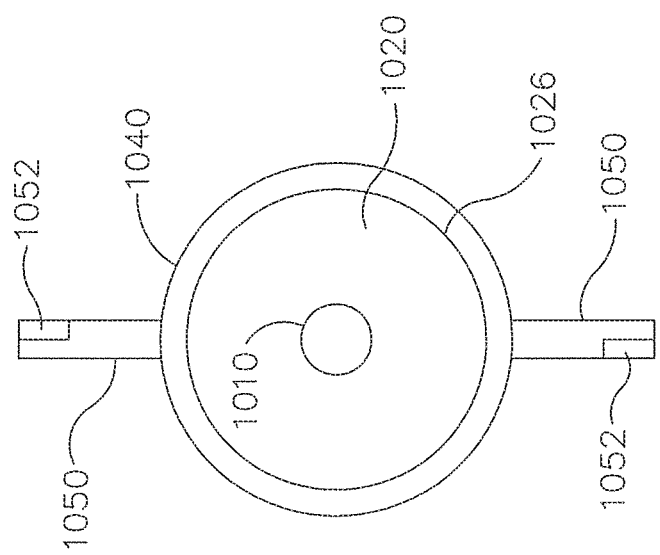
FIG. 13 depicts a rear elevation view of the end effector assembly of FIG. 12.

An eighth exemplary coupling mechanism comprises an end effector assembly (1000) having a pair of locking tabs (1050) extending from opposing sides of a bolt portion (1040) that rotatably lock into rotational recesses (1110) of a handle assembly (1100), shown in FIGS. 12-14. Referring initially to FIG. 12, end effector assembly (1000) comprises a transmission assembly (1010), a rotation portion (1020), and a bolt portion (1040). As shown in cross-section in FIG. 12, transmission assembly (1010) is fixedly secured to and extends through rotation portion (1020). It should be understood that rotation portion (1020) is merely optional and transmission assembly (1010) may be fixedly coupled to bolt portion (1040) or coupled such that transmission assembly (1010) may rotate relative to bolt portion (1040). Rotation portion (1020) comprises a rotation knob (1022) that is operable to rotate transmission assembly (1010) relative to handle assembly (1100) and/or bolt portion (1040). An end effector (not shown) is coupled to a distal end of transmission assembly (1010). The end effector may include an ultrasonic end effector (80), an RF end effector (200), and/or any other end effector or combination of end effectors as will be apparent to one of ordinary skill in the art in view of the teachings herein. In the example shown, conductive wires (1012) extend through transmission assembly (1010) and are coupled to a first slip ring (1024) mounted on an exterior surface of rotation portion (1040) located near the proximal end of end effector assembly (1000).

Bolt portion (1040) includes a slip ring contacts (1044) (e.g., brushes, pins, etc.) mounted to an interior surface of bolt portion (1040) that electrically couples to first slip ring (1024) such that first and second slip rings (1024, 1044) are electrically coupled while permitting 360 degree rotation of rotation portion (1020) relative to bolt portion (1040). In the present example, bolt portion (1040) is a coaxial tubular cylinder disposed about a portion of rotation portion (1020), shown in FIGS. 12-13. A proximal flange (1026) on rotation portion (1020) and a proximal ledge (1046) at proximal end (1042) of bolt portion (1040) and a distal flange (1028) on rotation portion (1020) and a distal ledge (1048) at distal end (1041) of bolt portion (1040) restrict the longitudinal movement of bolt portion (1040) relative to rotation portion (1020) while permitting rotation of bolt portion (1040) and/or rotation portion (1020) relative to the other and/or handle assembly (1100).

Bolt portion (1040) further comprises a pair of locking tabs (1050) extending outwardly from bolt portion (1040) on opposing sides of bolt portion (1040). While a pair of locking tabs (1050) are shown in FIGS. 12-13, it should be understood that a single locking tab (1050) or more than two locking tabs (1050) may be included. For instance, in some merely exemplary alternatives, three tabs (1050) or four tabs (1050) may extend from bolt portion (1040). Locking tabs (1050) of the present example comprise one or more electrical contacts (1052) that are electrically coupled to second slip ring (1044) such that electrical contacts (1052) may provide power to the end effector when power is coupled to electrical contacts (1052). Locking tabs (1050) further comprise one or more optically perceivable indicators (1054) (such as openings) operable to identify end effector assembly (1000) when coupled to handle assembly (1100). For instance, one or more optoelectronic sensors (1116) (shown in FIG. 14) may be included at recesses (1110) to detect the presence or absence of indicators (1054) at various positions on locking tabs (1050). Such absence and/or detection may be converted to bits of data which may be used to identify the type, size, and/or other features of end effector assembly (1000). Alternatively, optically perceivable indicators (1054) may instead be configured to transmit data from one or more sensors at the end effector to optoelectronic sensors (1116) (e.g., fiber optic transmissions). Further still, indicators (1054) may instead be replaced with an RFID component and optoelectronic sensors (1116) may be replaces with an RFID reader. For instance, a near-field RFID system may be used. By way of example only, such data and/or information may be used to adjust settings on generator (20), control settings of a control module within handle assembly (1100), and/or any other adjustable electronic component. For instance, the operational settings for toggle buttons (1120) (shown in FIG. 14) may be adjusted depending upon the type and/or size of the attached end effector. In some versions, indicators (1054) and optoelectronic sensors (1116) (or variations thereof, such as RFID components) may be configured to authenticate end effector assembly (1000) as a suitable and/or authorized end effector assembly for use with handle assembly (1100).

Handle assembly (1100), shown in FIG. 14, comprises a casing (1102), a distal aperture (1104) configured to receive the proximal end of end effector (1100), one or more toggle buttons (1120), a trigger (1130), and a pair of rotational recesses (1110) (shown in phantom) proximal of distal aperture (1104). Distal aperture (1104) includes a circular portion (1106) and vertical tab portions (1108), though it should be understood that tab portions (1108) may be horizontally oriented or at any other angle. Rotational recesses (1110) are shown with a rotational angle of approximately 45 degrees relative to the vertical tab portions (1108) such that when locking tabs (1050) are inserted into distal aperture (1104) and rotated into rotational recesses (1110), rotational recesses (1110) and locking tabs (1050) prevent end effector assembly (1000) from translating distally out of distal aperture (1104). It should be understood that rotational recesses (1110) may extend through an angular range of approximately 10 degrees to 180 degrees. In some configurations, the angular range of rotational recesses (1110) may be less than 10 degrees, for instance one degree, if such rotation prevents end effector assembly (1000) from translating distally out of distal aperture (1104). Detents (1112) (also shown in phantom) are provided on a portion of rotational recesses (1110) to resist the rotational movement of locking tabs (1050), thereby further securing locking tabs (1050) within rotational recesses (1110). It should be understood that detents (1112) are merely optional. One or more electrical contacts (1114) and optoelectronic sensors (1116) are coupled to an inner rotational face of rotational recesses (1110) to couple to and/or sense electrical contacts (1052) and/or optically perceivable indicators (1054), respectively. Of course, such components may be omitted. Furthermore, a spring (not shown) may be provided on a proximal wall within handle assembly (1100) to engage proximal end (1042) of bolt portion (1040) and/or rotation portion (1020) when end effector assembly (1100) is inserted. Accordingly, the spring may provide a distal bias to facilitate single handed removal of bolt portion (1040) from within handle assembly (1100).

When a user desires to couple end effector assembly (1000) to handle assembly (1100) according to the presently described eighth exemplary coupling mechanism, the user initially aligns locking tabs (1050) with vertical portions (1108) of distal aperture (1104) and inserts the proximal end of end effector assembly (1000) into distal aperture (1104). If a spring is provided at the proximal wall, proximal end (1042) of bolt portion (1040) and/or rotation portion (1020) may engage the spring. As a user further inserts end effector assembly (1000), the spring compresses. The spring may be in a compressed state when bolt portion (1040) is rotated to lock locking tabs (1050) into rotational recesses (1110). In some versions the user may grasp a distal portion of bolt portion (1040), which may include knurling, ridging, scallops, etc., to rotate locking tabs (1050) into rotational recesses (1110). Locking tabs (1050) of the present example are rotated past the resistance provided by detents (1112) and secured such that the one or more electrical contacts (1114) couple to electrical contacts (1052) and optoelectronic sensors (1116) sense indicators (1054). The user may then use the assembled surgical instrument for a procedure. When the user desires to decouple end effector assembly (1000) from handle assembly (1100), the user rotates bolt portion (1040) to overcome the resistance of detents (1112). Once locking tabs (1050) are vertically aligned with vertical portions (1108) of distal aperture (1104), the user then pulls end effector assembly (1000) out of handle assembly (1100). If a spring has been included on the proximal wall, then the spring may aid in the ejection of end effector assembly (1000) from handle assembly (1100). A user may then couple a new end effector assembly (1000) to handle assembly (1100).

In one configuration for use with an ultrasonic end effector, such as end effector (80), transmission assembly (1010) may extend proximally beyond proximal face (1042) of bolt portion (1040). Transmission assembly (1010) may be mechanically coupled to a horn of a transducer, such as transducer (100), and/or other mechanically couplings, such as those that actuate clamp arm (84), within handle assembly (1100), which may be configured in a similar manner to multi-piece handle assembly (60) described above. In the case of an RF end effector, such as end effector (200), transmission assembly (1010) may mechanically and/or electrically couple to components within handle assembly (1100). Alternatively, as described above, locking tabs (1050) may provide power to the RF end effector via electrical contacts (1114) coupled to electrical contacts (1052). In yet a further variation, locking tabs (1050) may lock into a yoke assembly, such as yoke assembly (948) described above. Still further configurations for end effector assembly (1000) and/or handle assembly (1100) will be apparent to one of ordinary skill in the art in view of the teachings herein. For instance, in one merely exemplary alternative configuration, rotational recesses (1110) may be configured to be helically shaped recesses extending proximally from vertical portions (1108) such that locking tabs (1050) follow the helical path as end effector assembly (1000) is pushed into handle assembly (1100). Detents (1112) may secure locking tabs (1050) within the helical recesses.

Of course other configurations for the eighth coupling mechanism will be apparent to one of ordinary skill in the art in view of the teachings herein. As will become apparent from the previous and later disclosures herein, various other electrical and/or mechanical coupling mechanisms and/or features may be combined with the eighth coupling mechanism. For instance, optically perceivable indicators (1054) and optoelectronic sensors (1116) may be incorporated into any of the end effector assemblies and handle assemblies herein described.

While the foregoing coupling mechanisms focused upon the mechanical coupling of the various end effector assemblies with the handle assembly (though various electrical couplings were described as well), for a variety of end effectors, an electrical coupling may also be included. Accordingly, the following descriptions describe various electrical coupling mechanisms that may be incorporated, in full or in part, with the foregoing coupling mechanisms and/or any other coupling mechanisms.

I. Exemplary Threaded Electrode Connection

Figure 15:
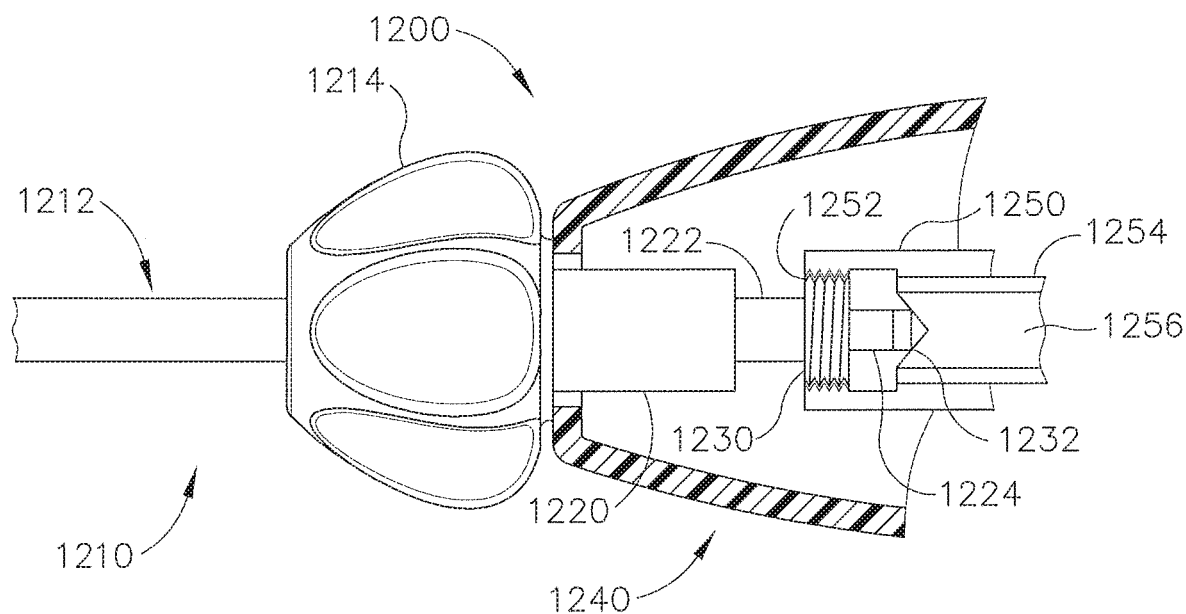
FIG. 15 depicts a side elevation view of a first electrical coupling mechanism with a portion of a handle assembly removed to show the interior thereof and showing a coupled end effector assembly.

An exemplary first electrical coupling mechanism (1200) includes one or more threaded electrodes (1230) on an end effector assembly (1210) that thread into complementary threads (1252) of a threaded member (1250) within a handle assembly (1240), shown in FIG. 15. In the present example, exemplary end effector assembly (1210) comprises a transmission assembly (1212), a rotation knob (1214), and a shaft (1220) extending proximally relative to rotation knob (1214). It should be understood that rotation knob (1214) is merely optional and may be omitted. Rotation knob (1214) is operable to rotate transmission assembly (1212) relative to a handle assembly (1240) and/or shaft (1220). An end effector (not shown) is coupled to a distal end of transmission assembly (1212). The end effector may include an ultrasonic end effector (80), an RF end effector (200), and/or any other end effector or combination of end effectors as will be apparent to one of ordinary skill in the art in view of the teachings herein.

In the present example, a second shaft (1222) extends proximally from shaft (1220). One or more threaded electrodes (1230) are coupled to second shaft (1222) and are configured to thread into complementary threads (1252) of threaded member (1250) within handle assembly (1240). If more than one threaded electrode (1230) is included (e.g., longitudinally and/or radially spaced apart from electrode (1230)), then an insulator (not shown) may separate adjacent electrodes (1230). A post (1224) extends proximally from threaded electrode (1230). An opposite polarity contact (1232) is coupled to the proximal end of post (1224) and is configured to electrically couple to a corresponding contact (1256) within threaded member (1250). One or more insulated wires may extend through post (1224), second shaft (1222), shaft (1220), and/or transmission assembly (1212) to electrically couple the end effector to threaded electrode (1230) and/or contact (1232). In the present example, threaded member (1250) is a tubular member having complementary threads (1252) at the distal end. Threaded member (1250) is disposed about a coaxial tubular insulator (1254) which is, in turn, disposed about corresponding contact (1256). In the present example, threaded member (1250) is a conductive component that is electrically coupled to the cathode of a power supply and corresponding contact (1256) is electrically coupled to the anode of the power supply. Of course, the polarity may be reversed. Insulator (1254) isolates threaded member (1250) from corresponding contact (1256).

When end effector assembly (1210) is coupled to handle assembly (1240) (either by one of the foregoing coupling mechanisms and/or otherwise), threaded electrode (1230) is threaded into complementary threads (1252), thereby electrically coupling threaded electrode (1232) with threaded member (1250). Threaded electrode (1230) may continue to thread into complementary threads (1252) until contact (1232) abuts and electrically couples to corresponding contact (1256). Thus, power may be supplied to the end effector of end effector assembly (1200).

Of course other configurations for first electrical coupling mechanism (1200) may be used. Indeed, in one alternative, contact (1232) and corresponding contact (1256) may be complementary threaded components and threaded electrode (1230) may be a disc configured to abut and electrically couple to threaded member (1250). Contact (1232) and threaded electrode (1230) may both be threaded components or may both be contact electrical connections. Still other configurations for first electrical coupling mechanism (1200) will be apparent to one of ordinary skill in the art in view of the teachings herein. As is apparent from the disclosures herein, various other electrical and/or mechanical coupling mechanisms and/or features may be combined with first electrical coupling mechanism (1200) as well.

J. Exemplary Resiliently Biased Electrical Connections

Figure 16:
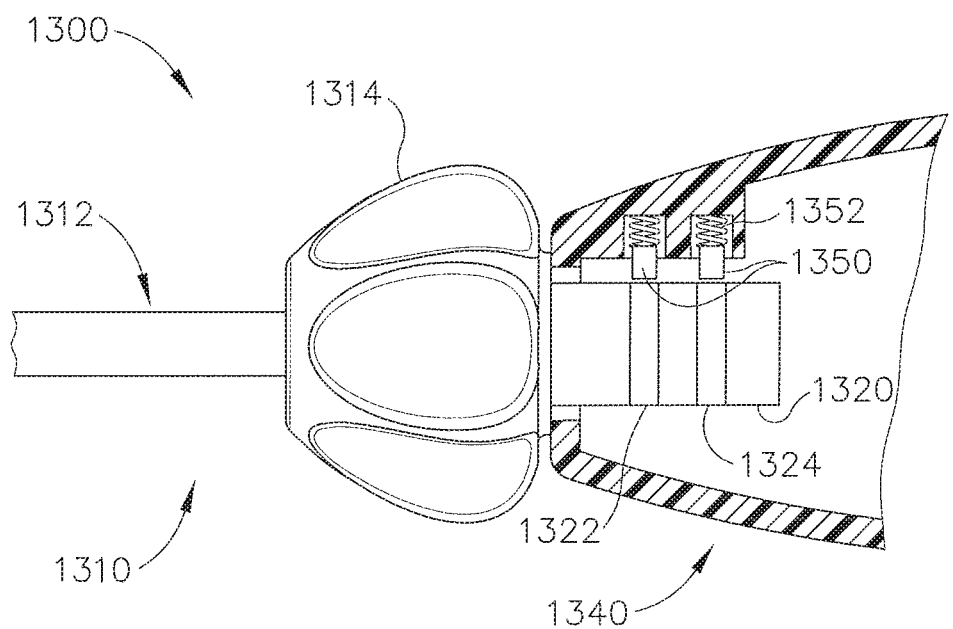
FIG. 16 depicts a side elevation view of a second electrical coupling mechanism with a portion of a handle assembly removed to show the interior thereof and showing a coupled end effector assembly.

An exemplary second electrical coupling mechanism (1300) includes one or more spring loaded contacts (1350) within a handle assembly (1340) to contact and electrically couple to corresponding contacts (1322, 1324) on another exemplary end effector assembly (1310), shown in FIG. 16. In the present example, exemplary end effector assembly (1310) comprises a transmission assembly (1312), a rotation knob (1314), and a shaft (1320) extending proximally relative to rotation knob (1314). It should be understood that rotation knob (1314) is merely optional and may be omitted. Rotation knob (1314) is operable to rotate transmission assembly (1312) relative to a handle assembly (1340) and/or shaft (1320). An end effector (not shown) is coupled to a distal end of transmission assembly (1312). The end effector may include an ultrasonic end effector (80), an RF end effector (200), and/or any other end effector or combination of end effectors as will be apparent to one of ordinary skill in the art in view of the teachings herein.

In the present example, contacts (1322, 1324) are ring contacts coupled to and circumferentially disposed about shaft (1320). As shown in FIG. 16, spring loaded contacts (1350) are biased towards shaft (1320) by springs (1352). When end effector (1310) is inserted into handle assembly (1340) and longitudinally aligned (such as by one of the coupling mechanisms herein described), then a first spring loaded contact (1350) electrically couples to a corresponding contact (1322) and a second spring loaded contact (1350) electrically couples to another corresponding contact (1324). Accordingly, the end effector of end effector assembly (1310) may be supplied with power via the electrical coupling of spring loaded contacts (1350) with contacts (1322, 1324) even when end effector assembly (1310) is rotated relative to handle assembly (1340). In some versions, biased leaf spring contacts may be used instead of spring loaded contacts (1350).

Figure 17:
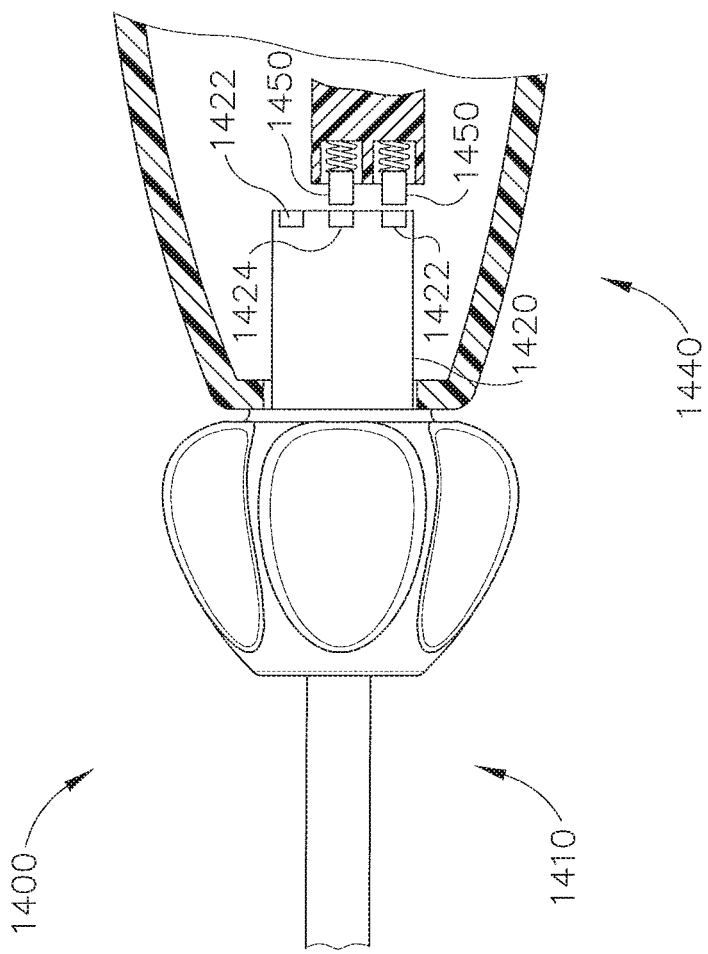
FIG. 17 depicts a side elevation view of a third electrical coupling mechanism with a portion of a handle assembly removed to show the interior thereof and showing a coupled end effector assembly.

Of course other configurations for second electrical coupling mechanism (1300) may be used. Indeed, in one alternative, a third electrical coupling mechanism (1400) is depicted in FIG. 17. Similar to second electrical coupling mechanism (1300), a pair of spring loaded contacts (1450) are mounted in handle assembly (1440), though in the present example, spring loaded contacts (1450) are horizontally mounted. End effector assembly (1410) includes a shaft (1420) on the proximal end of which are an annular contact (1422) coaxial to the axis of shaft (1420) and a central contact (1424) located on the axis of shaft (1420). When an end effector assembly (1410) is inserted into housing assembly (1440), a first spring loaded contact (1450) electrically couples to annular contact (1422) and a second spring loaded contact (1450) electrically couples to central contact (1424). Accordingly, the end effector of end effector assembly (1410) may be supplied with power via the electrical coupling of spring loaded contacts (1450) with contacts (1422, 1424) even when end effector assembly (1410) is rotated. Still other configurations for second electrical coupling mechanism (1300) and/or third electrical coupling mechanism (1400) will be apparent to one of ordinary skill in the art in view of the teachings herein. As is apparent from the disclosures herein, various other electrical and/or mechanical coupling mechanisms and/or features may be combined with second electrical coupling mechanism (1300) and/or third electrical coupling mechanism (1400) as well.

For the foregoing examples, it should be understood that the handle assemblies and/or end effectors may be reusable, autoclavable, and/or disposable. For instance, the foregoing end effectors may be disposable while the handle assemblies are reuseable and/or autoclavable. In addition, if internal power sources are used with the foregoing handle assemblies, the internal power sources may be rechargeable. For instance, the handle assemblies may be recharged using a plug in recharge, by removing and recharging the batteries, by induction, and/or by any other method as will be apparent to one of ordinary skill in the art in view of the teachings herein. Furthermore, alignment features or guides may be included to aid in the alignment and coupling of the end effectors with handle assemblies. Such guides may help prevent damage to the end effector and/or handle assembly during the assembly of the surgical instrument.

While certain configurations of exemplary surgical instruments have been described, various other ways in which surgical instruments may be configured will be apparent to those of ordinary skill in the art in view of the teachings herein. By way of example only, surgical instruments referred to herein may be constructed in accordance with at least some of the teachings of U.S. Pat. Nos. 6,500,176; 6,783,524; 7,416,101; 7,738,971; 6,783,524; U.S. Pub. No. 2006/0079874, now abandoned; U.S. Pub. No. 2007/0191713, now abandoned; U.S. Pub. No. 2007/0282333, now abandoned; U.S. Pub. No. 2008/0200940, now abandoned; U.S. Pub. No. 2009/0209990, issued as U.S. Pat. No. 8,657,174 on Feb. 25, 2014; U.S. Pub. No. 2009/0143797, issued as U.S. Pat. No. 8,419,757 on Apr. 16, 2013; U.S. Pub. No. 2010/0069940, issued as U.S. Pat. No. 9,023,071 on May 5, 2015; and/or U.S. Provisional Application Ser. No. 61/410,603, now expired, the disclosures of which are herein incorporated by reference.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Embodiments of the present invention have application in conventional endoscopic and open surgical instrumentation as well as application in robotic-assisted surgery. For instance, those of ordinary skill in the art will recognize that various teaching herein may be readily combined with various teachings of U.S. Pat. No. 6,783,524, entitled.

"Robotic Surgical Tool with Ultrasound. Cauterizing and Cutting Instrument," published Aug. 31, 2004, the disclosure of which is incorporated by reference herein.

By way of example only, embodiments described, herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

Embodiments of the devices disclosed herein can be reconditioned for reuse after at least one use. Reconditioning may include any combination of the steps of disassembly of the device, followed by cleaning or replacement of particular pieces, and subsequent reassembly. In particular, embodiments of the devices disclosed herein may be disassembled, and any number of the particular pieces or parts of the devices may be selectively replaced or removed in any combination. Upon cleaning and/or replacement of particular parts, embodiments of the devices may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument comprising:
   (a) a body assembly including:
      (i) an aperture disposed at a distal end of the body assembly, and
      (ii) a first electrical contact; and
   (b) an end effector assembly configured to releasably couple with the body assembly, wherein the end effector assembly includes:
      (i) a proximal shaft portion configured to be received through the aperture of the body assembly, wherein the proximal shaft portion includes a second electrical contact configured to electrically and releasably couple with the first electrical contact,
      (ii) an energy transmission assembly extending distally from the body assembly, wherein the energy transmission assembly is configured to transmit RF energy distally via the electrical coupling between the first and second electrical contacts, and
      (iii) an end effector at a distal end of the energy transmission assembly, wherein the end effector is operable to treat patient tissue with RF energy received from the energy transmission assembly,
   wherein the end effector assembly is selectively rotatable relative to the body assembly,
   wherein the first and second electrical contacts are configured to remain electrically coupled throughout rotation of the end effector assembly relative to the body assembly.

2. The surgical instrument of claim 1, wherein at least one of the first electrical contact or the second electrical contact is resiliently biased toward the other of the first electrical contact or the second electrical contact.

3. The surgical instrument of claim 2, wherein the body assembly further includes a compression spring configured to resiliently bias the first electrical contact toward the second electrical contact.

4. The surgical instrument of claim 1, wherein the first electrical contact and the second electrical contact define a slip ring electrical connection.

5. The surgical instrument of claim 1, wherein the second electrical contact includes an annular electrical contact.

6. The surgical instrument of claim 5, wherein the proximal shaft portion includes an annular recess that defines the annular electrical contact.

7. The surgical instrument of claim 5, wherein the annular electrical contact extends circumferentially about the proximal shaft portion, wherein the first electrical contact extends radially inwardly toward the proximal shaft portion to engage the annular electrical contact.

8. The surgical instrument of claim 5, wherein the annular electrical contact is disposed on a proximal face of the proximal shaft portion coaxially with a central axis of the proximal shaft portion, wherein the first electrical contact extends distally toward the proximal face to engage the annular electrical contact, wherein the first electrical contact is radially offset from the central axis.

9. The surgical instrument of claim 8, wherein end effector assembly further includes an additional second electrical contact disposed on the proximal face of the proximal shaft portion, wherein the body assembly further includes an additional first electrical contact that extends distally toward the proximal face to engage the additional second electrical contact.

10. The surgical instrument of claim 9, wherein the additional second electrical contact is arranged coaxially with a central axis of the proximal shaft portion, wherein the first electrical contact extends coaxially with the central axis.

11. The surgical instrument of claim 1, wherein the second electrical contact is provided on a proximal-most face of the proximal shaft portion.

12. The surgical instrument of claim 1, wherein the body assembly includes a pair of first electrical contacts and the end effector assembly includes a pair of second electrical contacts configured to electrically couple with the first electrical contacts, wherein each of the first electrical contacts is configured to align coaxially with a respective one of the second electrical contacts.

13. The surgical instrument of claim 1, wherein the first electrical contact is configured to threadedly engage the second electrical contact.

14. The surgical instrument of claim 1, wherein the end effector includes a pair of electrodes configured to deliver RF energy to tissue, wherein the body assembly includes a pair of first electrical contacts and the end effector assembly includes a pair of second electrical contacts configured to electrically couple with the first electrical contacts, wherein each of the second electrical contacts is electrically coupled with a respective one of the electrodes.

15. The surgical instrument of claim 1, wherein the body assembly further includes a user input feature, wherein the end effector is configured to deliver RF energy to the patient tissue in response to actuation of the user input feature.

16. A surgical instrument comprising:
(a) a handle assembly including:
 (i) an aperture disposed at a distal end of the handle assembly, and
 (ii) a first electrical contact; and
(b) an end effector assembly configured to releasably couple with the handle assembly, wherein the end effector assembly includes:
 (i) a proximal shaft portion configured to be received through the aperture of the handle assembly, wherein the proximal shaft portion includes an annular second electrical contact configured to electrically and releasably couple with the first electrical contact,
 (ii) an energy transmission assembly extending distally from the handle assembly, wherein the energy transmission assembly is configured to transmit RF energy distally via the electrical coupling between the first and second electrical contacts, and
 (iii) an end effector at a distal end of the energy transmission assembly, wherein the end effector is operable to treat patient tissue with RF energy received from the energy transmission assembly,
wherein the end effector assembly is selectively rotatable relative to the handle assembly,
wherein the first and second electrical contacts are configured to remain electrically coupled throughout rotation of the end effector assembly relative to the handle assembly.

17. The surgical instrument of claim 6, wherein the first electrical contact is resiliently biased into engagement with the annular second electrical contact.

18. The surgical instrument of claim 6, wherein the annular second electrical contact is defined by an annular recess formed in the proximal shaft portion.

19. A surgical instrument comprising:
(a) a handle assembly including:
 (i) an aperture disposed at a distal end of the handle assembly, and
 (ii) a pair of first electrical contacts; and
(b) an end effector assembly configured to releasably couple with the handle assembly, wherein the end effector assembly includes:
 (i) a proximal shaft portion configured to be received through the aperture of the handle assembly, wherein the proximal shaft portion includes a pair of second electrical contacts configured to electrically and releasably couple with the first electrical contacts, wherein each of the first electrical contacts is configured to align coaxially with a respective one of the second electrical contacts,
 (ii) an energy transmission assembly extending distally from the handle assembly, wherein the energy transmission assembly is configured to transmit RF energy distally via the electrical coupling between the first electrical contacts and the second electrical contacts, and
 (iii) an end effector at a distal end of the energy transmission assembly, wherein the end effector is operable to treat patient tissue with RF energy received from the energy transmission assembly,
wherein the end effector assembly is selectively rotatable relative to the handle assembly,
wherein the first electrical contacts and the second electrical contacts are configured to remain electrically coupled throughout rotation of the end effector assembly relative to the handle assembly.

20. The surgical instrument of claim 9, wherein the handle assembly includes a first threaded member and a first cylindrical member that are arranged coaxially and provide the pair of first electrical contacts, wherein the proximal shaft portion includes a second threaded member and a second cylindrical member that are arranged coaxially and provide the pair of second electrical contacts, wherein the first and second threaded members are configured to threadedly engage to define a first electrical connection, wherein the first and second cylindrical members are configured to engage to define a second electrical connection.

* * * * *